US012780798B2

(12) United States Patent
Li et al.

(10) Patent No.: US 12,780,798 B2
(45) Date of Patent: Nov. 3, 2026

(54) PRMT5 INHIBITOR COMPOUNDS

(71) Applicant: University of Florida Research Foundation, Incorporated, Gainesville, FL (US)

(72) Inventors: Chenglong Li, Gainesville, FL (US); Xiaozhi Yang, Gainesville, FL (US); Wei Zhou, Gaithersburg, MD (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 1368 days.

(21) Appl. No.: 17/599,505

(22) PCT Filed: Mar. 27, 2020

(86) PCT No.: PCT/US2020/025534
§ 371 (c)(1),
(2) Date: Sep. 28, 2021

(87) PCT Pub. No.: WO2020/205660
PCT Pub. Date: Oct. 8, 2020

(65) Prior Publication Data

US 2022/0185792 A1 Jun. 16, 2022
US 2023/0212143 A9 Jul. 6, 2023

Related U.S. Application Data

(60) Provisional application No. 62/826,933, filed on Mar. 29, 2019.

(51) Int. Cl.
*C07D 401/14* (2006.01)
*A61P 35/00* (2006.01)
*C07D 209/86* (2006.01)
*C07D 401/12* (2006.01)
*C07D 403/12* (2006.01)

(52) U.S. Cl.
CPC ......... *C07D 401/14* (2013.01); *C07D 209/86* (2013.01); *C07D 401/12* (2013.01); *C07D 403/12* (2013.01)

(58) Field of Classification Search
CPC .. C07D 401/14; C07D 209/86; C07D 401/12; C07D 403/12; A61P 35/00
See application file for complete search history.

(56) References Cited

U.S. PATENT DOCUMENTS

| | | | | |
|---|---|---|---|---|
| 6,399,631 | B1 * | 6/2002 | Elliott | C07D 401/14 546/175 |
| 8,916,575 | B2 | 12/2014 | McGowan et al. | |
| 9,676,749 | B2 | 6/2017 | Baiocchi et al. | |

(Continued)

OTHER PUBLICATIONS

Wang et al., Protein Arginine Methyltransferase 5 (PRMT5) as an Anticancer Target and Its Inhibitor Discovery, J. Med. Chem., 61, pp. 9429-9441 (Year: 2018).*

(Continued)

*Primary Examiner* — Jeffrey S Lundgren
*Assistant Examiner* — Alexander K. Showalter
(74) *Attorney, Agent, or Firm* — Wolf, Greenfield & Sacks, P.C.

(57) ABSTRACT

A series of PRMT5 inhibitor compounds are described. The compounds are useful as PRMT5 inhibitor compounds and in the treatment of PRMT5 mediated diseases, disorders, and symptoms thereof.

26 Claims, 31 Drawing Sheets

(56) References Cited

U.S. PATENT DOCUMENTS

| | | | | |
|---|---|---|---|---|
| 2011/0009381 | A1* | 1/2011 | Vu | A61P 43/00 544/122 |
| 2016/0046578 | A1 | 2/2016 | Baiocchi et al. | |
| 2018/0098987 | A1 | 4/2018 | Duncan et al. | |
| 2021/0371431 | A1* | 12/2021 | Vadivelu | C07D 471/04 |

OTHER PUBLICATIONS

Petrov et al., Mastering tricyclic ring systems for desirable functional cannabinoid activity, Eur. J. Med. Chem., 69, pp. 881-897 (Year: 2013).*

International Search Report and Written Opinion for PCT/US2020/025534 mailed Aug. 10, 2020.

International Preliminary Report on Patentability for PCT/US2020/025534 mailed Oct. 14, 2021.

Mao et al., Potent, Selective, and Cell Active Protein Arginine Methyltransferase 5 (PRMT5) Inhibitor Developed by Structure-Based Virtual Screening and Hit Optimization. J Med Chem. Jul. 27, 2017;60(14):6289-6304. doi: 10.1021/acs.jmedchem.7b00587. Epub Jul. 12, 2017. PMID: 28650658.

Pubchem CID 18677533. Dec. 4, 2007.

Pubchem CID 21341810. Dec. 5, 2007.

Pubchem CID 593485. Mar. 27, 2005.

Alinari et al., Selective inhibition of protein arginine methyltransferase 5 blocks initiation and maintenance of B-cell transformation. Blood. Apr. 16, 2015;125(16):2530-43. doi: 10.1182/blood-2014-12-619783. Epub Mar. 5, 2015.

Antonysamy et al., Crystal structure of the human PRMT5:MEP50 complex. Proc Natl Acad Sci U S A. Oct. 30, 2012;109(44):17960-5. doi: 10.1073/pnas.1209814109. Epub Oct. 15, 2012.

Beaudet et al., AlphaLISA immunoassays: the no-wash alternative to ELISAs for research and drug discovery. Nature Methods. Dec. 2008;5:an8-9.

Blanc et al., Arginine Methylation: The Coming of Age. Mol Cell. Jan. 5, 2017;65(1):8-24. doi: 10.1016/j.molcel.2016.11.003.

Bonday et al., LLY-283, a Potent and Selective Inhibitor of Arginine Methyltransferase 5, PRMT5, with Antitumor Activity. ACS Med Chem Lett. Apr. 23, 2018;9(7):612-617. doi: 10.1021/acsmedchemlett.8b00014.

Chan-Penebre et al., A selective inhibitor of PRMT5 with in vivo and in vitro potency in MCL models. Nat Chem Biol. Jun. 2015;11(6):432-7. doi: 10.1038/nchembio. 1810. Epub Apr. 27, 2015.

Cinelli et al., Simplified 2-aminoquinoline-based scaffold for potent and selective neuronal nitric oxide synthase inhibition. J Med Chem. Feb. 27, 2014;57(4):1513-30. doi: 10.1021/jm401838x. Epub Feb. 10, 2014.

Fabbrizio et al., Negative regulation of transcription by the type II arginine methyltransferase PRMT5. EMBO Rep. Jul. 2002;3(7):641-5. doi: 10.1093/embo-reports/kvf136.

Hu et al., Small Molecule Inhibitors of Protein Arginine Methyltransferases. Expert Opin Investig Drugs. 2016;25(3):335-58. doi: 10.1517/13543784.2016.1144747. Epub Feb. 16, 2016. Author manuscript, 51 pages.

Kaniskan et al., Recent progress in developing selective inhibitors of protein methyltransferases. Curr Opin Chem Biol. Aug. 2017;39:100-108. doi: 10.1016/j.cbpa.2017.06.013. Epub Jun. 26, 2017. Author manuscript, 15 pages.

Karkhanis et al., Versatility of PRMT5-induced methylation in growth control and development. Trends Biochem Sci. Dec. 2011;36(12):633-41. doi: 10.1016/j.tibs.2011.09.001. Epub Oct. 3, 2011. Author manuscript, 15 pages.

Mavrakis et al., Disordered methionine metabolism in MTAP/CDKN2A-deleted cancers leads to dependence on PRMT5. Science. Mar. 11, 2016;351(6278):1208-13. doi: 10.1126/science.aad5944. Epub Feb. 11, 2016.

Pal et al., Human SWI/SNF-associated PRMT5 methylates histone H3 arginine 8 and negatively regulates expression of ST7 and NM23 tumor suppressor genes. Mol Cell Biol. Nov. 2004;24(21):9630-45. doi: 10.1128/MCB.24.21.9630-9645.2004.

Stopa et al., The PRMT5 arginine methyltransferase: many roles in development, cancer and beyond. Cell Mol Life Sci. Jun. 2015;72(11):2041-59. doi: 10.1007/s00018-015-1847-9. Epub Feb. 7, 2015.

Xu et al., Application of machine learning methods to histone methylation ChIP-Seq data reveals H4R3me2 globally represses gene expression. BMC Bioinformatics. Jul. 23, 2010;11:396. doi: 10.1186/1471-2105-11-396.

* cited by examiner

SAM

SAH

CMP5

1-ET-1F

CMP5

6-1F

Table 1. MCF-7 cell viability of PRMT 5 inhibitors

| COMPOUNDS | CMP5 | 6-1 F | 1-1F | 1-ET-1F | 1-BUT-1F | 3-ET-4F | 4-1F-N | 4-ET-1F | 4-ET-2F | 4-ET-3F | 4-5F | 8-2F | 8-ET-1F | 8-ET-2F | 8-ET-4F |
|---|---|---|---|---|---|---|---|---|---|---|---|---|---|---|---|
| MCF-7 IC50 (μM) | 36.7 | 4.7 | 12.59 | 3.396 | 1.771 | 5.269 | 4.849 | 1.137 | 1.910 | 0.2527 | 1.521 | 8.098 | 9.936 | 3.032 | 0.6417 |

3-ET-4F 4-1F-N

4-ET-1F

4-ET-2F

4-ET-3F 4-5F 8-2F

8-ET-1F

8-ET-2F

8-ET-4F 1
2A
2B
3A
3B
3
4
5
6
7
8
9
1-ET-1F

SAM

SAH

MTA

JNJ-64619178

CMP5
($IC_{50}$ = 386.1 μM)

6-1F
($IC_{50}$ = 83.7 μM)

TO FIG. 15B

LLY-283

EPZ015666

GSK-3326595

1-ET-1F
($IC_{50}$ = 13.26 μM)

1-1F
($IC_{50}$ = 78.3 μM)

1-BUT-1F
($IC_{50}$ = 7.89 μM)

FROM FIG. 15A

| Compound | $IC_{50}$ in MCF-7 (μM) | $IC_{50}$ in MDA-MB-231 (μM) | $IC_{50}$ in MV4-11 (μM) |
|---|---|---|---|
| CMP5 | 36.70 | 50.45 | 24.90 |
| 6-1F | 4.700 | 3.441 | 3.670 |
| 1-1F | 12.59 | 9.974 | 6.616 |
| 1-ET-1F | 3.396 | 2.658 | 2.061 |
| 1-BUT-1F | 1.771 | 2.503 | 0.8253 |

| Compound name | $R_2$ group | Enzymatic $IC_{50}$ (μM) |
| --- | --- | --- |
| 11-1F |  | 1.3 ± 0.2 |
| 11-3F |  | > 500 |
| 11-5F |  | 7.2 ± 0.2 |
| 11-6F |  | > 500 |
| 11-9F |  | 0.2 ± 0.01 |

Data shown are mean ± SD of three replicates.

| Compound name | $R_2$ group | Enzymatic $IC_{50}$ |
|---|---|---|
| GSK-3326959 |  | 5.7 ± 0.3 nM |
| 15-1F |  | 233.8 ± 15.8 nM |
| 15-2F |  | < 150 nM (impure) |
| 15-3F |  | > 100 μM |
| 15-4F |  | > 100 μM |
| 15-5F |  | 29.6 ± 1.3 μM |

Data shown are mean ± SD of three replicates.

| Compound name | Chemical structure | Enzymatic $IC_{50}$ (μM) | Binding affinity $K_D$ (μM) on different receptors | | | |
|---|---|---|---|---|---|---|
| | | | Apo P:M | P:M + MTA | P:M + SAH | P:M + SAM |
| 11-1F |  | 1.3 | 15.7 | 0.256 | 1.67 | 1.32 |
| 11-2F |  | 0.7 | 12.1 | 0.095 | 0.895 | 0.692 |
| 11-3F |  | > 500 | N.B | L.B | N.B | N.B |
| 11-5F |  | 7.2 | N.B | N.B | N.B | 2.84 |
| 11-6F |  | > 500 | N.B | L.B | N.B | N.B |
| 11-9F |  | 0.180 | 4.33 | 0.162 | 0.191 | 0.732 |
| 15-1F |  | 0.234 | 7.32 | 0.038 | 0.218 | 0.106 |
| GSK-3326959 |  | 0.006 | N.B | 5.9 | 0.794 | < 0.1 |

L.B.: very low binding response; N.B.: no binding

PRMT5 INHIBITOR COMPOUNDS

CROSS-REFERENCE TO RELATED APPLICATIONS

This Application is a national stage filing under 35 U.S.C. § 371 of International Patent Application Serial No. PCT/US2020/025534, filed Mar. 27, 2020, which claims priority under 35 USC § 119(e) to U.S. Provisional Application No. 62/826,933, filed Mar. 29, 2019. The entire contents of this application is incorporated herein by reference in its entirety.

STATEMENT OF RIGHTS TO INVENTIONS MADE UNDER FEDERALLY SPONSORED RESEARCH

This invention was made with government support under Grant No. CA212403 awarded by the National Institutes of Health. The government has certain rights in the invention.

BACKGROUND

Protein arginine methyltransferase 5 (PRMT5), the major type II arginine methyltransferase, has been reported to have a series of bioactive functions during multiple cellular processes including tumorigenesis. Although the mechanism of PRMT5 related to tumorigenesis is still unclear, S-adenosylmethionine (SAM), as the co-factor of PRMT5, plays essential roles in the processes of methylating a variety of cytoplasmic and nuclear substrates that are involved in tumorigenesis. Typically, there are two types of PRMT 5 inhibitors according to their binding sites. One targets the enzyme substrate site, whose binding is dependent of SAM or SAM analogues' binding, such as EPZ015666; the other targets co-factor site, such as LLY-283, which binds directly to SAM pocket and the majority of inhibitors in this type are nucleoside based.

Arginine methylation of proteins, as an important class of post-translational modification, plays a crucial function in a variety of cellular pathways including cell growth and proliferation, apoptosis, angiogenesis, and metastasis by regulating both transcriptional and post-transcriptional RNA processing.[1] This modification is catalyzed by the protein arginine methyltransferase (PRMT), which transfers a methyl group from S-adenosylmethionine (SAM) to the terminal guanidino nitrogen atoms of arginine side-chains of histone and nonhistone proteins. So far nine human PRMTs have been reported and divided into type I, type II, and type III enzymes on the basis of specific kind of arginine methylation catalyzed. PRMT5 is the major type II PRMT which catalyzes the formation of ω-NG-monomethyl and ω-NG, N'G-symmetric dimethyl arginine residues. In the nucleus, PRMT5 has been shown to be involved in transcriptional repression including that of tumor suppressor and cell cycle genes like ST7 (suppressor of tumorigenicity 7 protein),[2] cyclin E1 and CDKN2A (cyclin-dependent kinase inhibitor 2A).[3] These epigenetic modifications are catalyzed by PRMT5 through the symmetric dimethylation of histone H4 on the R3 residue (H4R3me2s) and on the R8 residue of histone H3 (H3R8me2s). H4R3me2s is generally associated with transcriptional repression,[4] while H3R8me2s is seen as a mark for both transcriptional activation and repression.[5] In the past decade, PRMT5 has attracted increasing attention as an anticancer target. It is overexpressed in various cancers, including lymphoma, prostate cancer, glioblastoma, and colorectal carcinoma and is associated with poor prognosis.[6] Although Several small molecule inhibitors of PRMT5 have been reported,[7-9] most of these are low potency inhibitors or lack cellular and/or in vivo activity. Typically, there are two types of PRMT 5 inhibitors according to their binding sites. One targets the enzyme substrate site, whose binding is dependent of SAM or SAM analogues' binding, such as EPZ015666;[10] the another targets co-factor site, such as LLY-283,[11] which binds directly to SAM pocket and the majority of inhibitors in this type are nucleoside based. Here we describe a series of indole-based SAM competitive PRMT5 inhibitor compounds optimized from the lead compound (CMP5).[12] The binding affinity and efficacy have been increased on the order of about 25-fold and 40-fold, respectively. Furthermore, the MTT assay shows that our compounds are effective in the MCF-7 cell line.

BRIEF SUMMARY OF THE INVENTION

This invention is directed towards compounds, compositions, and methods of treating disease, disorders and conditions in a subject, including, inflammation, cancer, and autoimmune diseases by use of the compounds and compositions thereof.

It is understood that the embodiments of the invention discussed below with respect to the preferred variable selections can be taken alone or in combination with one or more embodiments, or preferred variable selections, of the invention, as if each combination were explicitly listed herein.

In one aspect, the invention is directed to a compound of Formula (I) or (II), or a pharmaceutically acceptable salt, solvate, hydrate or prodrug thereof:

(I)

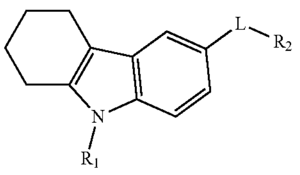

(II)

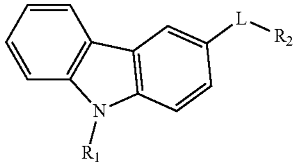

wherein each $R_1$ is independently optionally substituted alkyl, optionally substituted cycloalkyl, optionally substituted heterocycloalkyl, optionally substituted cycloalkylalkyl, optionally substituted heterocycloalkylalkyl, or optionally substituted hydroxyalkyl;

each L is independently

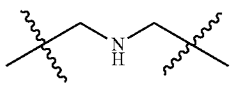

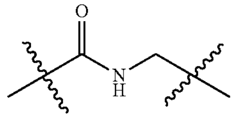

or

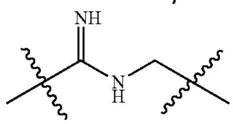

;

and each $R_2$ is independently optionally substituted aryl, optionally substituted heteroaryl, optionally substituted —C(O)—NH-aryl, or optionally substituted —C(O)-heterocycloalkyl.

In one aspect, the invention is directed to a compound of Formula (I) or (II), or a pharmaceutically acceptable salt, solvate, hydrate or prodrug thereof:

(I)

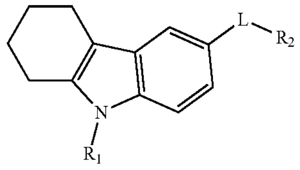

(II)

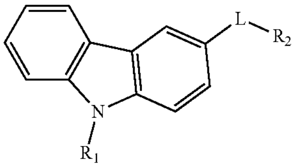

wherein each $R_1$ is independently

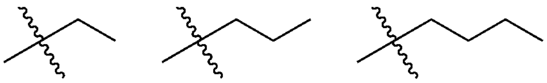
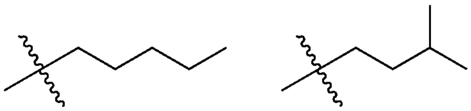
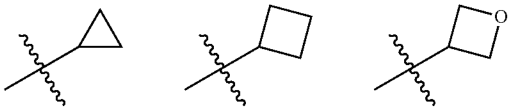
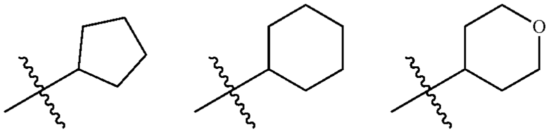
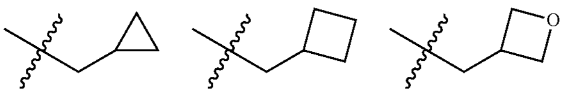
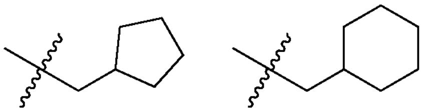
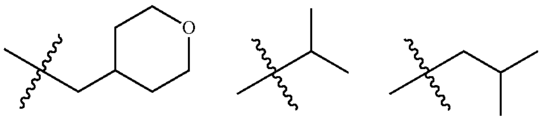

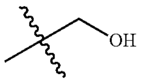 or 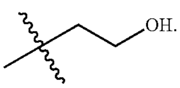

each L is independently

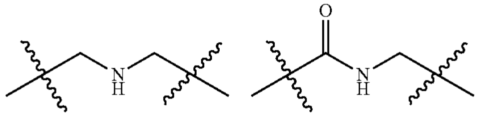 or

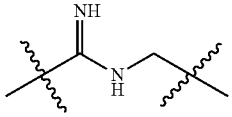

each $R_2$ is independently

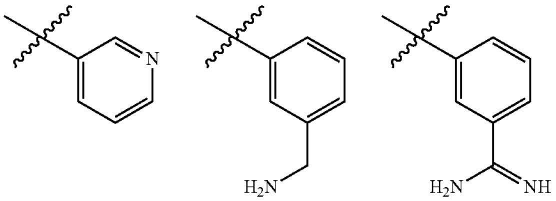
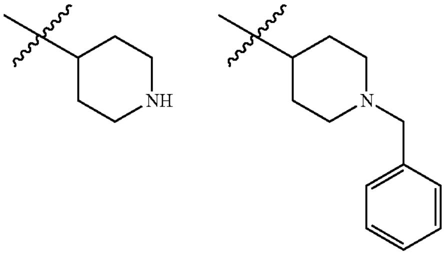
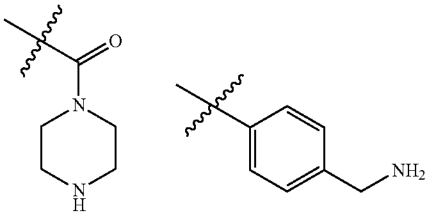
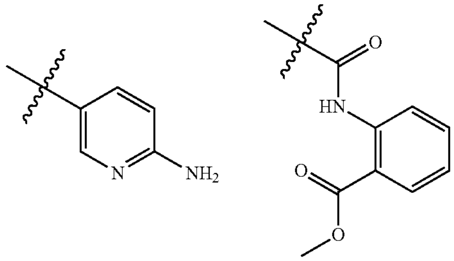
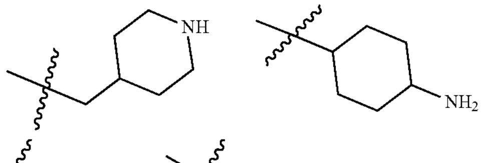
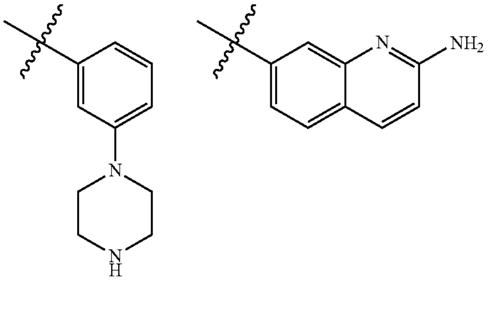

or

-continued
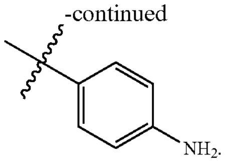
In another aspect, the compound of Formula (I) or (II), is any of
8-1F
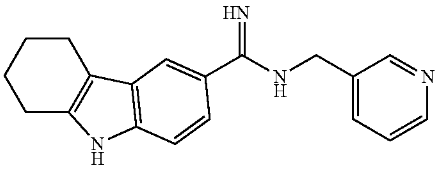
8-2F
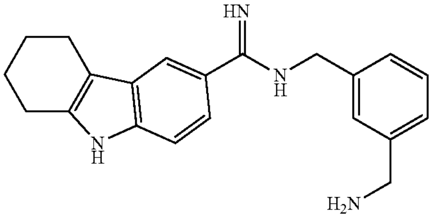
8-3F
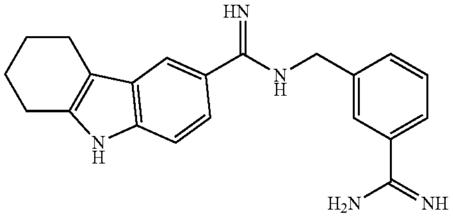
8-ET-1F
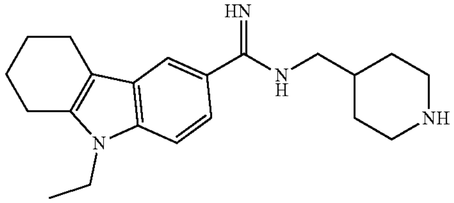
8-ET-2F
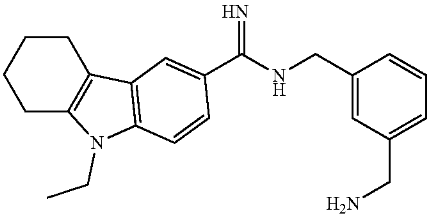
8-ET-4F
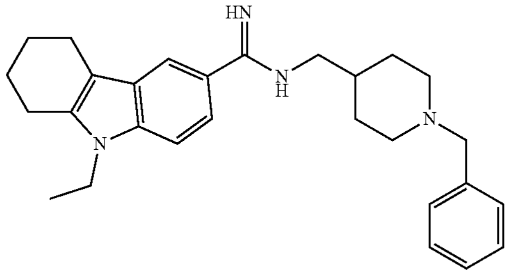
-continued
4-1F
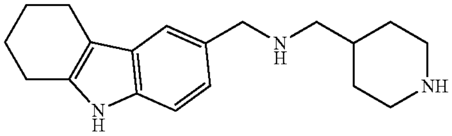
4-2F
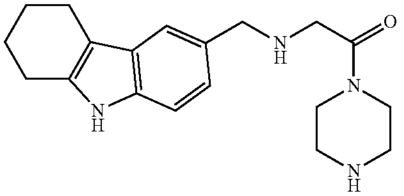
4-3F
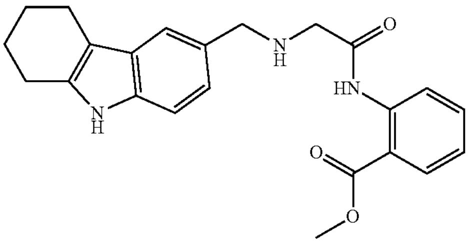
4-5F
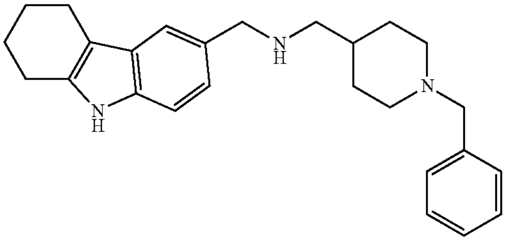
4-ET-1F
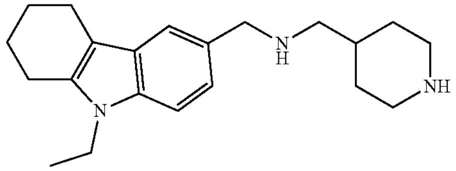
4-ET-2F
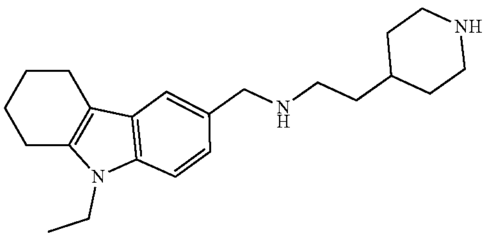
4-ET-3F
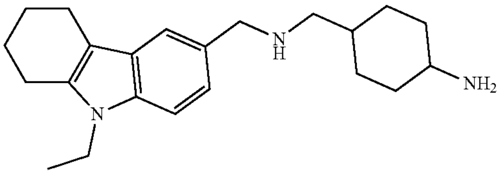

-continued
3-3F
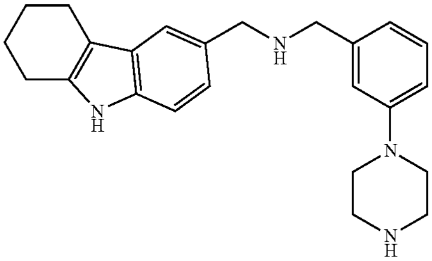
3-4F
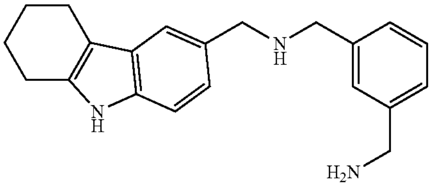
3-ET-4F
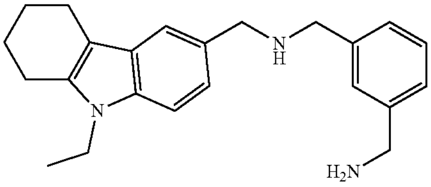
1-ET-1F
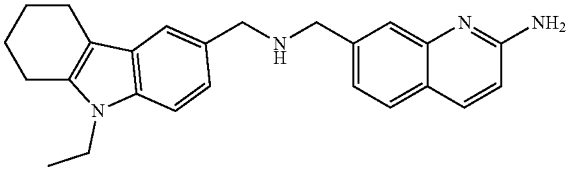
9-1F
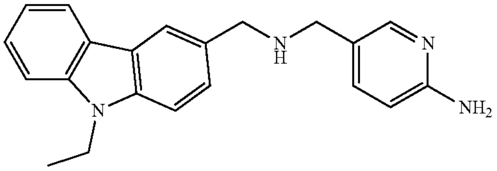
9-2F
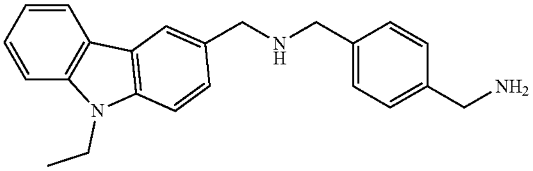
9-5F
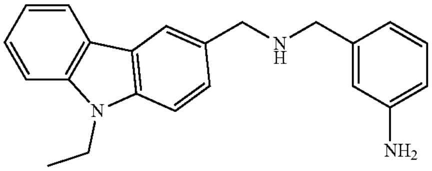
9-6F
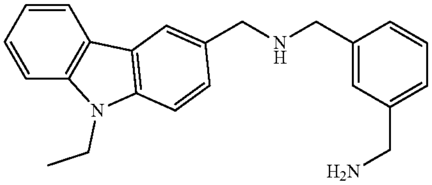
-continued
6-1F
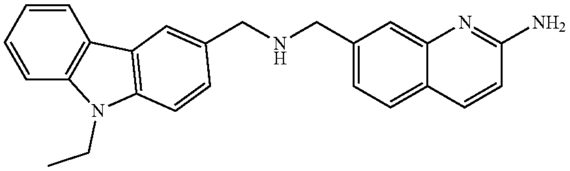
6-2F
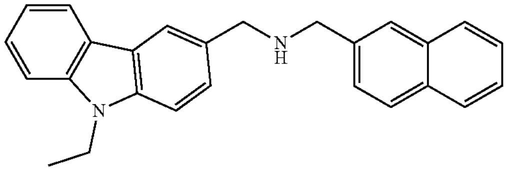
1-1F
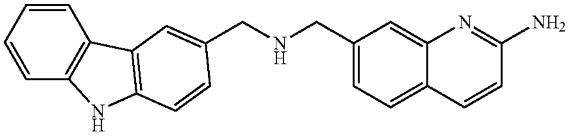
1-ET-1F
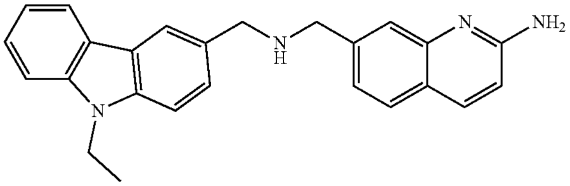
1-BUT-1F
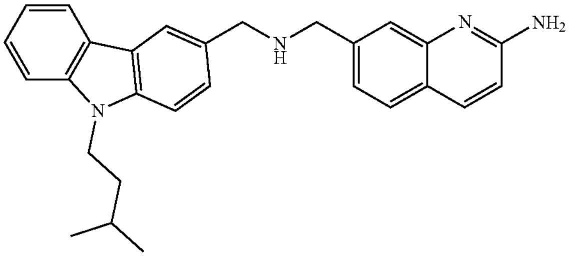
5-1F
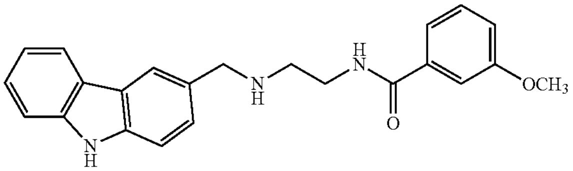
5-3F
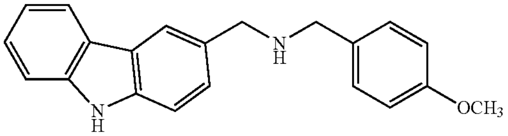
5-4F
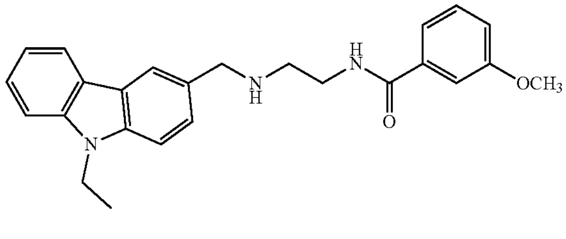

-continued 5-5F

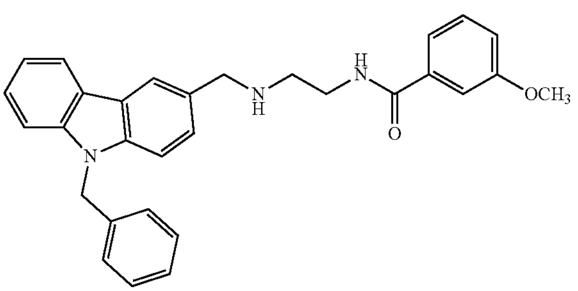

or a pharmaceutically acceptable salt, solvate, hydrate or prodrug thereof.

In another aspect, the invention is directed to a compound of Formula (III), or a pharmaceutically acceptable salt, solvate, hydrate or prodrug thereof:

Formula III

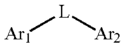

wherein, $Ar_1$ is a monocyclic or bicyclic aromatic ring having 0-4 heteroatoms independently selected from nitrogen, oxygen, and sulfur, wherein $Ar_1$ is substituted with 0, 1, 2, 3, 4, or 5 $R_Y$ groups, as valency permits; each $R_Y$ is independently selected from the group consisting of halo, —CN, —$NO_2$, optionally substituted aliphatic, optionally substituted carbocyclyl, optionally substituted aryl, optionally substituted heterocyclyl, optionally substituted heteroaryl, —$OR^A$, —$N(R^B)_2$, —$SR^A$, —C(═O)$R^A$, —C(O)$OR^A$, —C(O)$SR^A$, —C(O)$N(R^B)_2$, —C(O)$N(R^B)N(R^B)_2$, —OC(O)$R^A$, —OC(O)$N(R^B)_2$, —$NR^B$C(O)$R^A$, —$NR^B$C(O)$N(R^B)_2$, —$NR^B$C(O)$N(R^B)N(R^B)_2$, —$NR^B$C(O)$OR^A$, —SC(O)$R^A$, —C(═$NR^B$)$R^A$, —C(═$NNR^B$)$R^A$, —C(═NORA)$R^A$, —C(═$NR^B$)$N(R^B)_2$, —$NR^B$C(═$NR^B$)$R^B$, —C(═S)$R^A$, —C(═S)$N(R^B)_2$, —$NR^B$C(═S)$R^A$, —S(O)$R^A$, —$OS(O)_2R^A$, —$SO_2R^A$, —$NR^BSO_2R^A$, or —$SO_2N(R^B)_2$;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring, which may be optionally substituted with 0, 1, 2, 3, 4, or 5 $R^x$ groups;

each $R^A$ and $R^B$ can be optionally substituted by one or more independent $R_5$, $R_6$, $R_7$, and $R_8$;

each $R_5$, $R_6$, $R_7$, and $R_8$ is independently hydrogen, halo, or optionally substituted aliphatic;

each $R^x$ is independently selected from the group consisting of halo, —CN, optionally substituted aliphatic, —OR', and —$N(R'')_2$;

each R' is independently hydrogen or optionally substituted aliphatic;

each R'' is independently hydrogen or optionally substituted aliphatic, or two R'' are taken together with their intervening atoms to form a heterocyclic ring; and n is 0, 1, 2, 3, 4, 5, 6, 7, 8, 9, or 10, as valency permits;

L is

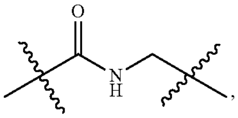
,
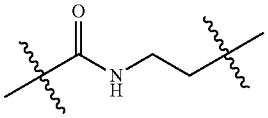
,
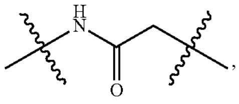
, or
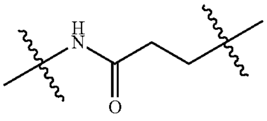
;

and $Ar_2$ is any one of the following groups:

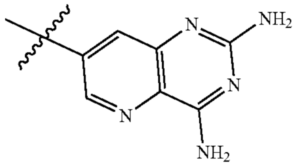

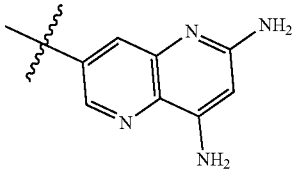

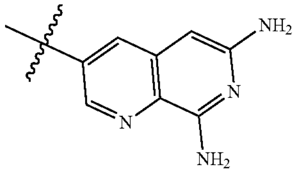

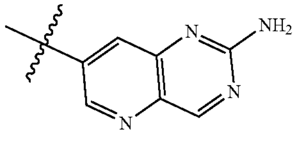

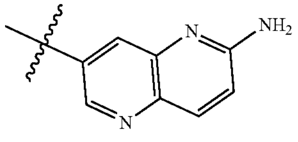

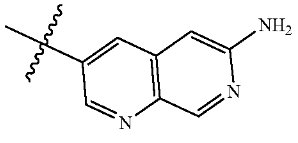

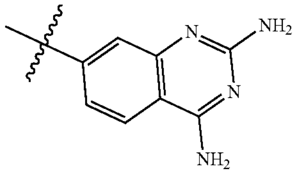

-continued
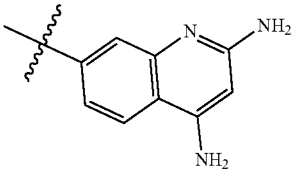
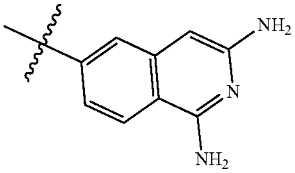
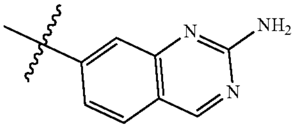
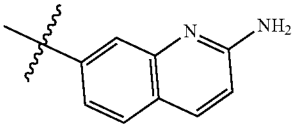
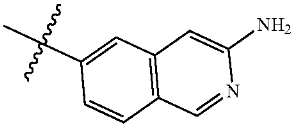
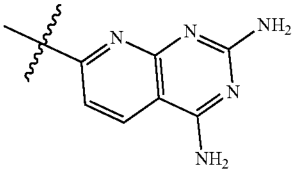
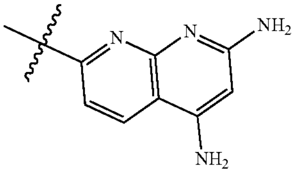
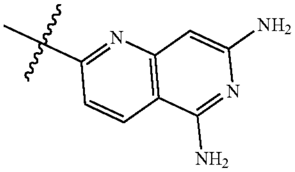
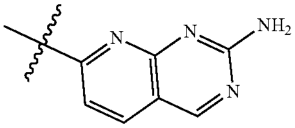
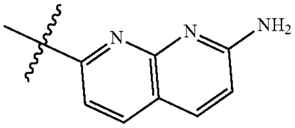
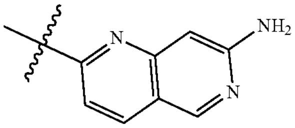
-continued
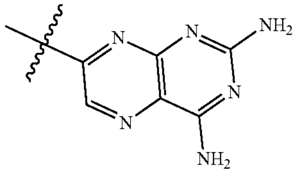
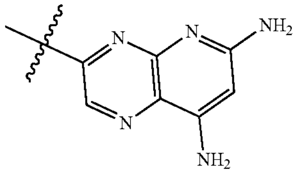
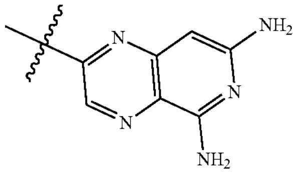
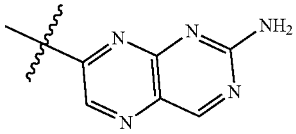
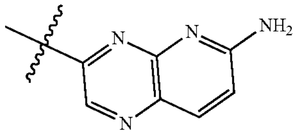
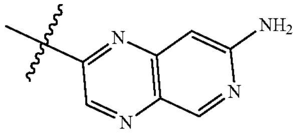
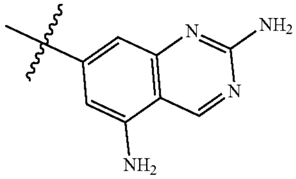
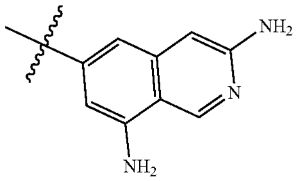
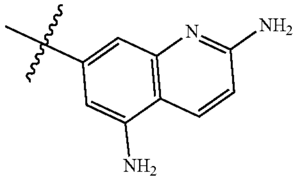
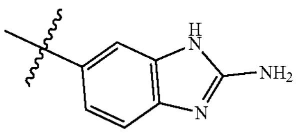
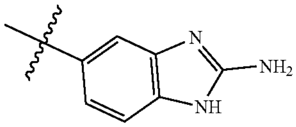

-continued
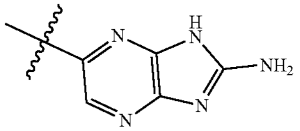
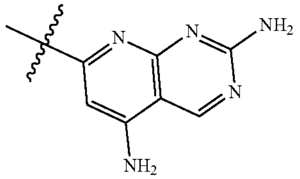
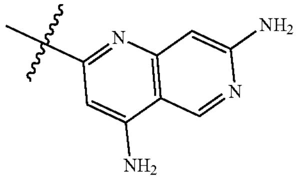
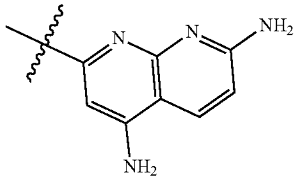
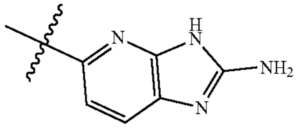
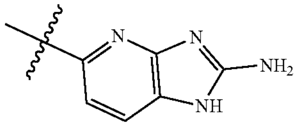
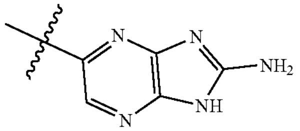
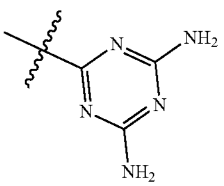
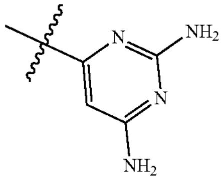
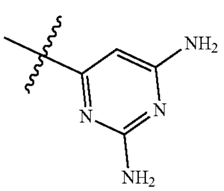
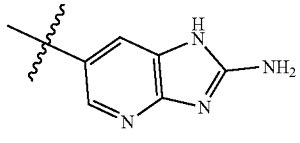
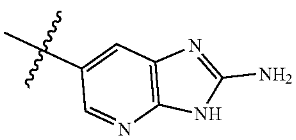
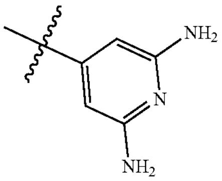
-continued
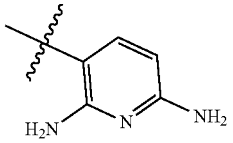
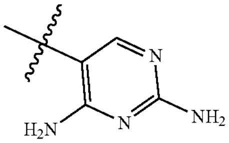
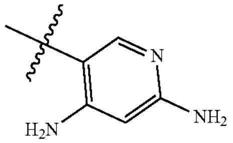
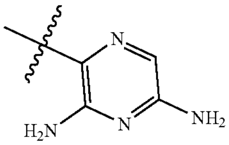
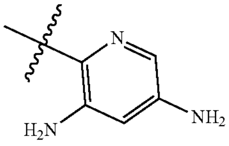
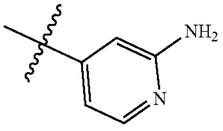
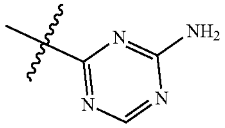
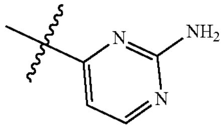
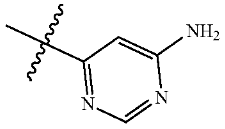
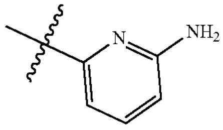
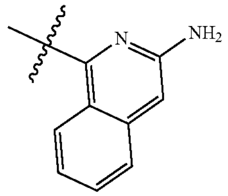
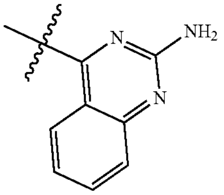
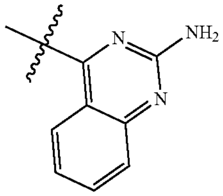
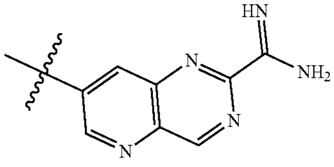
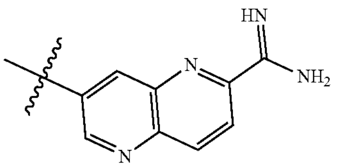
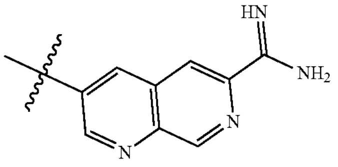

-continued
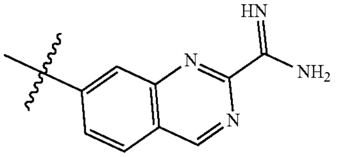
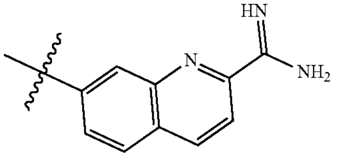
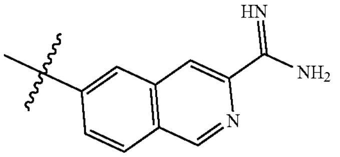
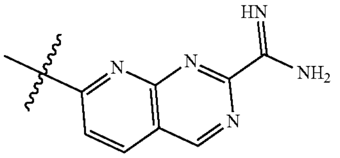
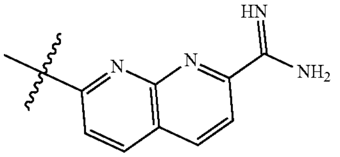
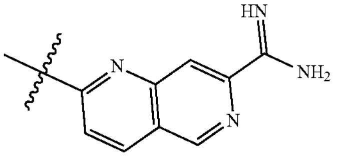
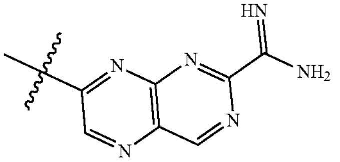
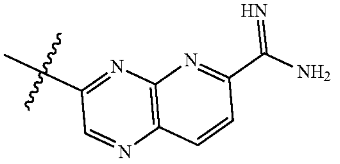
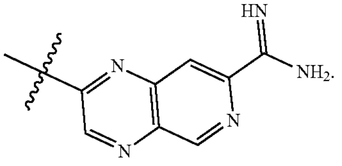
In another aspect, the compounds of Formula III, or a pharmaceutically acceptable salt, solvate, hydrate or prodrug thereof, are those wherein:
$Ar_1$ is any one of the following groups,
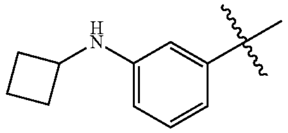
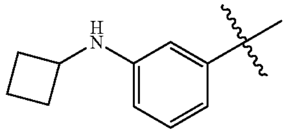
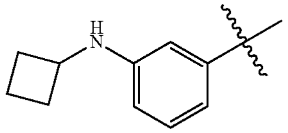
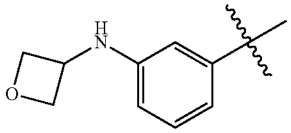
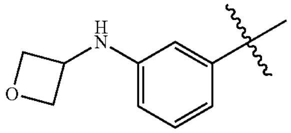
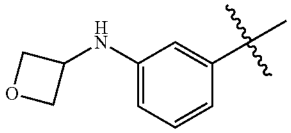
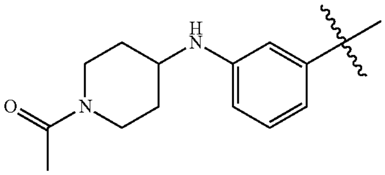
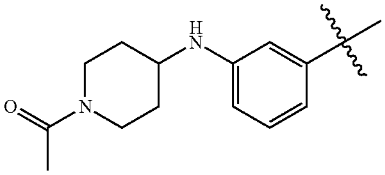
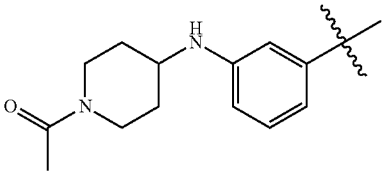
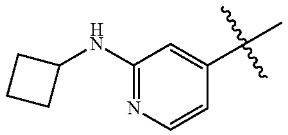
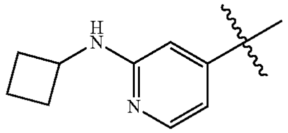

-continued
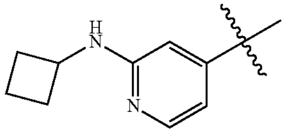
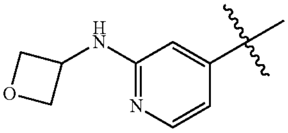
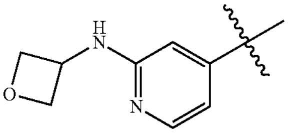
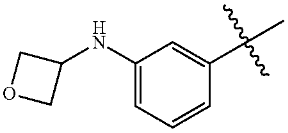
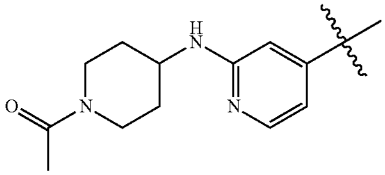
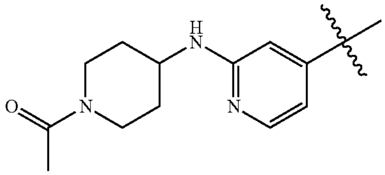
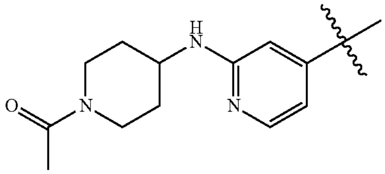
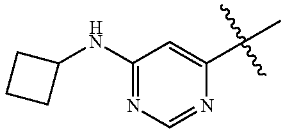
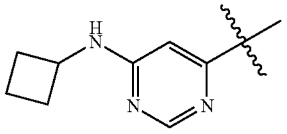
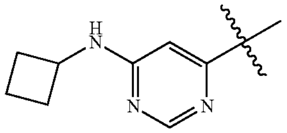
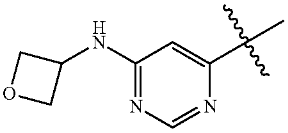
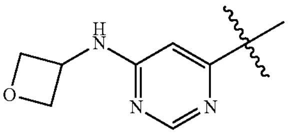
-continued
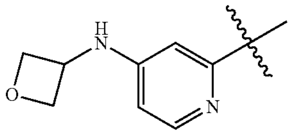
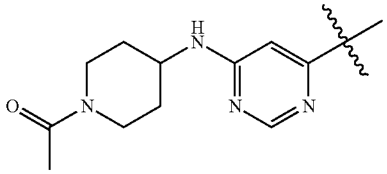
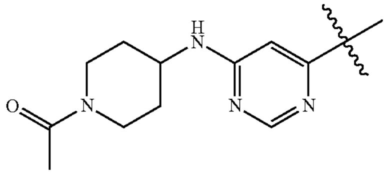
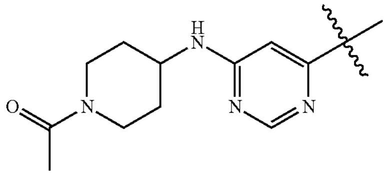
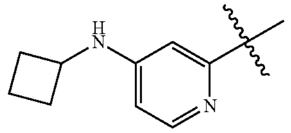
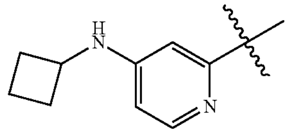
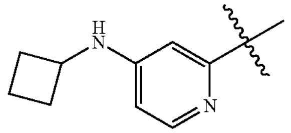
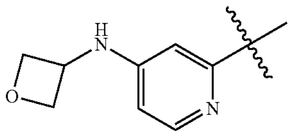
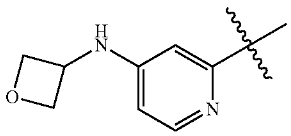
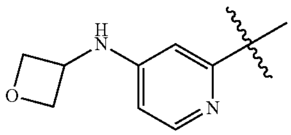
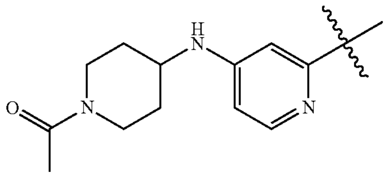

-continued

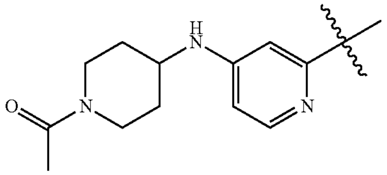

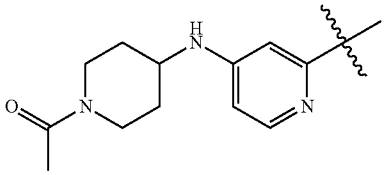

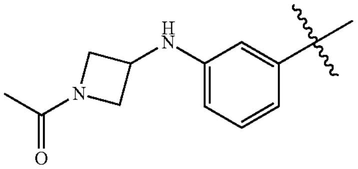

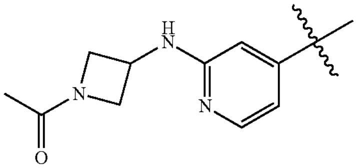

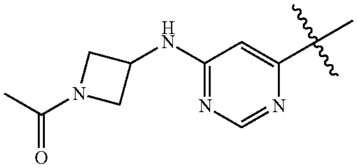

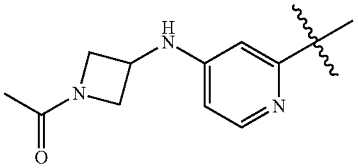

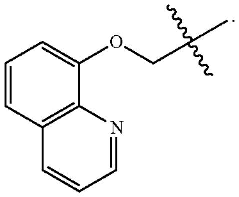 [SMILES: *COc1cccc2cccnc12]

In another aspect, the compounds of Formula III, or a pharmaceutically acceptable salt, solvate, hydrate or prodrug thereof, is one of the following:

15-1F

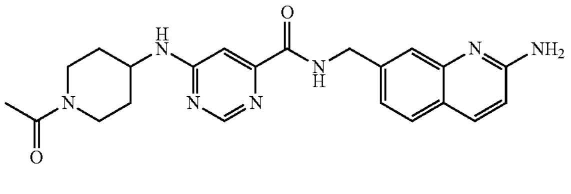

-continued 15-2F

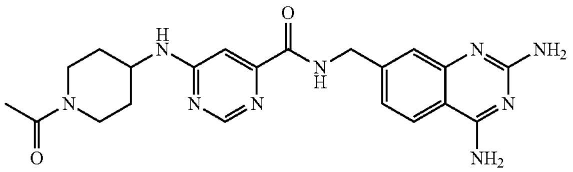

15-8F

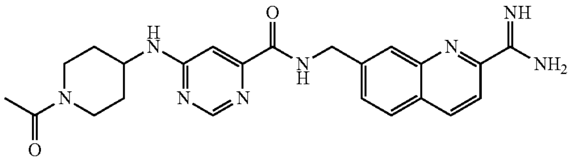

or a pharmaceutically acceptable salt, solvate, hydrate or prodrug thereof.

In another aspect, the invention provides compounds, or a pharmaceutically acceptable salt, solvate, hydrate or prodrug thereof, represented by Formula (IV) or (V):

Formula IV

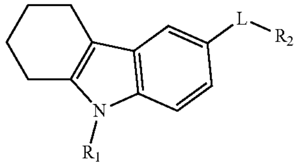

Formula V

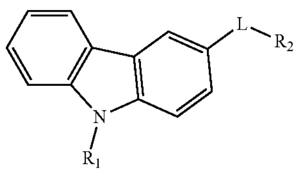

wherein each $R_1$ is independently one of:

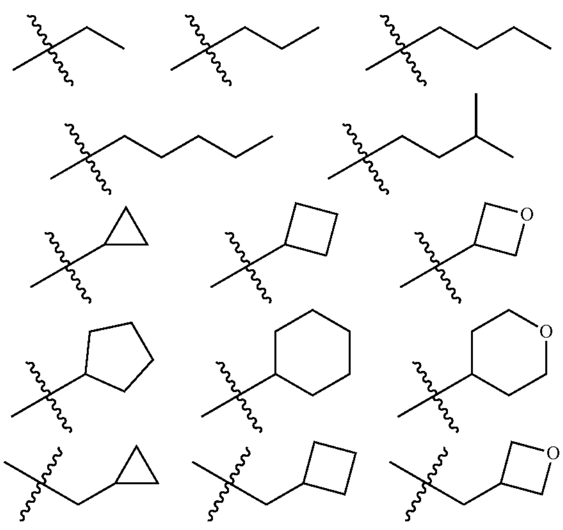

-continued
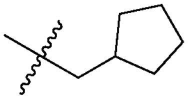
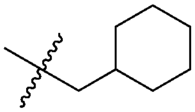
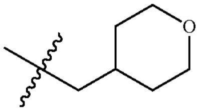
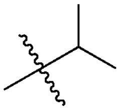
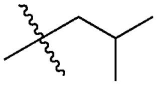
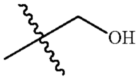
or
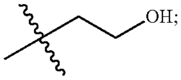
Each L is independently:
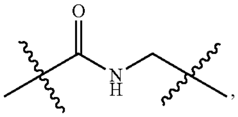
,
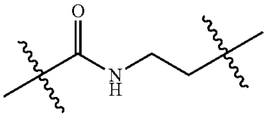
,
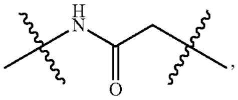
, or
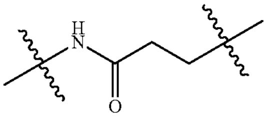
;
Each $R_2$ is independently one of:
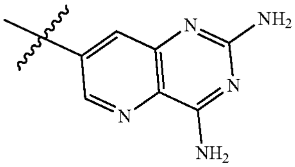
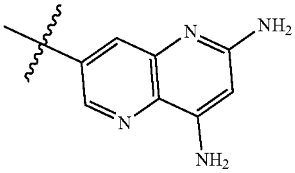
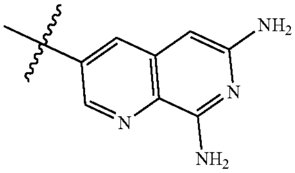
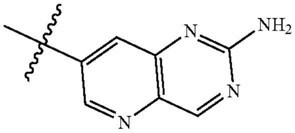
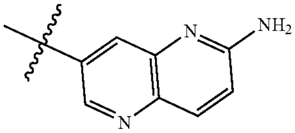
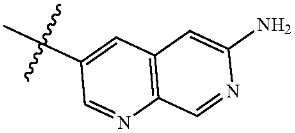
-continued
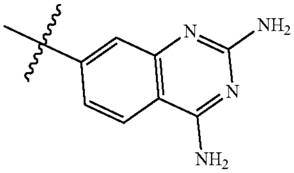
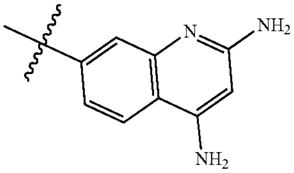
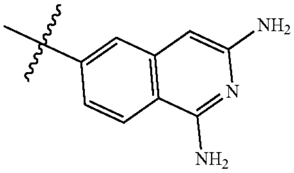
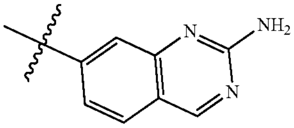
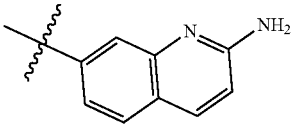
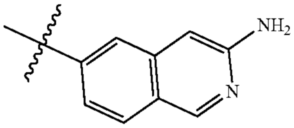
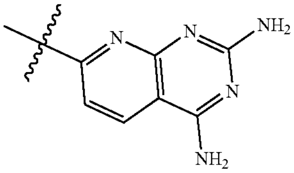
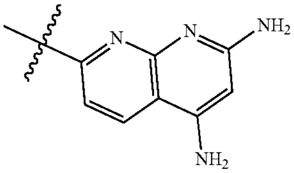
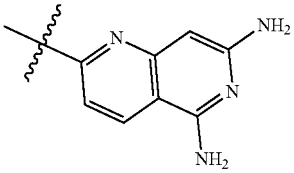
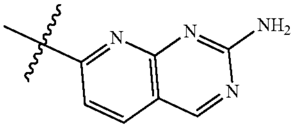
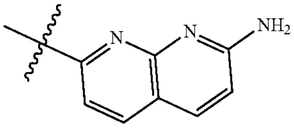

-continued
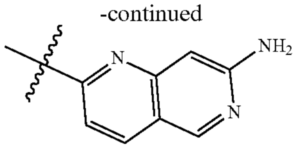
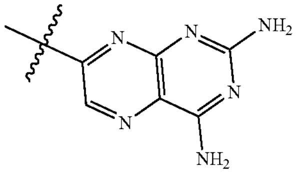
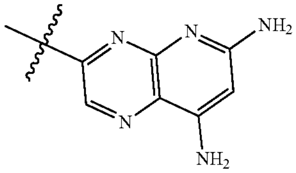
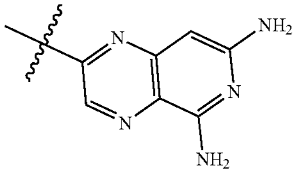
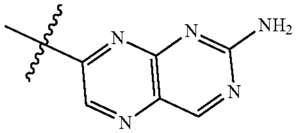
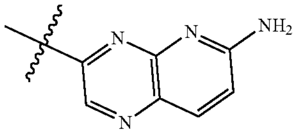
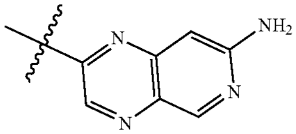
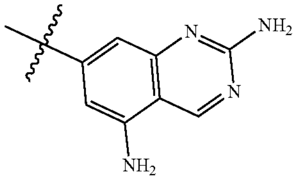
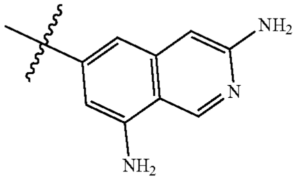
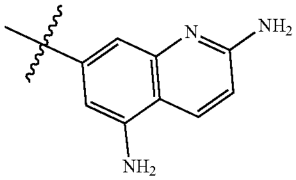
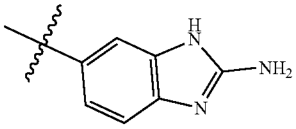
-continued
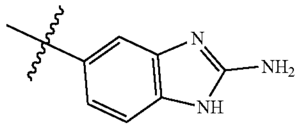
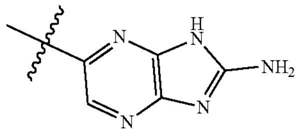
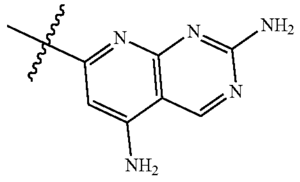
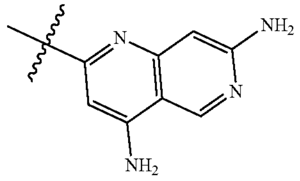
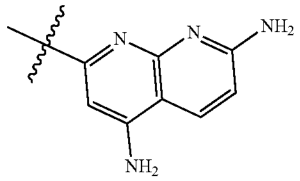
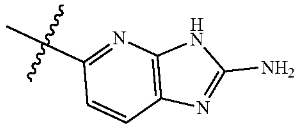
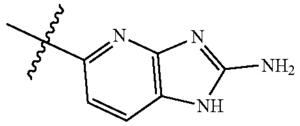
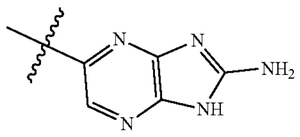
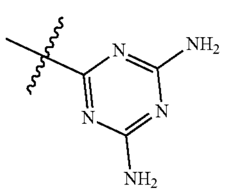
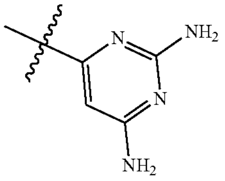
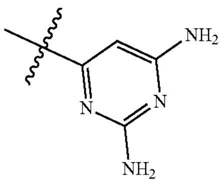
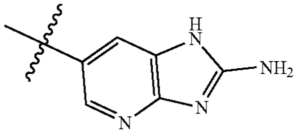

-continued
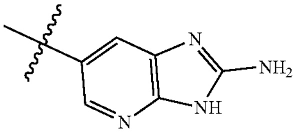
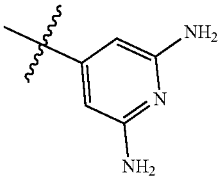
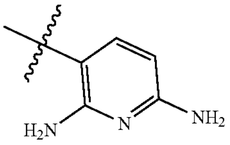
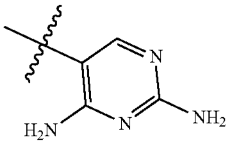
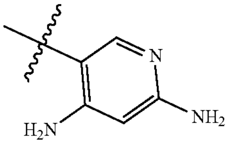
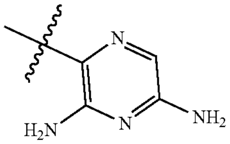
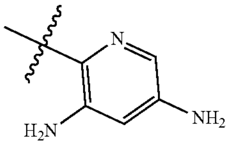
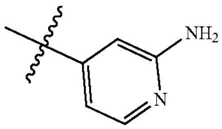
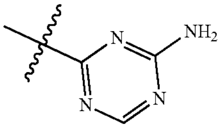
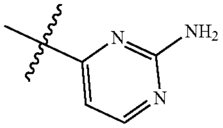
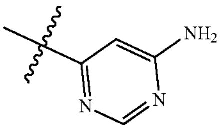
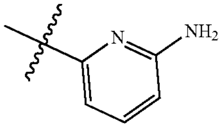
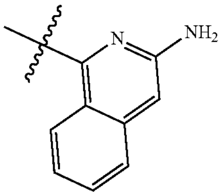
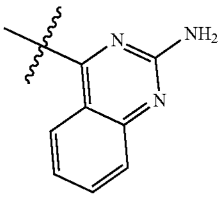
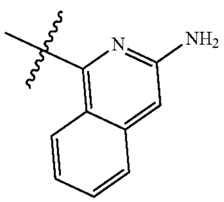
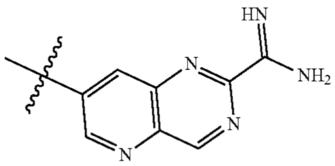
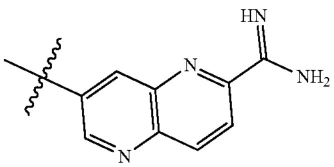
-continued
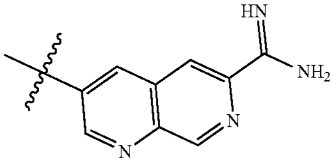
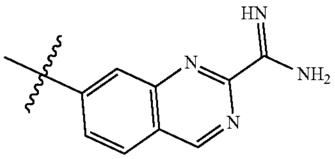
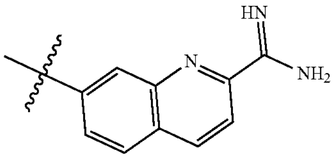
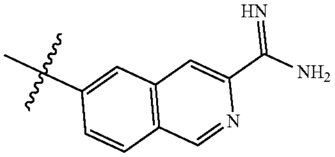
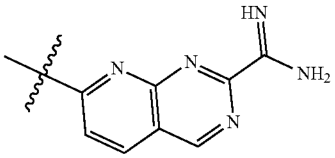
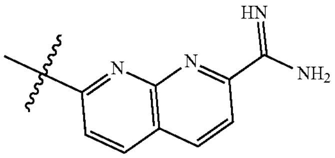
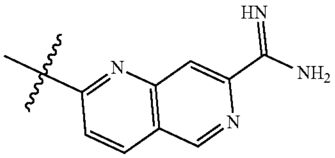
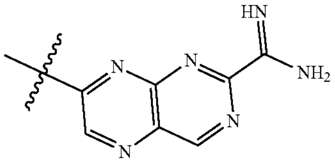
and
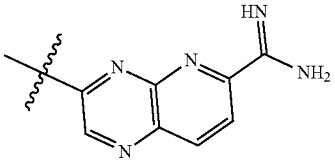
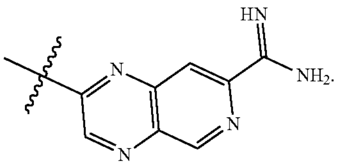
In another aspect, the compound, or a pharmaceutically acceptable salt, solvate, hydrate or prodrug thereof, is any of:

11-1F

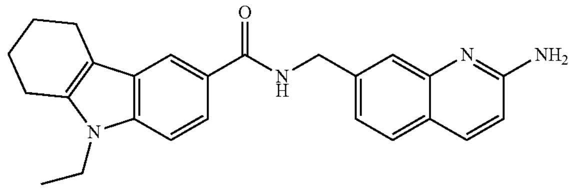

11-2F

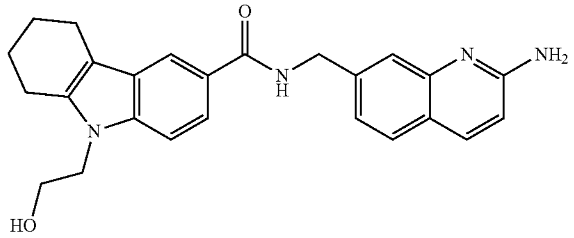

11-9F

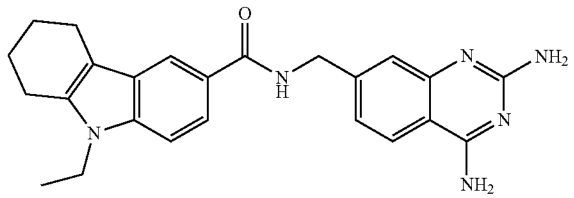

11-10F

•HCl

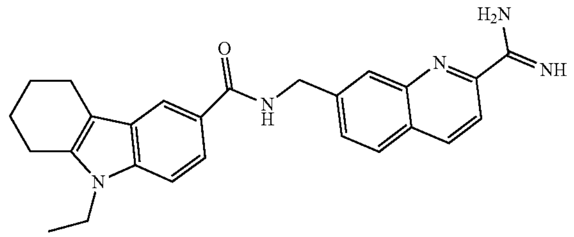

or a pharmaceutically acceptable salt, solvate, hydrate or prodrug thereof.

In another aspect, the invention provides a pharmaceutical composition comprising the compound of any of the formulae herein (e.g., formulae (I)-(II), formulae (I)-(V)), or a pharmaceutically acceptable salt, solvate, hydrate or prodrug thereof, and a pharmaceutically acceptable carrier. In another aspect, the pharmaceutical composition further comprises an additional therapeutic agent (e.g., an anticancer agent).

In other aspects, the invention provides a method of treating a disease, disorder, or symptom thereof in a subject, comprising administering to the subject any compound or composition delineated herein. In another aspect, the compound or composition is administered in an amount and under conditions sufficient to ameliorate the disease, disorder, or symptom thereof in a subject.

In other aspects, the invention provides a method of treating a subject suffering from or susceptible to a proliferative disease, the method comprising administering to the subject a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof.

In other aspects, the invention provides a method of treating a proliferative disease in a subject identified as in need thereof, the method comprising administering to the subject a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof.

In other aspects, the invention provides a method of treating a subject suffering from or susceptible to a proliferative disease, the method comprising administering to the subject a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof, such that said subject is treated for said proliferative disease.

In other aspects, the invention provides a method of treating a proliferative disease in a subject identified as in need thereof, the method comprising administering to the subject a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof, such that said subject is treated for said proliferative disease.

In other aspects, the invention provides a method of modulating the proliferation activity in a subject, comprising contacting the subject with a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof, in an amount and under conditions sufficient to modulate proliferation activity.

In one aspect, the invention provides a method of treating a subject suffering from or susceptible to a proliferation related disorder or disease, comprising administering to the subject a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof.

In another aspect, the invention provides a method of treating a subject suffering from or susceptible to a proliferation related activity related disorder or disease, wherein the subject has been identified as in need of treatment for a proliferation related disorder or disease, comprising administering to said subject in need thereof, a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof, such that said subject is treated for said disorder.

In another aspect, the invention provides a method of treating a subject suffering from or susceptible to a cell proliferation related disorder or disease, wherein the subject has been identified as in need of treatment for a cell proliferation related disorder or disease, comprising administering to said subject in need thereof, a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof, such that cell proliferation in said subject is modulated (e.g., down regulated). In another aspect, the compounds or compositions delineated herein preferentially target cancer cells over nontransformed cells.

In another aspect, the proliferative disease is cancer.

In another aspect, the cancer is multiple myeloma, lymphoma, chronic lymphocytic leukemia (CLL), acute myelogenous leukemia (AML), large granular lymphocyte leukemia (LGL), sarcoma, lung cancer, breast cancer, renal cancer, prostate cancer, pancreatic cancer, melanoma, colon carcinoma, gastric carcinoma, cervical cancer, ovarian cancer, liver cancer, or head and neck cancer.

In a specific aspect, the invention provides a method of treating cancer, tumor growth, cancer of the colon, breast, bone, brain and others (e.g., osteosarcoma, neuroblastoma, colon adenocarcinoma), comprising administering to said subject in need thereof, an effective amount of any compound delineated herein, or a pharmaceutically acceptable salt thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma).

In certain aspects, the disorder of uncontrolled cellular proliferation is cancer. In a further aspect, the cancer is selected from prostate cancer, lung cancer, colon cancer, pancreatic cancer, head & neck cancer, skin cancer, brain cancer, breast cancer, testicular cancer, and ovarian cancer. In a further aspect, the cancer is selected from melanoma, glioma, lymphoma, and leukemia.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

BRIEF DESCRIPTION OF THE DRAWINGS

The present invention is further described below with reference to the following non-limiting examples and with reference to the following figures, in which.

DETAILED DESCRIPTION

Definitions

Figure 1A:
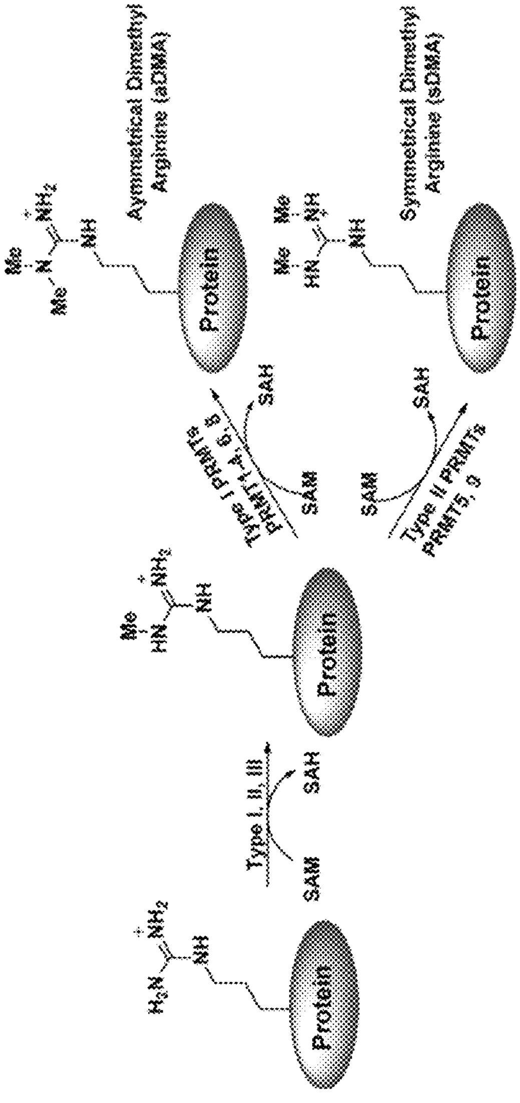
FIG. 1. depicts (A) Arginine methylation reaction catalyzed by three types of PRMTs. (B) Chemical structures of SAM and SAH.[13]
Figure 1B:
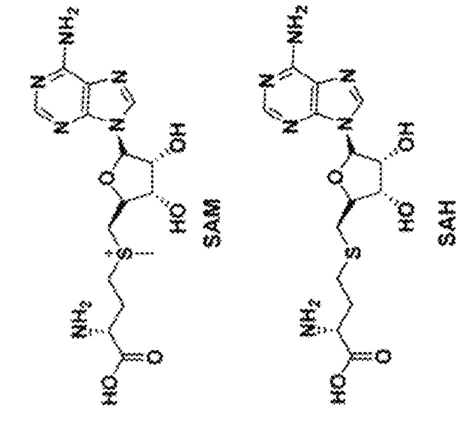
Figure 2:
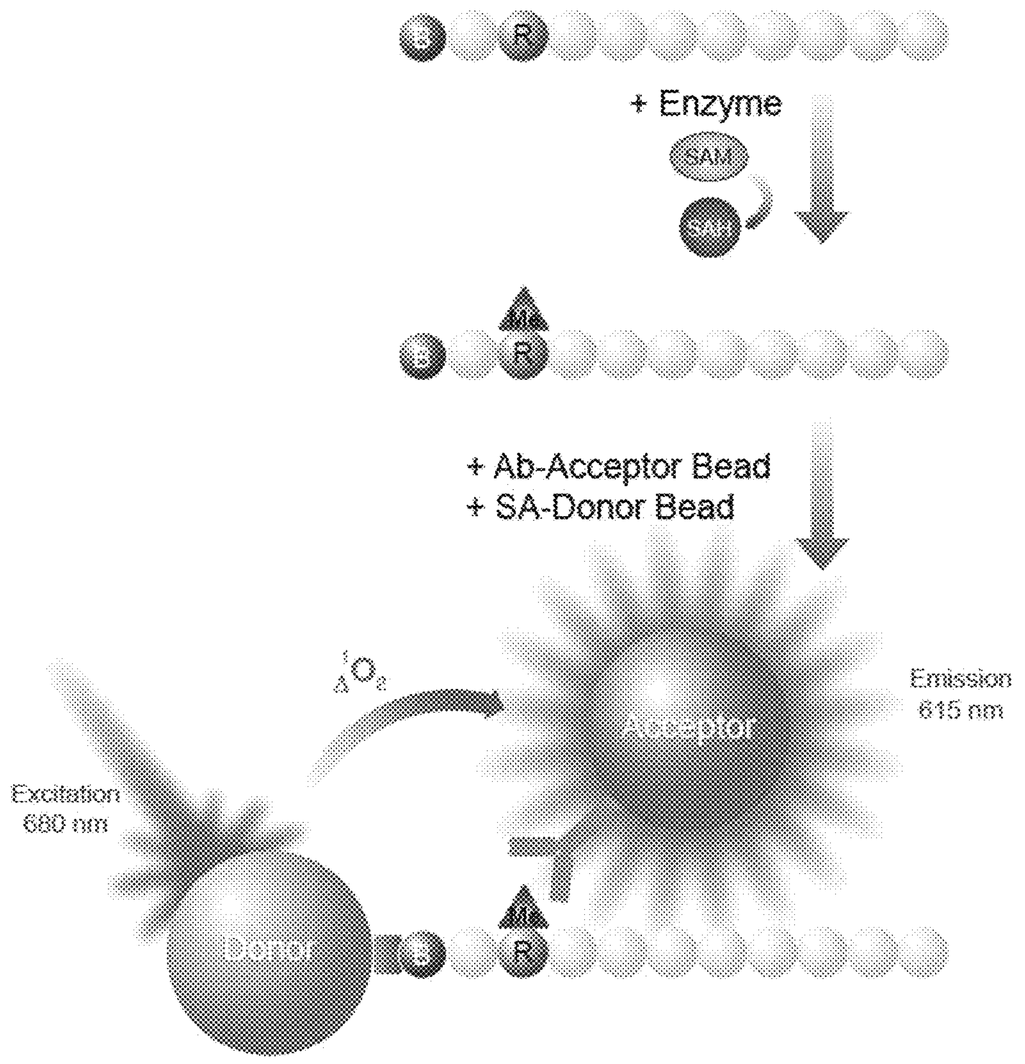
FIG. 2. depicts schematic representation of the AlphaLISA detection of a methylated histone peptide. (B: biotin group; R: arginine residue; Me: methyl group)[14].
Figure 3:
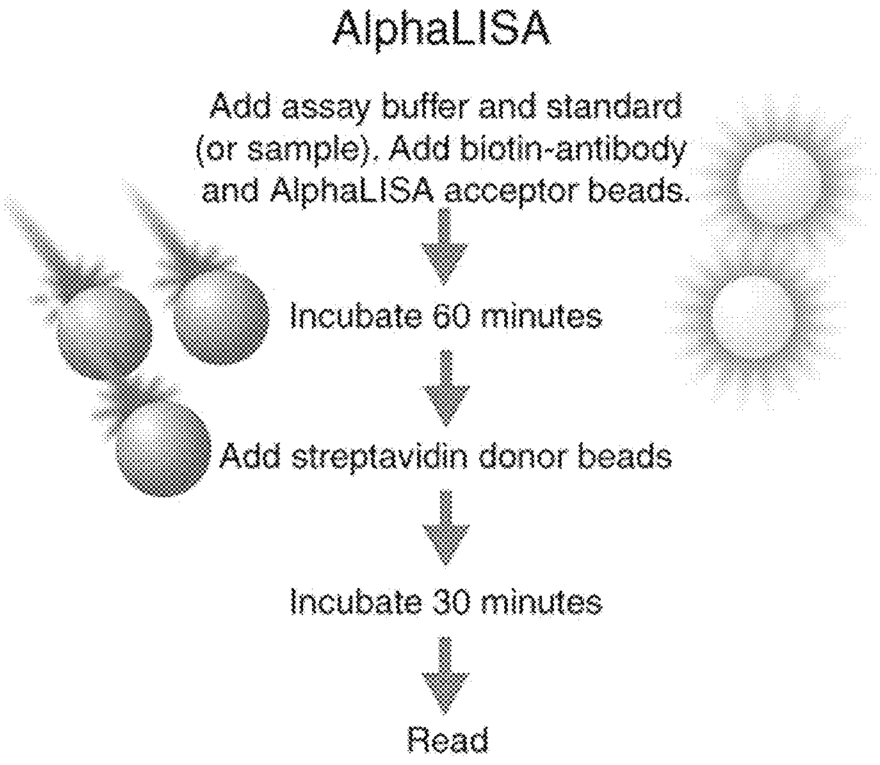
FIG. 3. depicts AlphaLISA assay protocol.[14]
Figure 4:
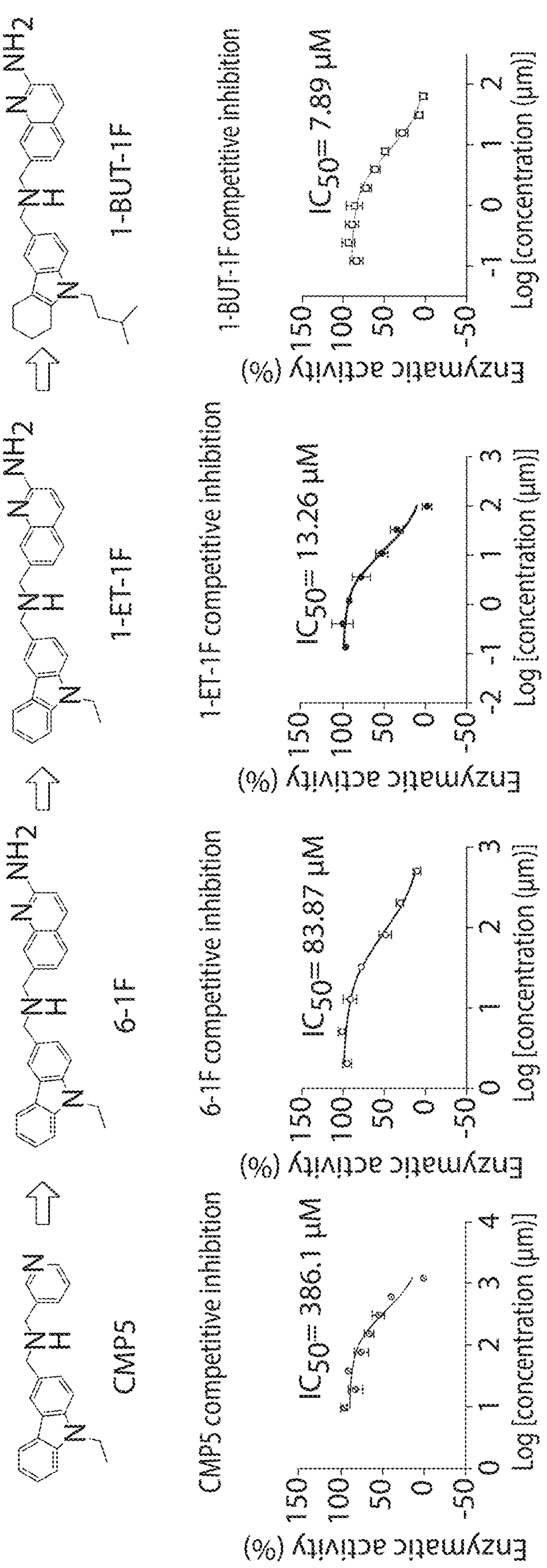
FIG. 4. depicts lead optimization of compounds of the invention based on enzymatic assay.
Figure 5:
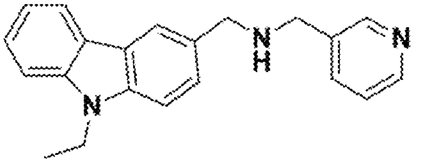
FIG. 5. depicts the proposed binding poses of CMP 5 bound to PRMT 5.
Figure 5:
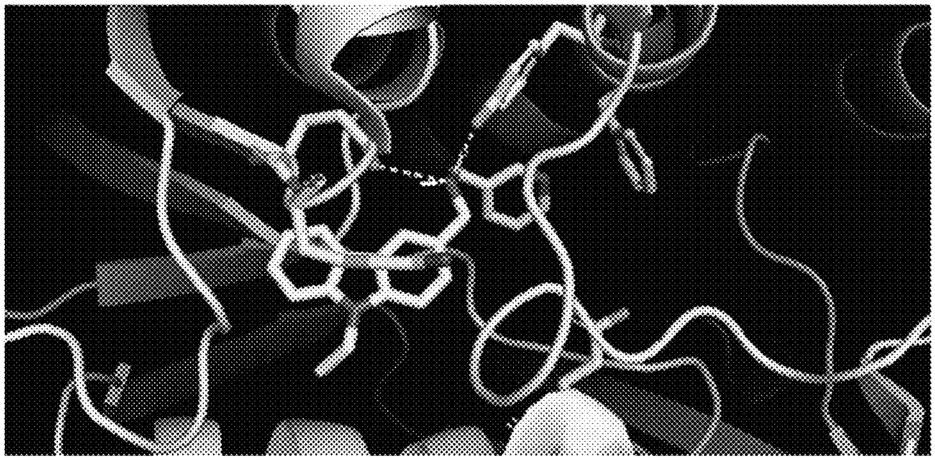
Figure 6:
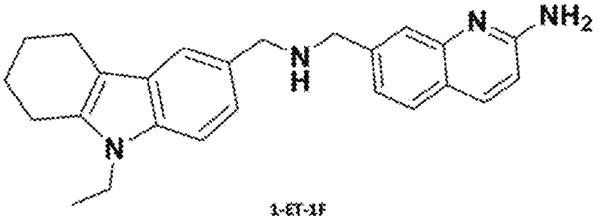
FIG. 6. depicts the proposed binding poses of 1-ET-1F bound to PRMT 5.
Figure 6:
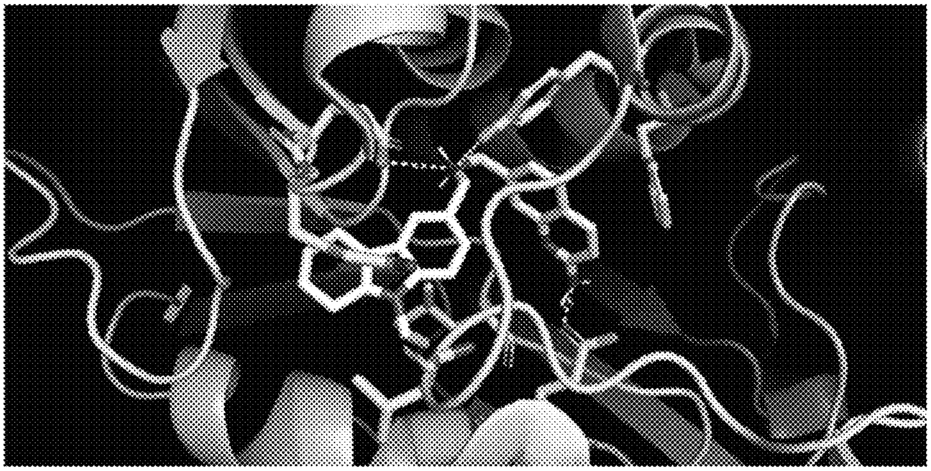
Figure 7:
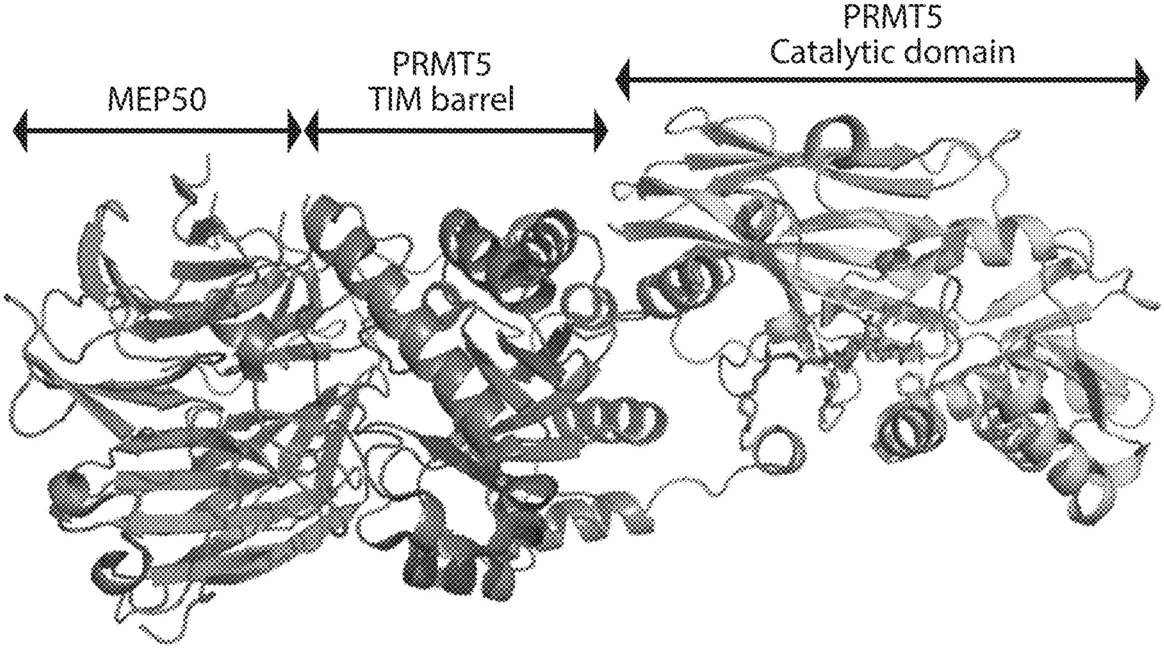
FIG. 7. depicts the overall structure of PRMT5:MEP50 complex (PDB code 4GQB).
Figure 8:
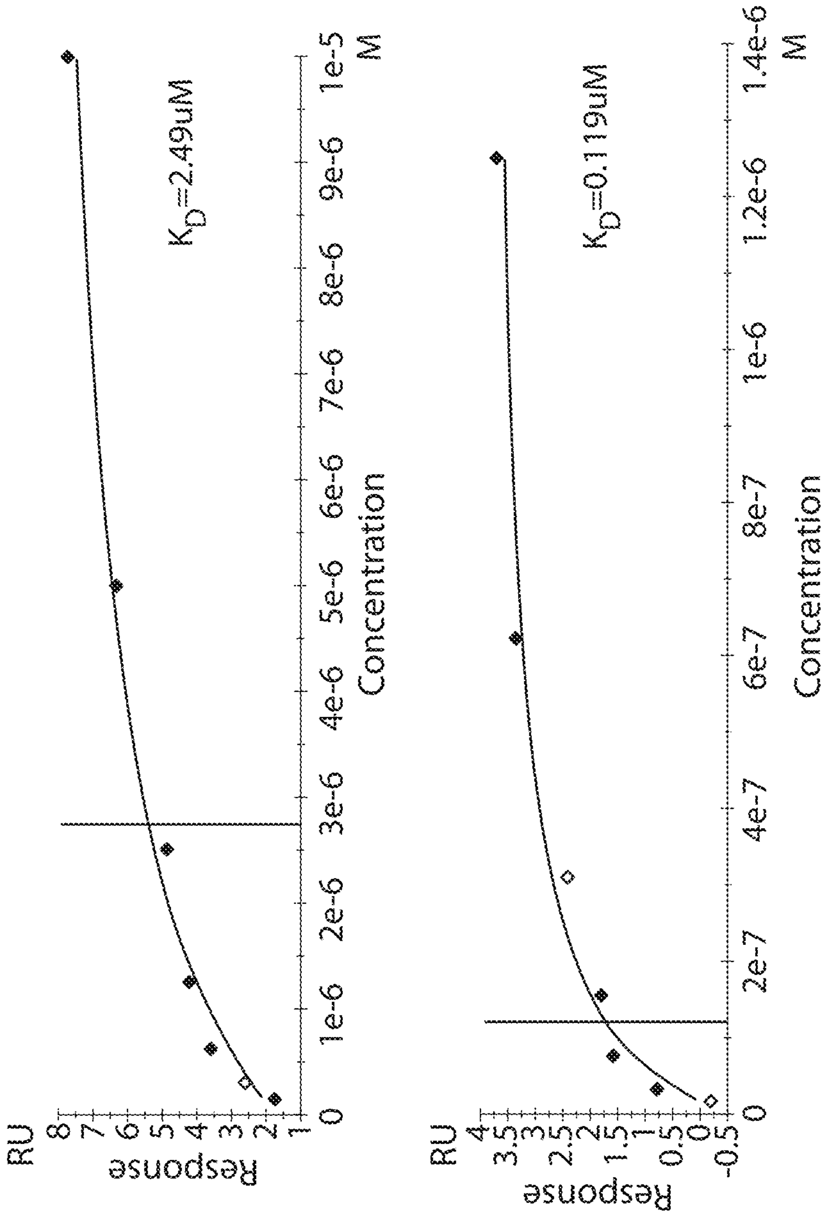
FIG. 8. depicts SPR binding results of CMP5 and 6-1F.
Figure 8:
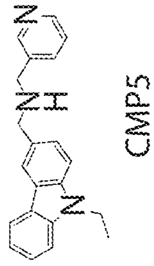
Figure 8:
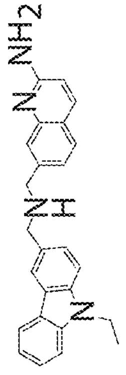
Figure 9:
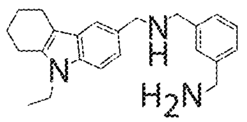
FIG. 9. depicts MCF-7 cell viability of PRMT 5 inhibitors
Figure 9:
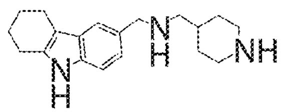
Figure 9:
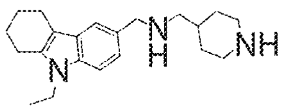
Figure 9:
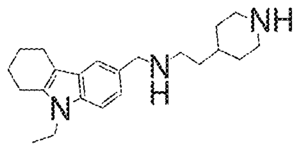
Figure 9:
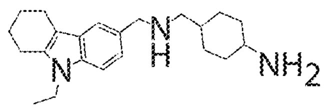
Figure 9:
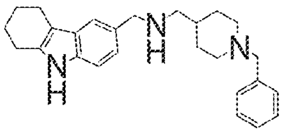
Figure 9:
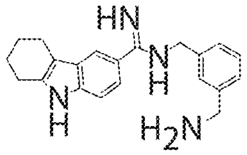
Figure 9:
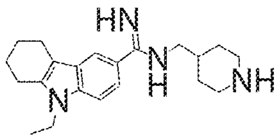
Figure 9:
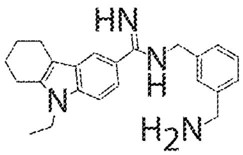
Figure 9:
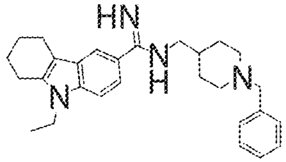
Figure 10A:
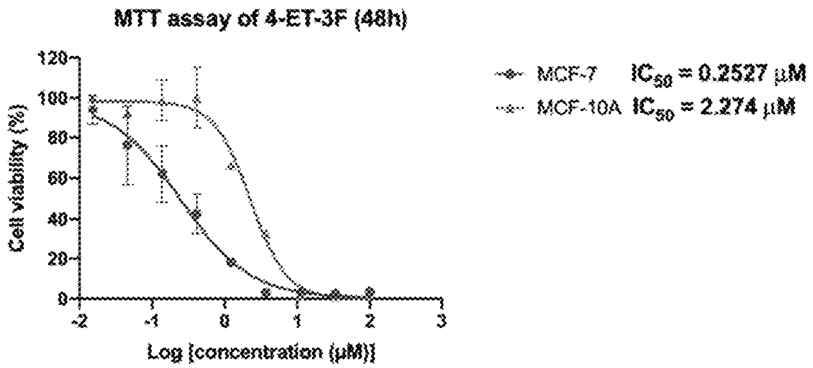
FIGS. 10A-10B. depict MCF-7 and MCF-10A cell viability of 4-ET-3F (FIG. 10A) and 8-ET-4F (FIG. 10B).
Figure 10B:
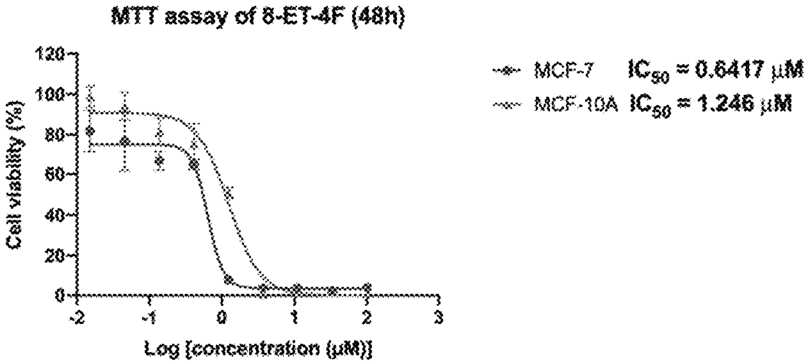
Figure 11:
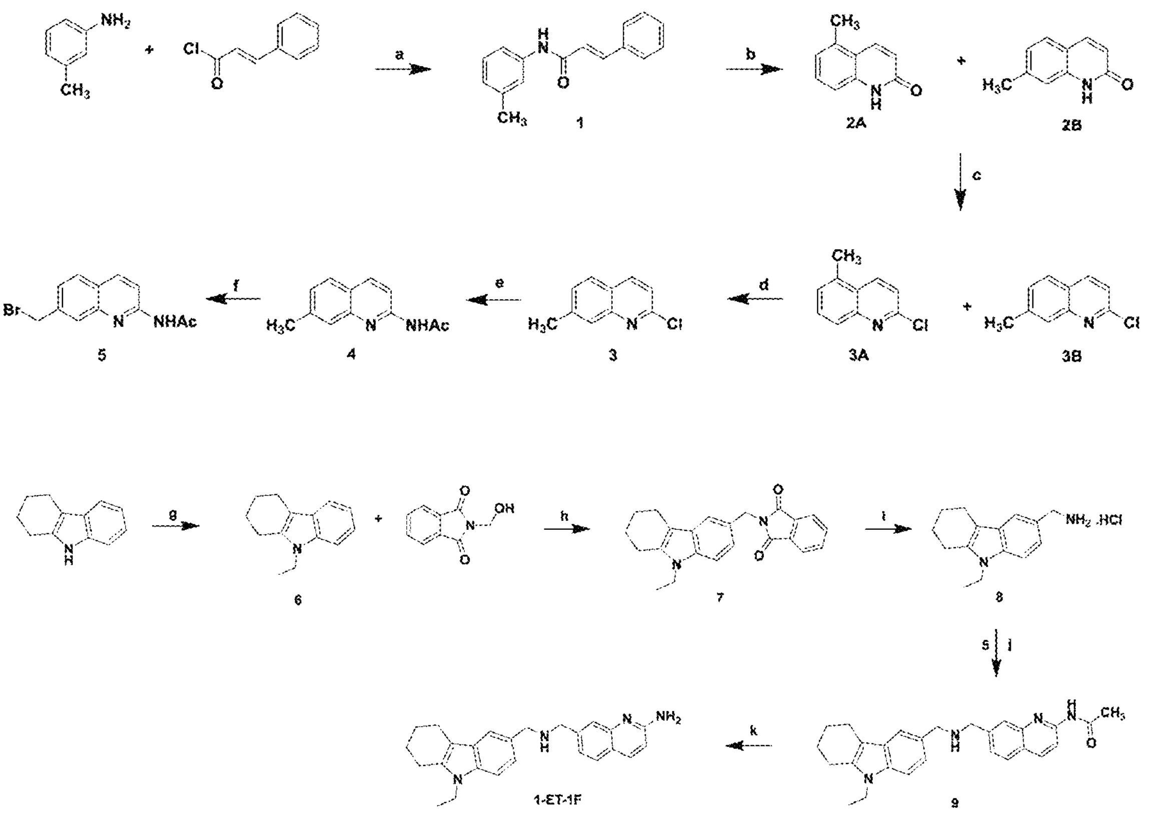
FIG. 11. depicts Scheme 1—synthetic route of 1-ET-1F15.
Figure 12:
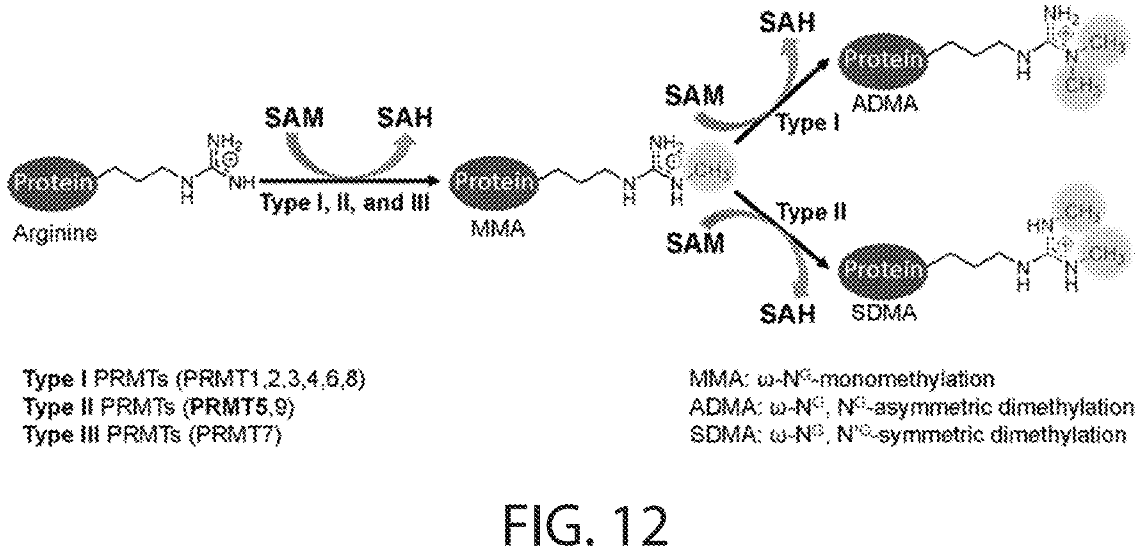
FIG. 12. depicts types of arginine methylation.
Figure 13:
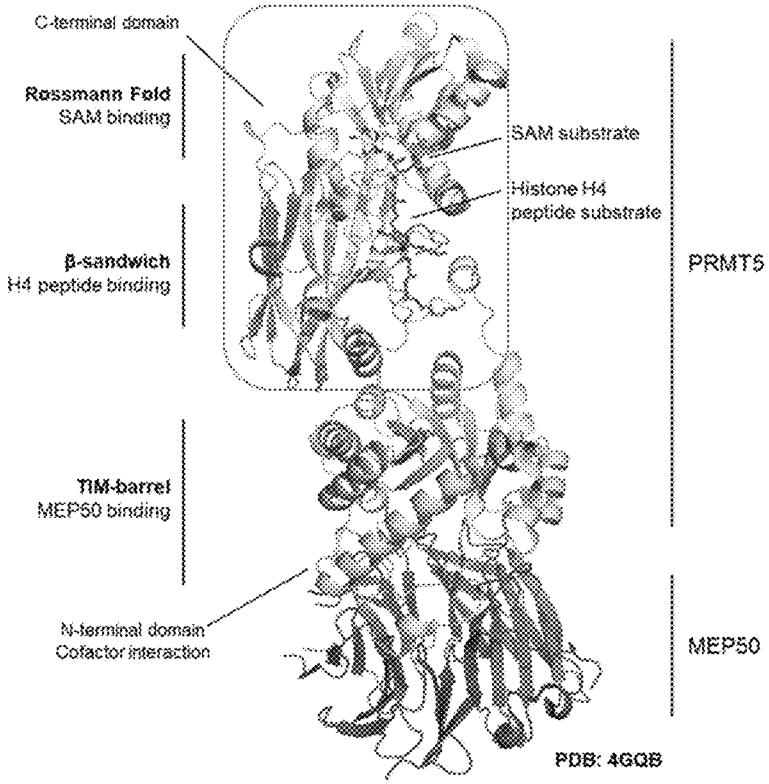
FIG. 13. depicts the crystal structure of human PRMT5:MEP50 (PDB 4GQB). Currently, there are two classes of PRMT5 inhibitors. The first class is cofactor-competitive inhibitors, which are always cofactor analogs contain a nucleoside moiety whose ribose and adenine sub-structures are strongly favored by the Rossmann fold motif which recognizes nucleoside-based cofactors specifically. The second class is H4 substrate-competitive inhibitors. There are highly potent and selective inhibitors with enzymatic IC50 at single digit nanomolar level; however, their function relay on the pre-binding of cofactor SAM.
Figure 14A:
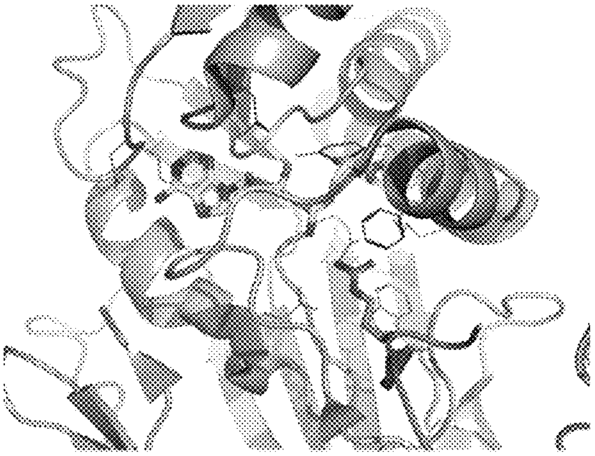
FIG. 14. (A-F) depicts binding interactions of compounds. Based on the crystal structure of PRMT5, we have explored the entire active site and identified a novel lead compound CMP5 through virtual screening. The predicted binding mode of CMP5 shows a novel binding mechanism by occupying both cofactor and substrate binding sites. While the enzymatic inhibition activity of CMP5 was weak, we have optimized the compound by incorporating the quinolinamine moiety from a cofactor-competitive inhibitor JNJ-64619178. Here, we report a series of hybrid CMP5 analogs with increased potency by ~50-fold (1-BUT-1F enzymatic IC50=7.89 μM).
Figure 14B:
Figure 14C:
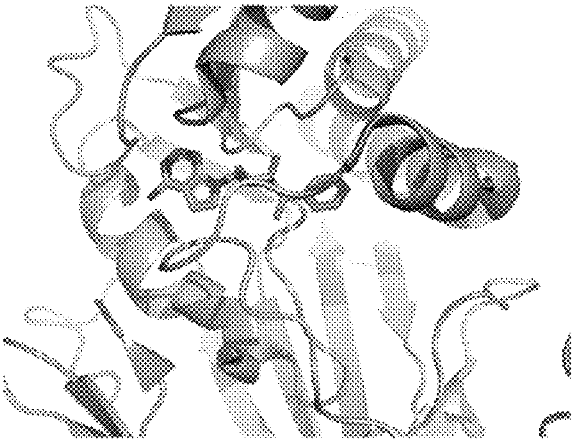
Figure 14D:
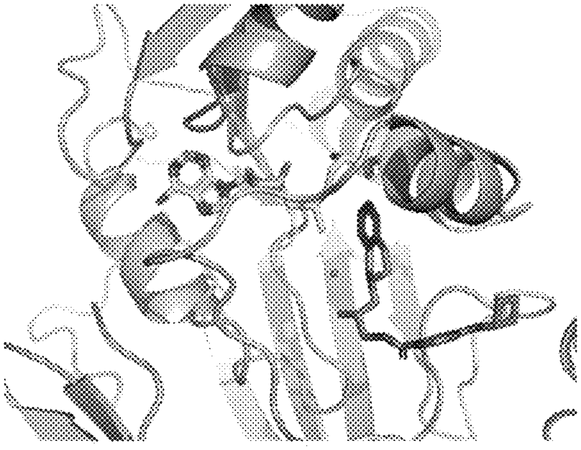
Figure 14E:
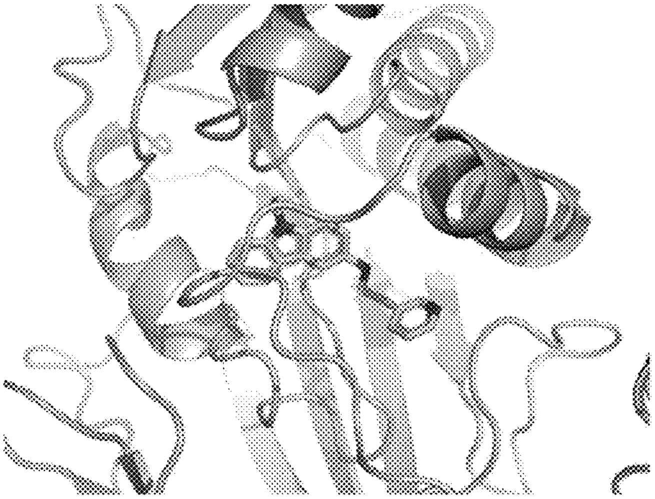
Figure 14F:
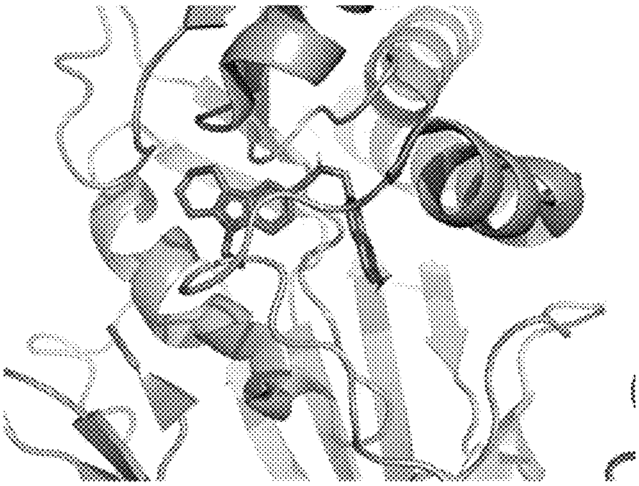
Figure 15A:
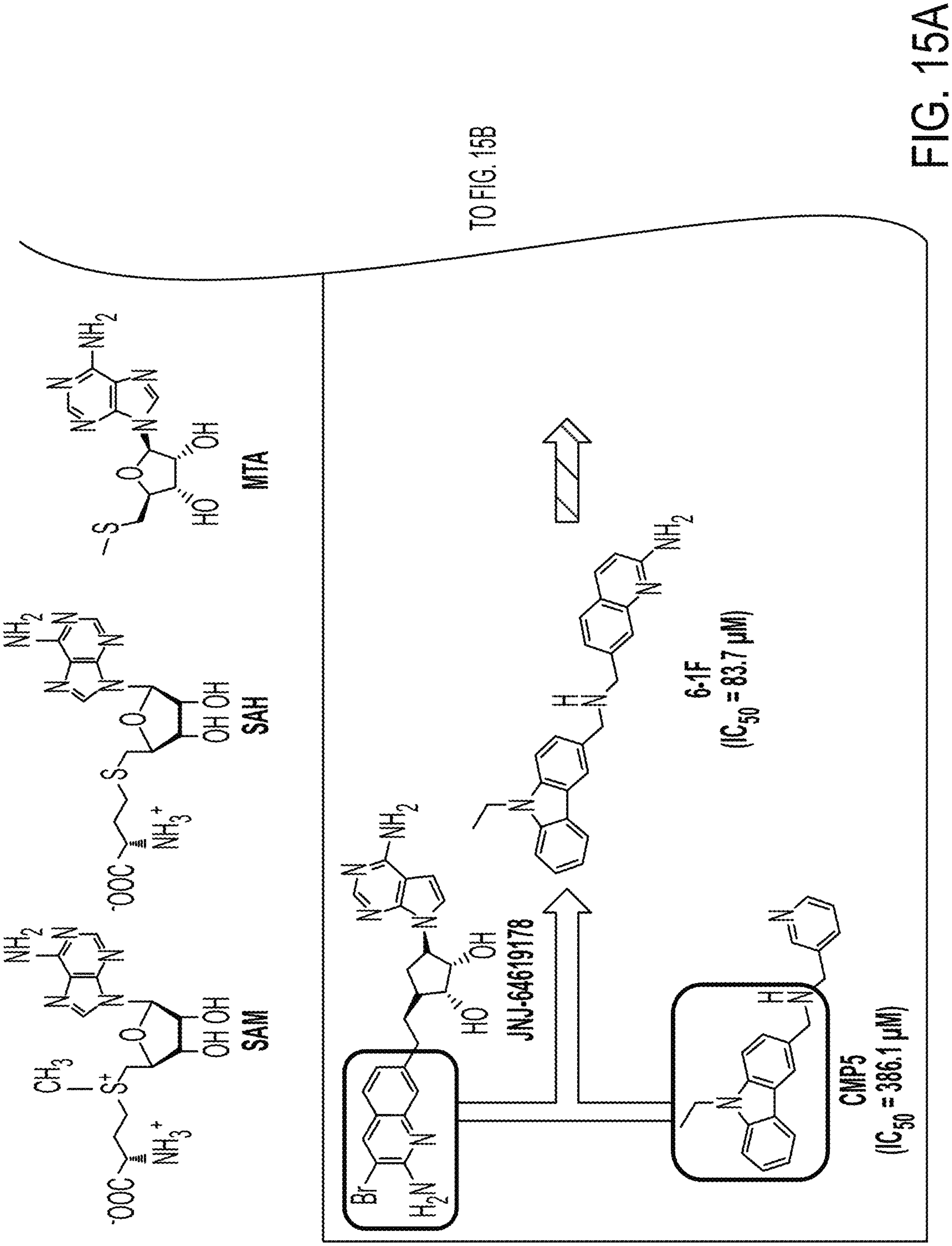
FIGS. 15A-15B. depict chemical structures of PRMT5 inhibitors.
Figure 15B:
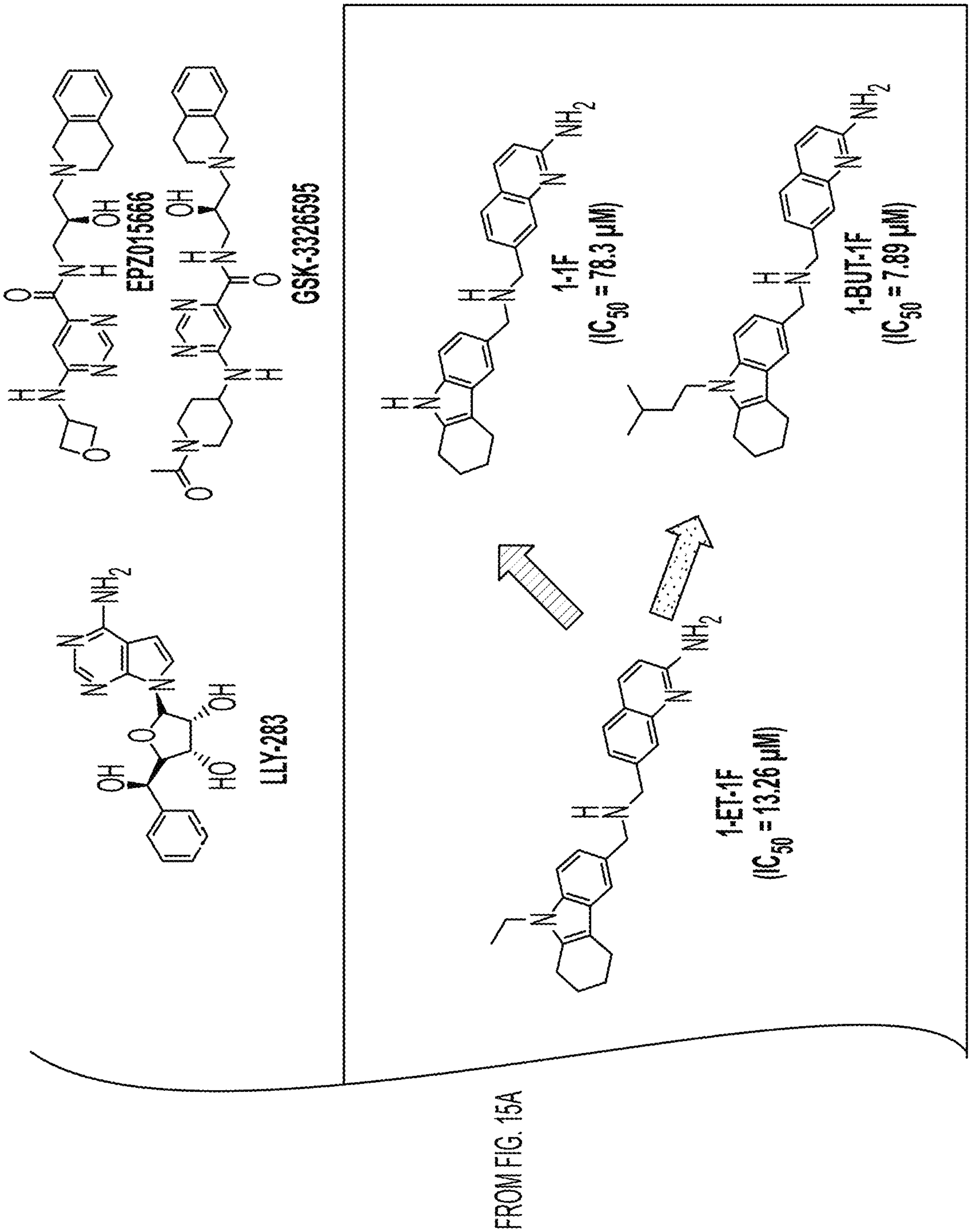
Figure 16:
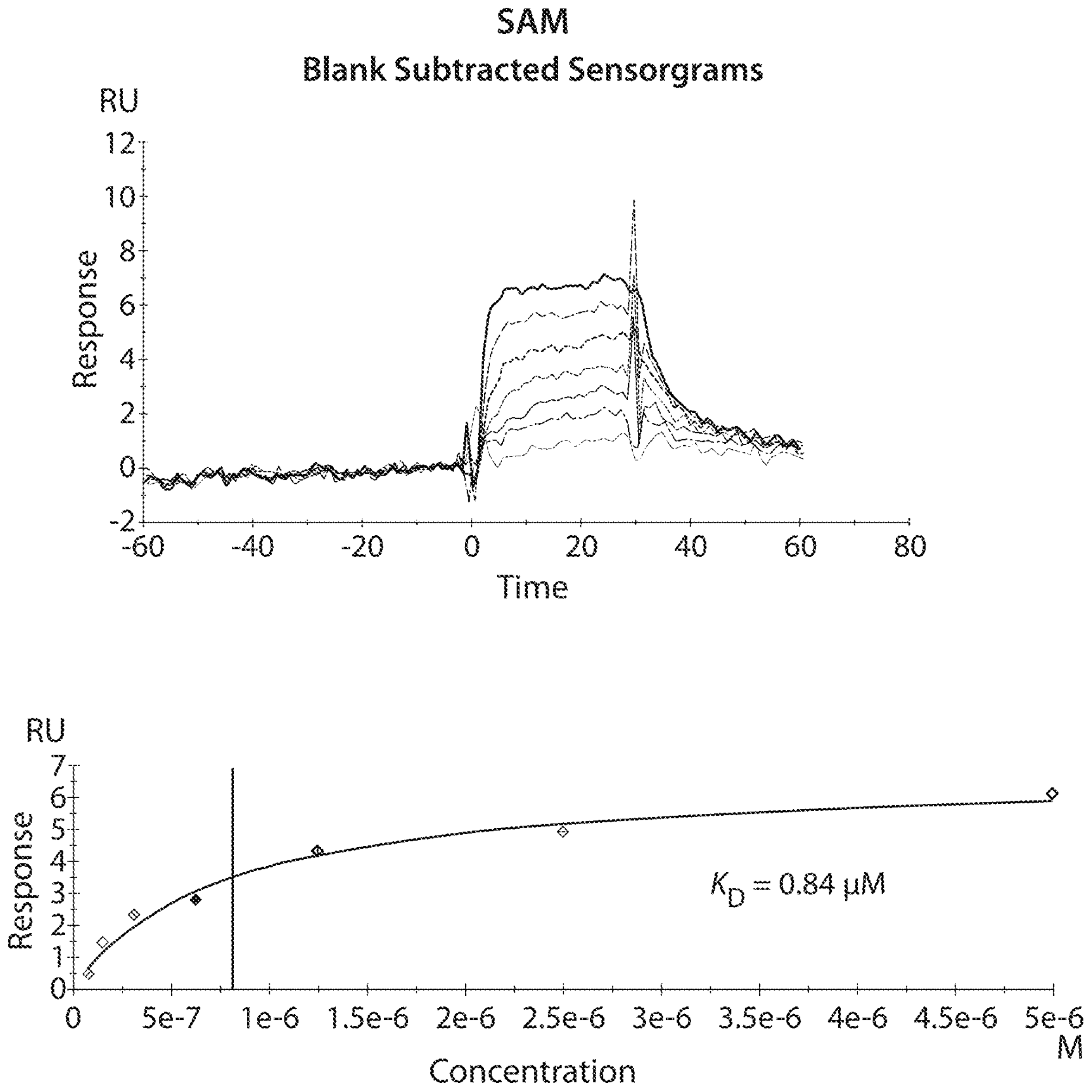
FIG. 16. depicts SPR binding experiments for binding affinity ($K_D$) determination and competitive binding analysis for compounds.
Figure 16:
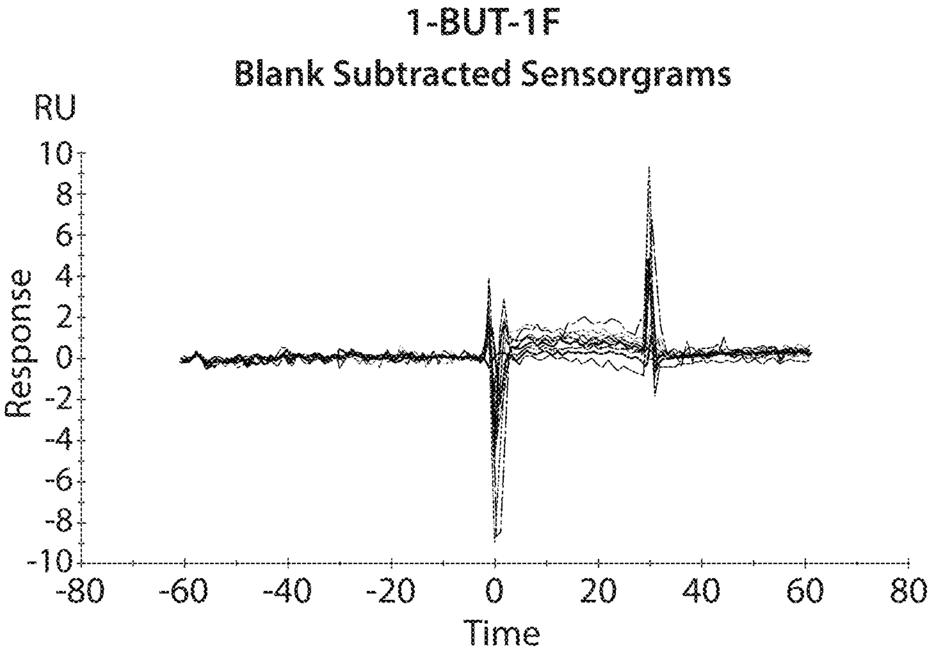
Figure 16:
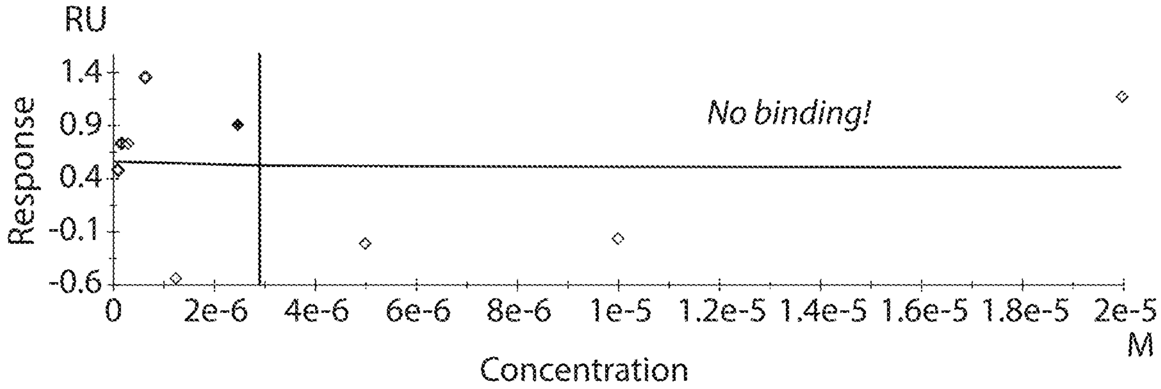
Figure 16:
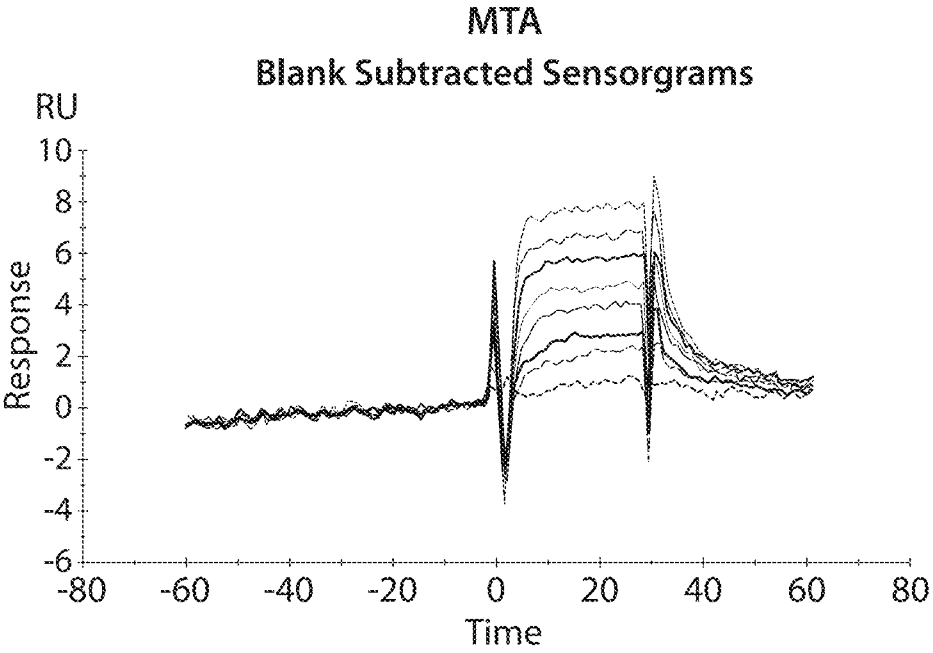
Figure 16:
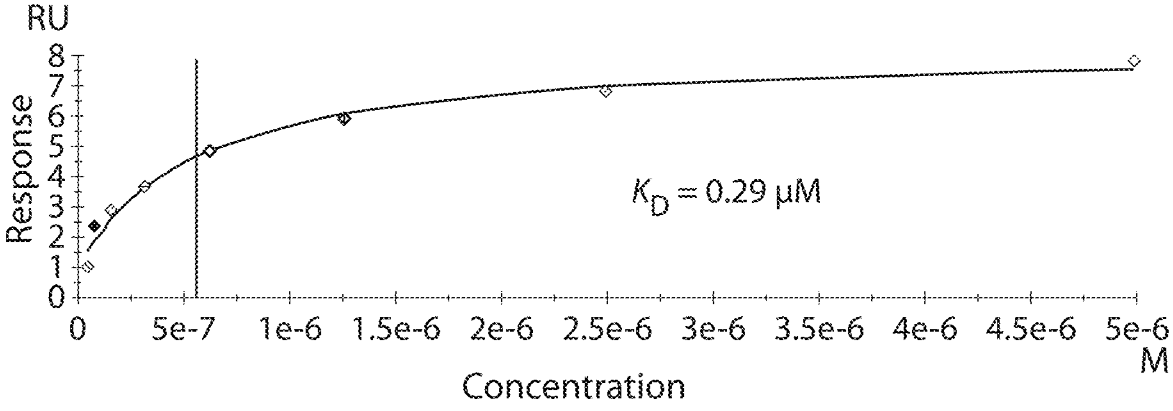
Figure 16:
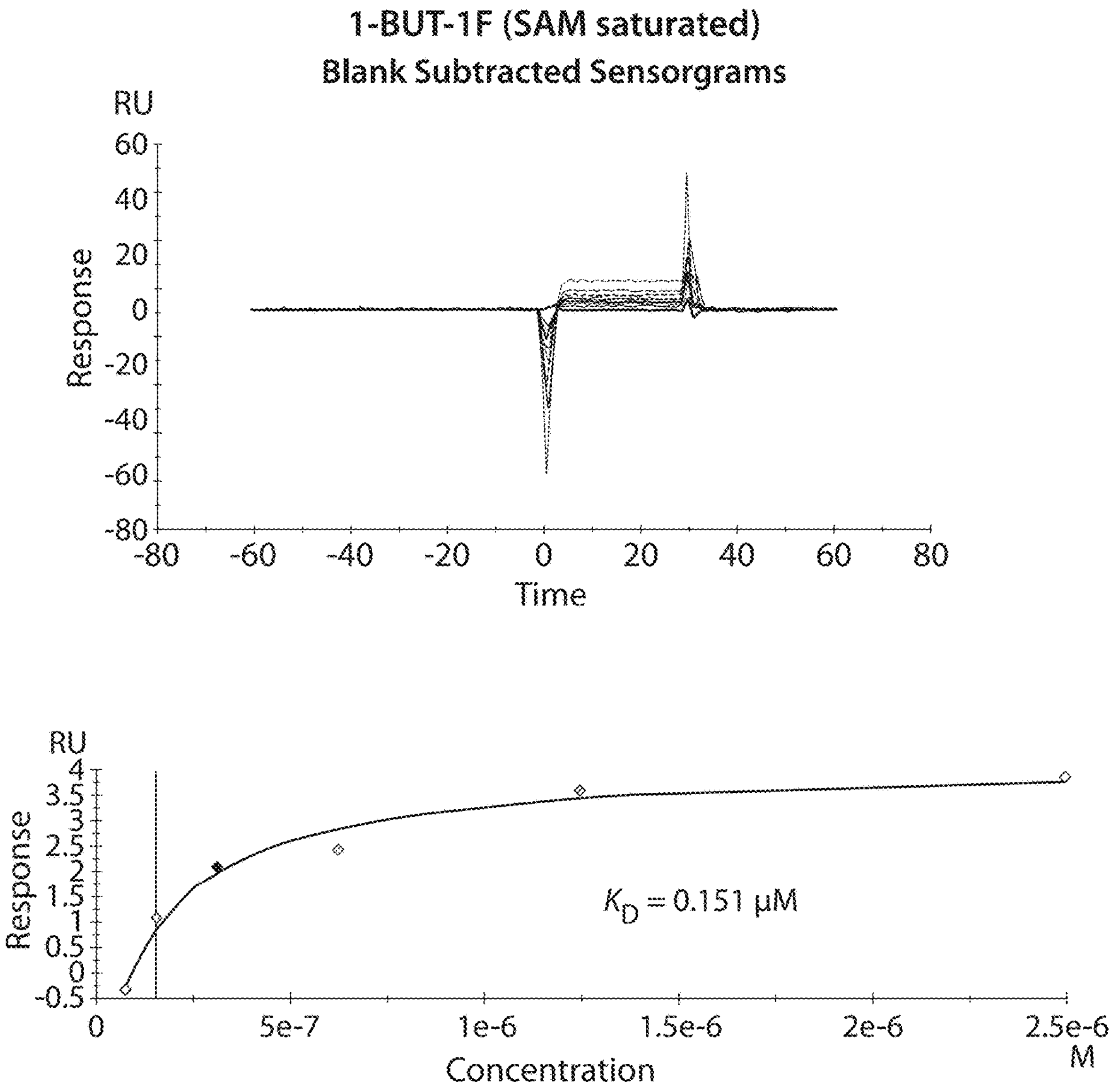
Figure 16:
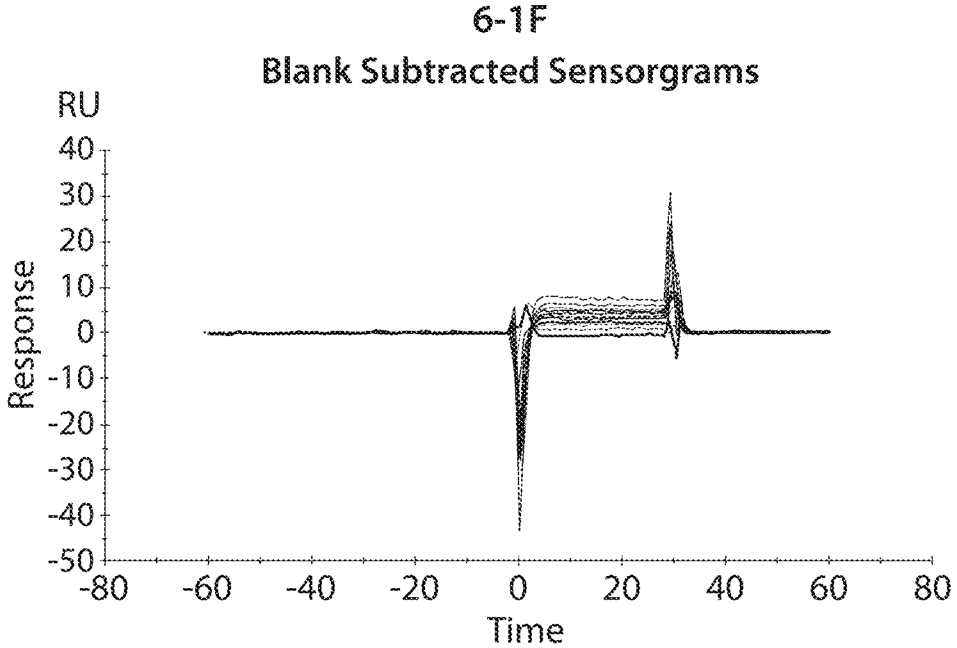
Figure 16:
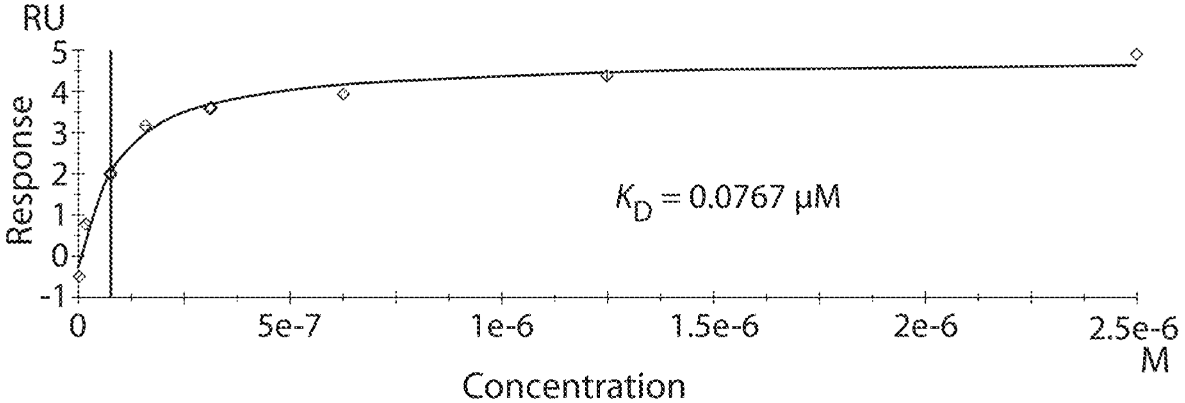
Figure 16:
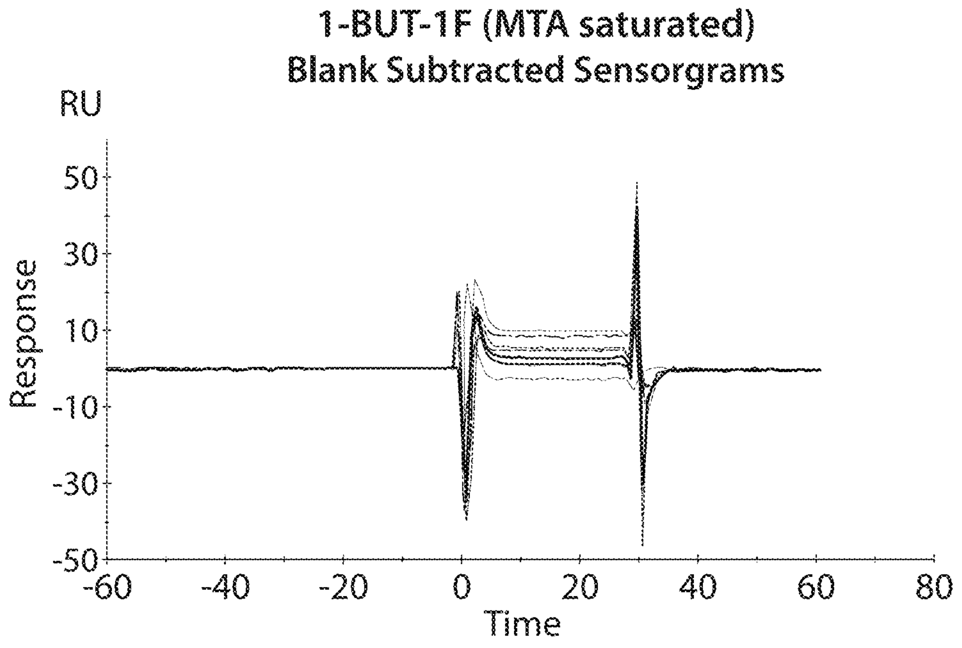
Figure 16:
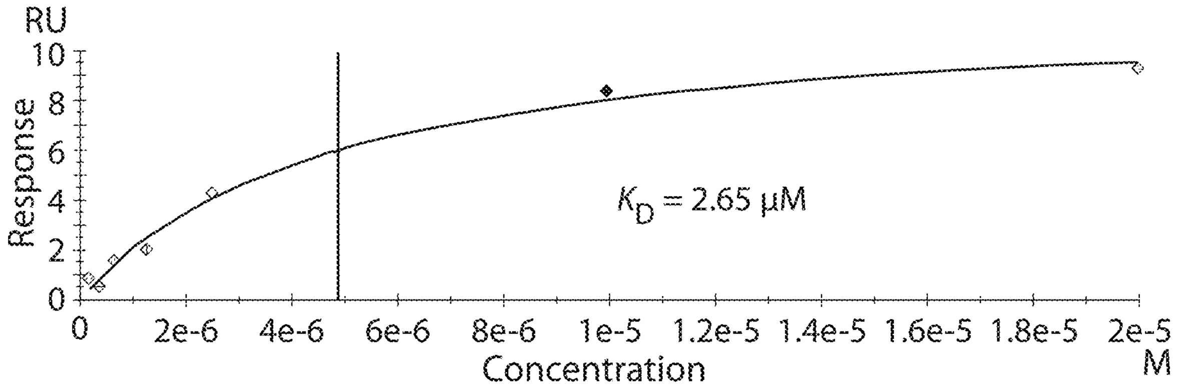
Figure 17A:
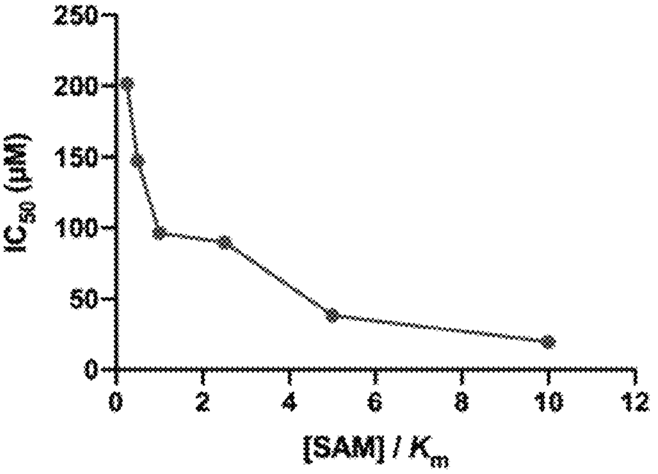
FIG. 17. depicts (A-B) Mechanism of inhibition (MOI) study of 1-ET-1F by enzymatic assay suggested that it might be a substrate-competitive inhibitor. (C-D) predicted binding modes of 1-ET-1F at the substrate binding pocket in the presence of MTA.
Figure 17B:
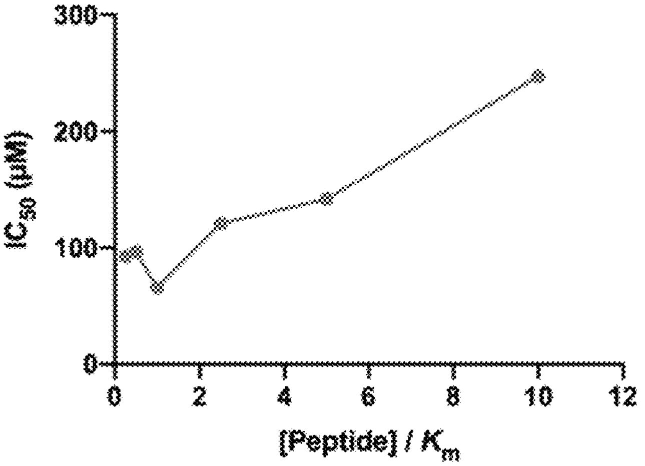
Figure 17C:
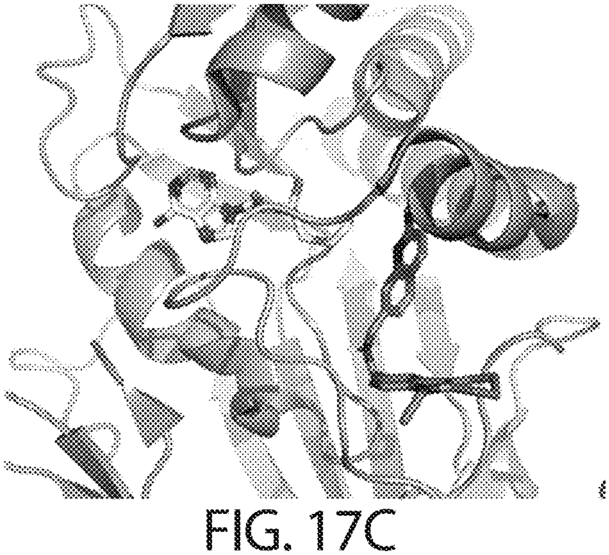
Figure 17D:
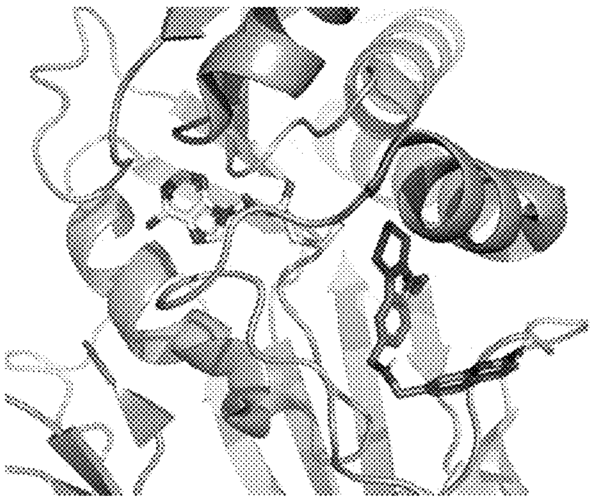
Figure 18A:
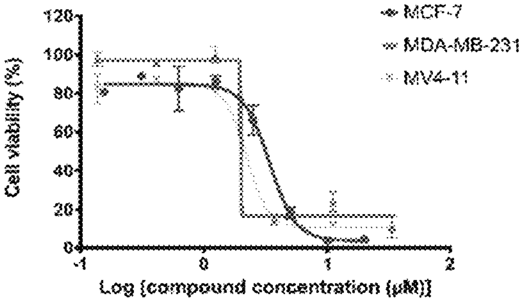
FIG. 18. depicts (A) Anti-proliferative effect of designed molecules in different cancel cell lines (48 h). (B) Western blot result showed a decreased protein symmetric demethylation level in MV4-11 cell line (48 h).
Figure 18B:
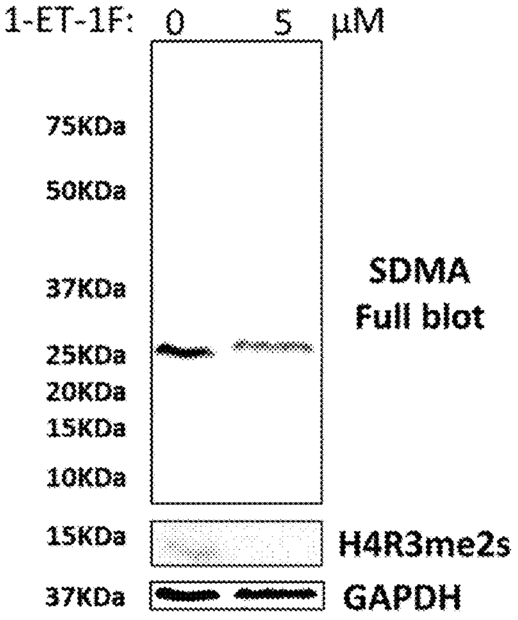
Figure 19:
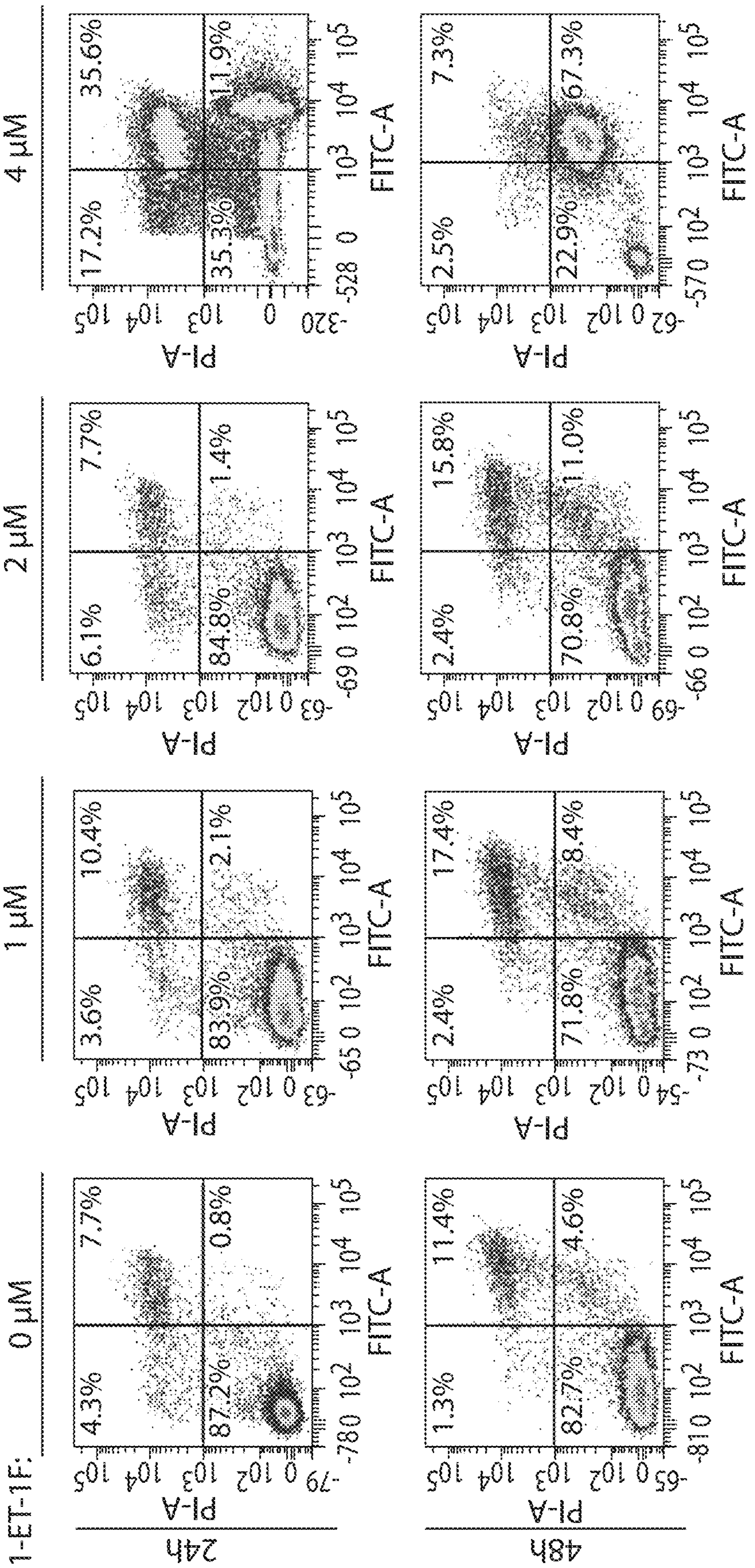
FIG. 19. depicts apoptotic effects of 1-ET-1F in a dose-dependent manner in MV4-11 cell line.
Figure 20:
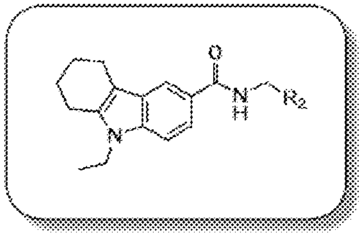
FIG. 20 depicts enzymatic inhibition assay results for 11-series compounds.
Figure 20:
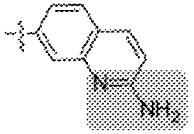
Figure 20:
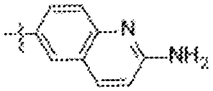
Figure 20:
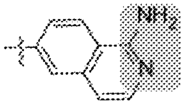
Figure 20:
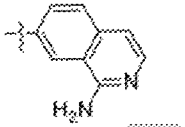
Figure 20:
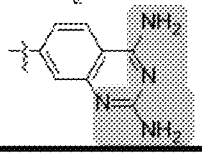
Figure 20:
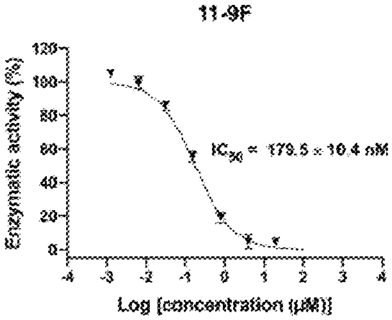
Figure 21:
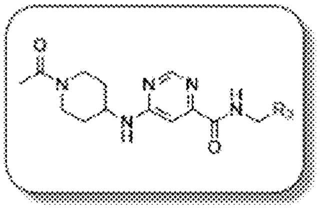
FIG. 21 depicts enzymatic inhibition assay results for 15-series compounds.
Figure 21:
Figure 21:
Figure 21:
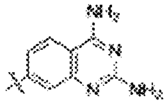
Figure 21:
Figure 21:
Figure 21:
Figure 22:
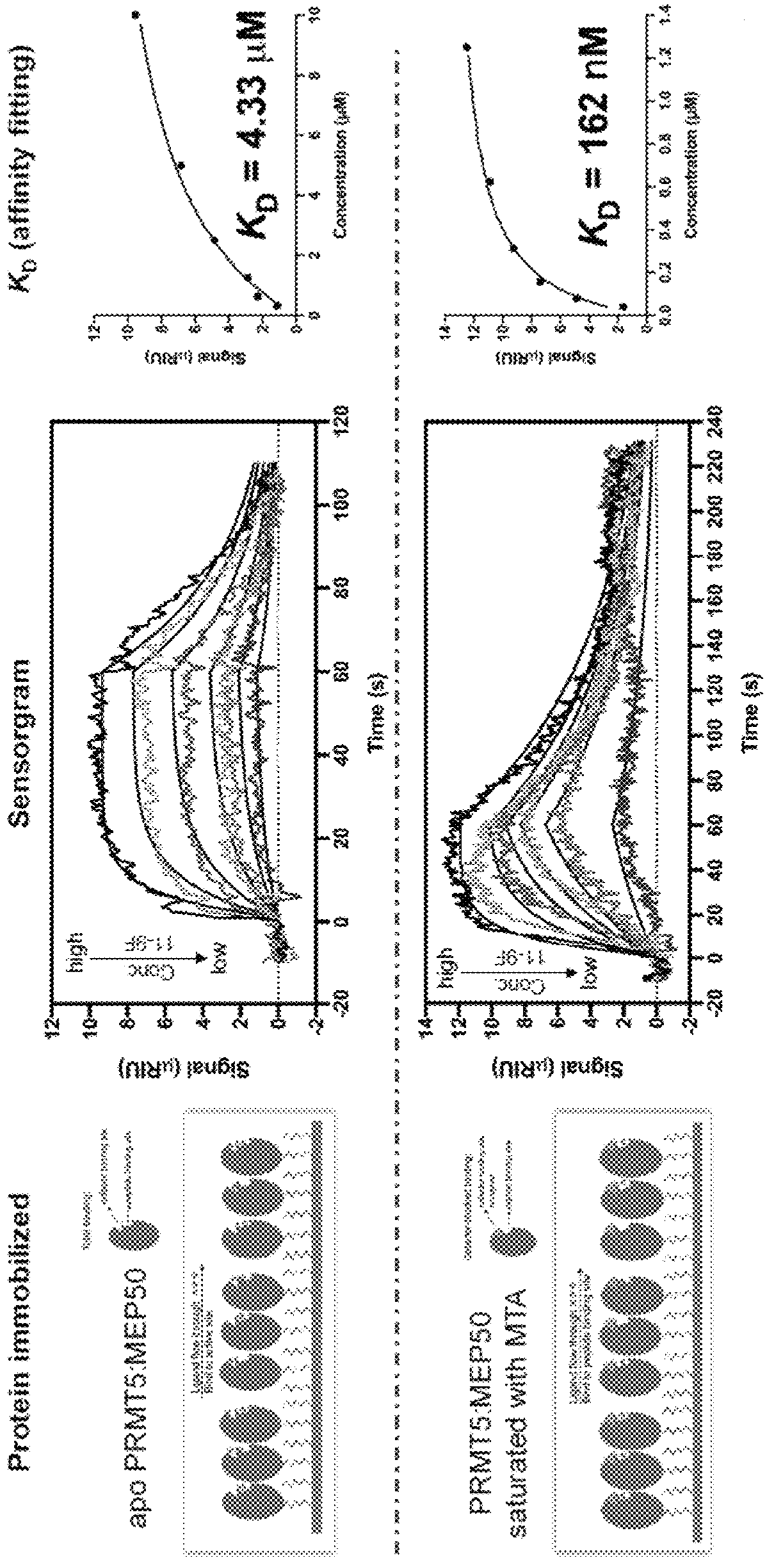
FIG. 22 depicts representative compound 11-9F binding to PRMT5 results using SPR/Biacore. Upper panel shows the compound binding to apo PRMT5/MEP50 complex with Kd of 4.3 uM; lower panel shows the compound binding to PRMT5/MTA/MEP50 holo complex with Kd of 162 nM. Together with the table (FIG. 23), this demonstrates that test compounds bind to PRMT5/MEP50 complex with or without MTA/SAM/SAH binding to the cofactor site, uniquely targeting MTAP deletion subset of cancers.
Figure 23:
FIG. 23 depicts enzymatic inhibition assay results and binding affinity results for test compounds.
Figure 23:
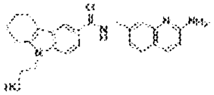
Figure 23:
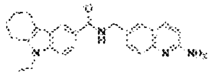
Figure 23:
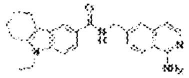
Figure 23:
Figure 23:
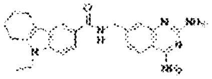
Figure 23:
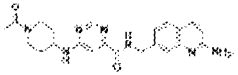
Figure 23:
Figure 24:
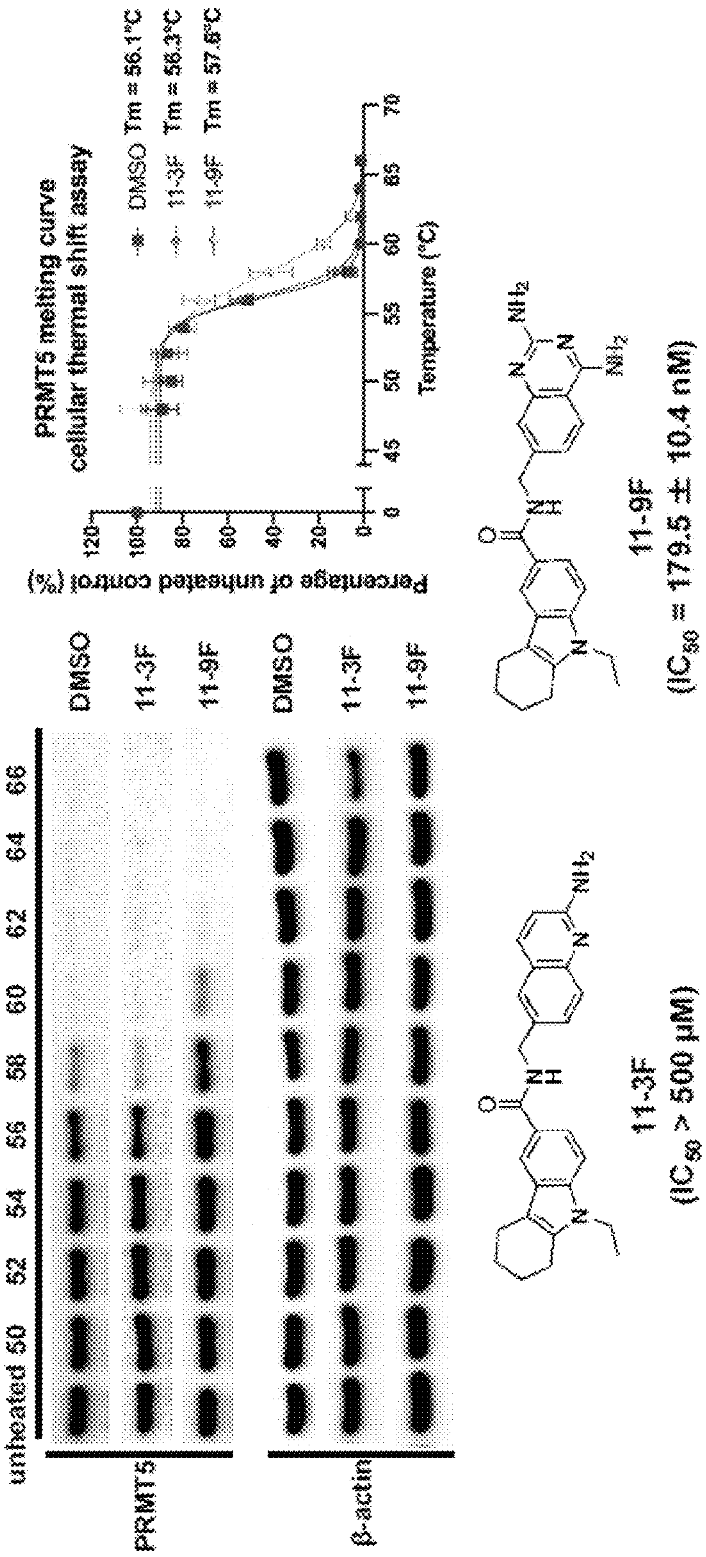
FIG. 24 depicts representative compound 11-9F cellular target engagement results using a Cellular Thermal Shift Assay. Left panel demonstrates that compared to negative control compound 11-3F, 11-9F binds to PRMT5 in the MDA-MB-231 triple negative breast cancer cells, resulting in increased thermal stability; right panel quantifies the PRMT5 melting temperature increase of 1.5 degree Celsius due to 11-9F binding.
Figure 25:
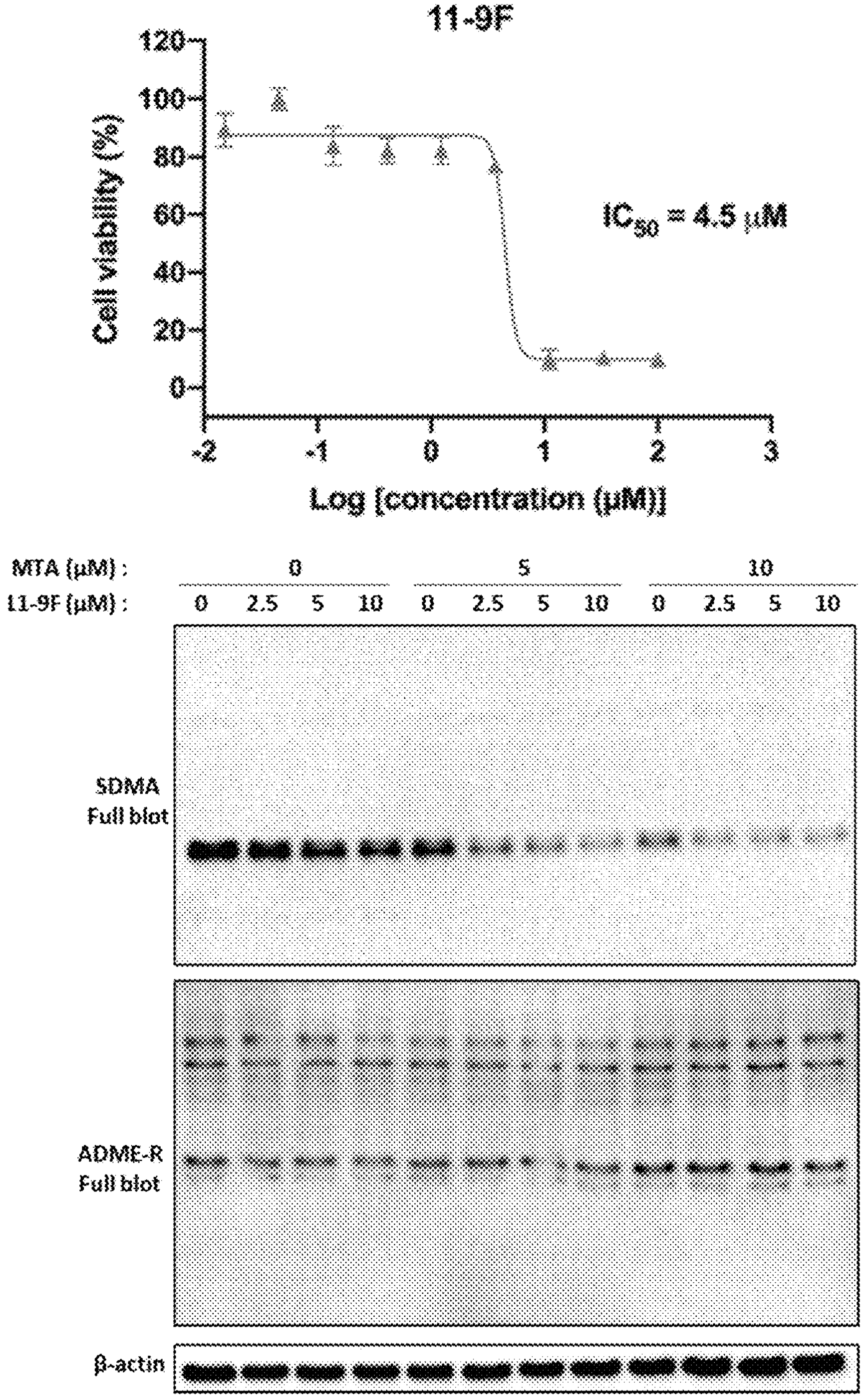
FIG. 25 depicts effects of compound 11-9F in cells, MDA-MB-231 breast cancer cell line.

In order that the invention may be more readily understood, certain terms are first defined here for convenience.

As used herein, the term "treating" a disorder encompasses ameliorating, mitigating and/or managing the disorder and/or conditions that may cause the disorder. The terms "treating" and "treatment" refer to a method of alleviating or abating a disease and/or its attendant symptoms. In accordance with the present invention "treating" includes blocking, inhibiting, attenuating, modulating, reversing the effects of and reducing the occurrence of e.g., the harmful effects of a disorder.

As used herein, "inhibiting" encompasses preventing, reducing and halting progression.

As used herein, "activating" encompasses permitting, increasing and enhancing progression.

The term "modulate" refers to increases or decreases in the activity of a cell in response to exposure to a compound of the invention.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. Particularly, in embodiments the compound is at least 85% pure, more preferably at least 90% pure, more preferably at least 95% pure, and most preferably at least 99% pure.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "peptide" is a sequence of at least two amino acids. Peptides can consist of short as well as long amino acid sequences, including proteins.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "protein" refers to series of amino acid residues connected one to the other by peptide bonds between the alpha-amino and carboxy groups of adjacent residues.

Amino acids may be referred to herein by either their commonly known three letter symbols or by the one-letter symbols recommended by the IUPAC-IUB Biochemical Nomenclature Commission.

As to amino acid sequences, one of skill will recognize that individual substitutions, deletions or additions to a peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

Macromolecular structures such as polypeptide structures can be described in terms of various levels of organization. For a general discussion of this organization, see, e.g., Alberts et al., Molecular Biology of the Cell (3rd ed., 1994) and Cantor and Schimmel, Biophysical Chemistry Part I. The Conformation of Biological Macromolecules (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response. An effective amount is also one in which any toxic or detrimental effects (e.g., side effects) of the elastase inhibitor compound are outweighed by the therapeutically beneficial effects.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The term "therapeutically effective amount" refers to that amount of the compound being administered sufficient to prevent development of or alleviate to some extent one or more of the symptoms of the condition or disorder being treated.

A therapeutically effective amount of compound (i.e., an effective dosage) may range from about 0.005 μg/kg to about 200 mg/kg, preferably about 0.01 mg/kg to about 200 mg/kg, more preferably about 0.015 mg/kg to about 30 mg/kg of body weight. In other embodiments, the therapeutically effect amount may range from about 1.0 pM to about 10 μM. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, preferably, can include a series of treatments. In one example, a subject is treated with a compound in the range of between about 0.005 g/kg to about 200 mg/kg of body weight, one time per day for between about 1 to 10 weeks, preferably between 2 to 8 weeks, more preferably between about 3 to 7 weeks, and even more preferably for about 4, 5, or 6 weeks. In another example, a subject may be treated daily for several years in the setting of a chronic condition or illness. It will also be appreciated that the effective dosage of a compound used for treatment may increase or decrease over the course of a particular treatment.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included. In aspects, the compounds of the invention are prodrugs of any of the formulae herein.

The term "subject" refers to animals such as mammals, including, but not limited to, primates (e.g., humans), cows, sheep, goats, horses, dogs, cats, rabbits, rats, mice and the like. In certain embodiments, the subject is a human.

The terms "a," "an," and "the" refer to "one or more" when used in this application, including the claims. Thus, for example, reference to "a sample" includes a plurality of samples, unless the context clearly is to the contrary (e.g., a plurality of samples), and so forth.

Throughout this specification and the claims, the words "comprise," "comprises," and "comprising" are used in a non-exclusive sense, except where the context requires otherwise.

As used herein, the term "about," when referring to a value is meant to encompass variations of, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Furthermore the compounds of the invention include olefins having either geometry: "Z" refers to what is referred to as a "cis" (same side) conformation whereas "E" refers to what is referred to as a "trans" (opposite side) conformation. With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

As used herein, the term "alkyl" refers to a straight-chained or branched hydrocarbon group containing 1 to 12 carbon atoms. The term "lower alkyl" refers to a C1-C6 alkyl chain. Examples of alkyl groups include methyl, ethyl, n-propyl, isopropyl, tert-butyl, and n-pentyl. Alkyl groups may be optionally substituted with one or more substituents.

The term "haloalkyl" refers to an alkyl group that is substituted by one or more halo substituents. Examples of haloalkyl groups include fluoromethyl, difluoromethyl, trifluoromethyl, bromomethyl, chloromethyl, and 2,2,2-trifluoroethyl.

The term "alkenyl" refers to an unsaturated hydrocarbon chain that may be a straight chain or branched chain, containing 2 to 12 carbon atoms and at least one carbon-carbon double bond. Alkenyl groups may be optionally substituted with one or more substituents.

The term "alkynyl" refers to an unsaturated hydrocarbon chain that may be a straight chain or branched chain, containing the 2 to 12 carbon atoms and at least one carbon-carbon triple bond. Alkynyl groups may be optionally substituted with one or more substituents.

The term "arylalkynyl" refers to an unsaturated hydrocarbon chain that may be a straight chain or branched chain, containing 2 to 12 carbon atoms and at least one carbon-carbon triple bond wherein one or more of the sp hybridized carbons of the alkynyl unit attaches to an aryl moiety. Alkynyl groups may be optionally substituted with one or more substituents.

The $sp^2$ or sp carbons of an alkenyl group and an alkynyl group, respectively, may optionally be the point of attachment of the alkenyl or alkynyl groups.

The term "alkoxy" refers to an —O-alkyl radical.

As used herein, the term "halogen", "hal" or "halo" means —F, —Cl, —Br or —I.

The term "alkylthio" refers to an —S-alkyl substituent.

The term "alkoxyalkyl" refers to an -alkyl-O-alkyl substituent.

The term "haloalkoxy" refers to an —O-alkyl that is substituted by one or more halo substituents. Examples of haloalkoxy groups include trifluoromethoxy, and 2,2,2-trifluoroethoxy.

The term "haloalkoxyalkyl" refers to an -alkyl-O-alkyl' where the alkyl' is substituted by one or more halo substituents.

The term "haloalkylaminocarbonyl" refers to a —C(O)-amino-alkyl where the alkyl is substituted by one or more halo substituents.

The term "haloalkylthio" refers to an —S-alkyl that is substituted by one or more halo substituents. Examples of haloalkylthio groups include trifluoromethylthio, and 2,2,2-trifluoroethylthio.

The term "haloalkylcarbonyl" refers to an —C(O)-alkyl that is substituted by one or more halo substituents. An example of a haloalkylcarbonyl group includes trifluoroacetyl.

The term "cycloalkyl" refers to a hydrocarbon 3-8 membered monocyclic or 7-14 membered bicyclic ring system having at least one saturated ring or having at least one non-aromatic ring, wherein the non-aromatic ring may have some degree of unsaturation.

Cycloalkyl groups may be optionally substituted with one or more substituents. In one embodiment, 0, 1, 2, 3, or 4 atoms of each ring of a cycloalkyl group may be substituted by a substituent. Representative examples of cycloalkyl group include cyclopropyl, cyclopentyl, cyclohexyl, cyclobutyl, cycloheptyl, cyclopentenyl, cyclopentadienyl, cyclohexenyl, cyclohexadienyl, and the like.

The term "cycloalkoxy" refers to an —O-cycloalkyl substituent.

The term "cycloalkoxyalkyl" refers to an -alkyl-O-cycloalkyl substituent.

The term "cycloalkylalkoxy" refers to an —O-alkyl-cycloalkyl substituent.

The term "cycloalkylaminocarbonyl" refers to an —C(O)—NH-cycloalkyl substituent.

The term "aryl" refers to a hydrocarbon monocyclic, bicyclic or tricyclic aromatic ring system. Aryl groups may be optionally substituted with one or more substituents. In one embodiment, 0, 1, 2, 3, 4, 5 or 6 atoms of each ring of an aryl group may be substituted by a substituent. Examples of aryl groups include phenyl, naphthyl, anthracenyl, fluorenyl, indenyl, azulenyl, and the like.

The term "aryloxy" refers to an —O-aryl substituent.

The term "arylalkoxy" refers to an —O-alkyl-aryl substituent.

The term "arylalkylthio" refers to an —S-alkyl-aryl substituent.

The term "arylthioalkyl" refers to an -alkyl-S-aryl substituent.

The term "arylalkylaminocarbonyl" refers to a —C(O)-amino-alkyl-aryl substituent.

The term "arylalkylsulfonyl" refers to an —$S(O)_2$-alkyl-aryl substituent.

The term "arylalkylsulfinyl" refers to an —S(O)-alkyl-aryl substituent.

The term "aryloxyalkyl" refers to an -alkyl-O-aryl substituent.

The term "alkylaryl" refers to an -aryl-alkyl substituent.

The term "arylalkyl" refers to an -alkyl-aryl substituent.

The term "heteroaryl" refers to an aromatic 5-8 membered monocyclic, 8-12 membered bicyclic, or 11-14 membered tricyclic ring system having 1-4 ring heteroatoms if monocyclic, 1-6 heteroatoms if bicyclic, or 1-9 heteroatoms if tricyclic, said heteroatoms selected from O, N, or S, and the remainder ring atoms being carbon (with appropriate hydrogen atoms unless otherwise indicated). Heteroaryl groups may be optionally substituted with one or more substituents. In one embodiment, 0, 1, 2, 3, or 4 atoms of each ring of a heteroaryl group may be substituted by a substituent. Examples of heteroaryl groups include pyridyl, furanyl, thienyl, pyrrolyl, oxazolyl, oxadiazolyl, imidazolyl thiazolyl, isoxazolyl, quinolinyl, pyrazolyl, isothiazolyl, pyridazinyl, pyrimidinyl, pyrazinyl, triazinyl, isoquinolinyl, indazolyl, and the like.

The term "heteroaryloxy" refers to an —O-heteroaryl substituent.

The term "heteroarylalkoxy" refers to an —O-alkyl-heteroaryl substituent.

The term "heteroaryloxyalkyl" refers to an -alkyl-O-heteroaryl substituent. The term "nitrogen-containing heteroaryl" refers to a heteroaryl group having 1-4 ring nitrogen heteroatoms if monocyclic, 1-6 ring nitrogen heteroatoms if bicyclic, or 1-9 ring nitrogen heteroatoms if tricyclic.

The term "heterocycloalkyl" refers to a nonaromatic 3-8 membered monocyclic, 7-12 membered bicyclic, or 10-14 membered tricyclic ring system comprising 1-3 heteroatoms if monocyclic, 1-6 heteroatoms if bicyclic, or 1-9 heteroatoms if tricyclic, said heteroatoms selected from O, N, S, B, P or Si, wherein the nonaromatic ring system is completely saturated. Heterocycloalkyl groups may be optionally substituted with one or more substituents. In one embodiment, 0, 1, 2, 3, or 4 atoms of each ring of a heterocycloalkyl group may be substituted by a substituent. Representative heterocycloalkyl groups include piperidinyl, piperazinyl, tetrahydropyranyl, morpholinyl, thiomorpholinyl, 1,3-dioxolane, tetrahydrofuranyl, tetrahydrothienyl, thiorenyl, and the like.

The term "alkylamino" refers to an amino substituent which is further substituted with one or two alkyl groups. The term "aminoalkyl" refers to an alkyl substituent which is further substituted with one or more amino groups. The term "hydroxyalkyl" or "hydroxylalkyl" refers to an alkyl substituent which is further substituted with one or more hydroxyl groups. The alkyl or aryl portion of alkylamino, aminoalkyl, mercaptoalkyl, hydroxyalkyl, mercaptoalkoxy, sulfonylalkyl, sulfonylaryl, alkylcarbonyl, and alkylcarbonylalkyl may be optionally substituted with one or more substituents.

Acids and bases useful in the methods herein are known in the art. Acid catalysts are any acidic chemical, which can be inorganic (e.g., hydrochloric, sulfuric, nitric acids, aluminum trichloride) or organic (e.g., camphorsulfonic acid, p-toluenesulfonic acid, acetic acid, ytterbium triflate) in nature. Acids are useful in either catalytic or stoichiometric amounts to facilitate chemical reactions. Bases are any basic chemical, which can be inorganic (e.g., sodium bicarbonate, potassium hydroxide) or organic (e.g., triethylamine, pyridine) in nature. Bases are useful in either catalytic or stoichiometric amounts to facilitate chemical reactions.

Alkylating agents are any reagent that is capable of effecting the alkylation of the functional group at issue (e.g., oxygen atom of an alcohol, nitrogen atom of an amino group). Alkylating agents are known in the art, including in the references cited herein, and include alkyl halides (e.g., methyl iodide, benzyl bromide or chloride), alkyl sulfates (e.g., methyl sulfate), or other alkyl group-leaving group combinations known in the art. Leaving groups are any stable species that can detach from a molecule during a reaction (e.g., elimination reaction, substitution reaction) and are known in the art, including in the references cited herein, and include halides (e.g., I—, Cl—, Br—, F—), hydroxy, alkoxy (e.g., —OMe, —O-t-Bu), acyloxy anions (e.g., —OAc, —OC(O)$CF_3$), sulfonates (e.g., mesyl, tosyl), acetamides (e.g., —NHC(O)Me), carbamates (e.g., N(Me) C(O)Ot-Bu), phosphonates (e.g., —OP(O)$(OEt)_2$), water or alcohols (protic conditions), and the like.

In certain embodiments, substituents on any group (such as, for example, alkyl, alkenyl, alkynyl, aryl, aralkyl, heteroaryl, heteroaralkyl, cycloalkyl, heterocycloalkyl) can be at any atom of that group, wherein any group that can be substituted (such as, for example, alkyl, alkenyl, alkynyl, aryl, aralkyl, heteroaryl, heteroaralkyl, cycloalkyl, heterocycloalkyl) can be optionally substituted with one or more substituents (which may be the same or different), each replacing a hydrogen atom. Examples of suitable substituents include, but are not limited to alkyl, alkenyl, alkynyl, cycloalkyl, heterocycloalkyl, aralkyl, heteroaralkyl, aryl, heteroaryl, halogen, haloalkyl, cyano, nitro, alkoxy, aryloxy, hydroxyl, hydroxylalkyl, oxo (i.e., carbonyl), carboxyl, formyl, alkylcarbonyl, alkylcarbonylalkyl, alkoxycarbonyl, alkylcarbonyloxy, aryloxycarbonyl, heteroaryloxy, heteroaryloxycarbonyl, thio, mercapto, mercaptoalkyl, arylsulfonyl, amino, aminoalkyl, dialkylamino, alkylcarbonylamino, alkylaminocarbonyl, alkoxycarbonylamino, alkylamino, arylamino, diarylamino, alkylcarbonyl, or arylamino-substituted aryl; arylalkylamino, aralkylaminocarbonyl, amido, alkylaminosulfonyl, arylaminosulfonyl, dialkylaminosulfonyl, alkylsulfonylamino, arylsulfonylamino, imino, carbamido, carbamyl, thioureido, thiocyanato, sulfoamido, sulfonylalkyl, sulfonylaryl, or mercaptoalkoxy.

Compounds of the Invention

Compounds of the invention can be made by means known in the art of organic synthesis. Methods for optimizing reaction conditions, if necessary minimizing competing by-products, are known in the art. Reaction optimization and scale-up may advantageously utilize high-speed parallel synthesis equipment and computer-controlled microreactors (e.g. *Design And Optimization in Organic Synthesis*, $2^{nd}$ *Edition*, Carlson R, Ed, 2005; Elsevier Science Ltd.; Jähnisch, K et al, Angew. Chem. Int. Ed. Engl. 2004 43: 406; and references therein). Additional reaction schemes and protocols may be determined by the skilled artesian by use of commercially available structure-searchable database software, for instance, SciFinder® (CAS division of the American Chemical Society) and CrossFire Beilstein® (Elsevier MDL), or by appropriate keyword searching using an internet search engine such as Google® or keyword databases such as the US Patent and Trademark Office text database.

As can be appreciated by the skilled artisan, methods of synthesizing the compounds of the formulae herein will be evident to those of ordinary skill in the art, including in the schemes and examples herein. Additionally, the various synthetic steps may be performed in an alternate sequence or order to give the desired compounds. In addition, the solvents, temperatures, reaction durations, etc. delineated herein are for purposes of illustration only and one of ordinary skill in the art will recognize that variation of the reaction conditions can produce the desired compounds of the present invention.

The compounds herein may also contain linkages (e.g., carbon-carbon bonds) wherein bond rotation is restricted about that particular linkage, e.g. restriction resulting from the presence of a ring or double bond. Accordingly, all cis/trans and E/Z isomers are expressly included in the present invention. The compounds herein may also be represented in multiple tautomeric forms, in such instances, the invention expressly includes all tautomeric forms of the compounds described herein, even though only a single tautomeric form may be represented. All such isomeric forms of such compounds herein are expressly included in the present invention. All crystal forms and polymorphs of the compounds described herein are expressly included in the present invention. Also embodied are extracts and fractions comprising compounds of the invention. The term isomers is intended to include diastereoisomers, enantiomers, regioisomers, structural isomers, rotational isomers, tautomers, and the like. For compounds which contain one or more stereogenic centers, e.g., chiral compounds, the methods of the invention may be carried out with an enantiomerically enriched compound, a racemate, or a mixture of diastereomers.

The present invention also contemplates solvates (e.g., hydrates) of a compound of herein, compositions thereof, and their use in the treatment of a disease, disorder, or symptom thereof herein. As used herein, "solvate" refers to the physical association of a compound of the invention with one or more solvent or water molecules, whether organic or inorganic. In certain instances, the solvate is capable of isolation, for example, when one or more solvate molecules are incorporated in the crystal lattice of the crystalline solid.

Preferred enantiomerically enriched compounds have an enantiomeric excess of 50% or more, more preferably the compound has an enantiomeric excess of 60%, 70%, 80%, 90%, 95%, 98%, or 99% or more. In preferred embodiments, only one enantiomer or diastereomer of a chiral compound of the invention is administered to cells or a subject.

Methods of Treatment

This invention is directed towards compounds, compositions, and methods of treating diseases and disorders by use of the compounds and compositions delineated herein.

In other aspects, the invention provides a method of treating a disease, disorder, or symptom thereof in a subject, comprising administering to the subject any compound or composition delineated herein. In another aspect, the compound or composition is administered in an amount and under conditions sufficient to ameliorate the disease, disorder, or symptom thereof in a subject.

In another aspect, the disease, disorder, or symptom includes proliferative diseases and disorders, cancer, tumor growth, cancer of the colon, breast, bone, brain and others (e.g., osteosarcoma, neuroblastoma, colon adenocarcinoma), cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma).

In another aspect, the inhibition is in vitro. In another aspect, the inhibition is in vivo. In another aspect, the method further comprises administering the compound, or a pharmaceutically acceptable salt, solvate, hydrate or prodrug thereof, to a subject.

In other aspects, the invention provides a method of treating a subject suffering from or susceptible to a proliferative disease, the method comprising administering to the subject a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof.

In other aspects, the invention provides a method of treating a proliferative disease in a subject identified as in need thereof, the method comprising administering to the subject a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof.

In other aspects, the invention provides a method of treating a subject suffering from or susceptible to a proliferative disease, the method comprising administering to the subject a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof, such that said subject is treated for said proliferative disease.

In other aspects, the invention provides a method of treating a proliferative disease in a subject identified as in need thereof, the method comprising administering to the subject a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof, such that said subject is treated for said proliferative disease.

In other aspects, the invention provides a method of modulating the proliferation activity in a subject, comprising contacting the subject with a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof, in an amount and under conditions sufficient to modulate proliferation activity.

In one aspect, the invention provides a method of treating a subject suffering from or susceptible to a proliferation related disorder or disease, comprising administering to the subject a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof.

In another aspect, the invention provides a method of treating a subject suffering from or susceptible to a proliferation related activity related disorder or disease, wherein the subject has been identified as in need of treatment for a proliferation related disorder or disease, comprising administering to said subject in need thereof, a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof, such that said subject is treated for said disorder.

In another aspect, the invention provides a method of treating a subject suffering from or susceptible to a cell proliferation related disorder or disease, wherein the subject has been identified as in need of treatment for a cell proliferation related disorder or disease, comprising administering to said subject in need thereof, a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof, such that cell proliferation in said subject is modulated (e.g., down regulated). In another aspect, the compounds or compositions delineated herein preferentially target cancer cells over nontransformed cells.

In another aspect, the proliferative disease is cancer.

In another aspect, the cancer is multiple myeloma, lymphoma, chronic lymphocytic leukemia (CLL), acute myelogenous leukemia (AML), large granular lymphocyte leukemia (LGL), sarcoma, lung cancer, breast cancer, renal cancer, prostate cancer, pancreatic cancer, melanoma, colon carcinoma, gastric carcinoma, cervical cancer, ovarian cancer, liver cancer, or head and neck cancer.

In a specific aspect, the invention provides a method of treating cancer, tumor growth, cancer of the colon, breast, bone, brain and others (e.g., osteosarcoma, neuroblastoma, colon adenocarcinoma), comprising administering to said subject in need thereof, an effective amount of any compound or seaweed extract delineated herein, and pharmaceutically acceptable salts thereof. Other cancers that may be treated by the compositions and methods of the invention include cardiac cancer (e.g., sarcoma, myxoma, rhabdomyoma, fibroma, lipoma and teratoma); lung cancer (e.g., bronchogenic carcinoma, alveolar carcinoma, bronchial adenoma, sarcoma, lymphoma, chondromatous hamartoma, mesothelioma); various gastrointestinal cancer (e.g., cancers of esophagus, stomach, pancreas, small bowel, and large bowel); genitourinary tract cancer (e.g., kidney, bladder and urethra, prostate, testis; liver cancer (e.g., hepatoma, cholangiocarcinoma, hepatoblastoma, angiosarcoma, hepatocellular adenoma, hemangioma); bone cancer (e.g., osteogenic sarcoma, fibrosarcoma, malignant fibrous histiocytoma, chondrosarcoma, Ewing's sarcoma, malignant lymphoma, cutaneous T-cell lymphoma, multiple myeloma, malignant giant cell tumor chordoma, osteochronfroma, benign chondroma, chondroblastoma, chondromyxofibroma, osteoid osteoma and giant cell tumors); cancers of the nervous system (e.g., of the skull, meninges, brain, and spinal cord); gynecological cancers (e.g., uterus, cervix, ovaries, vulva, vagina); hematologic cancer (e.g., cancers relating to blood, Hodgkin's disease, non-Hodgkin's lymphoma); skin cancer (e.g., malignant melanoma, basal cell carcinoma, squamous cell carcinoma, Karposi's sarcoma, moles dysplastic nevi, lipoma, angioma, dermatofibroma, keloids, psoriasis); and cancers of the adrenal glands (e.g., neuroblastoma). Other diseases and disorders that can be treated include the treatment of inflammatory disorders, neurodegenerative diseases, protozoal and latent viral infections, and (fibro)proliferative disorders.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method).

Pharmaceutical Compositions

In one aspect, the invention provides a pharmaceutical composition comprising the compound and a pharmaceutically acceptable carrier.

In another embodiment, the invention provides a pharmaceutical composition further comprising an additional therapeutic agent. In another embodiment, the invention provides a pharmaceutical composition further comprising an additional therapeutic agent. In a further embodiment, the additional therapeutic agent is an anti-cancer agent, chemotherapeutic agent, an anti-angiogenesis agent, cytotoxic agent, an anti-proliferation agent. In a further embodiment, the additional therapeutic agent is an anti-cancer agent, chemotherapeutic agent, an anti-angiogenesis agent, cytotoxic agent, or an anti-proliferation agent.

In one aspect, the invention provides a kit comprising an effective amount of a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof, in unit dosage form, together with instructions for administering the compound to a subject suffering from or susceptible to a proliferative disease, cancer (including diseases herein), solid tumor, angiogenesis, etc.

In one aspect, the invention provides a kit comprising an effective amount of a compound of any of the formulae herein (e.g., formulae (I)-(II), formulae (I)-(V)), or a pharmaceutically acceptable salt, solvate, hydrate or prodrug thereof, or a pharmaceutical composition comprising a compound of any of the formulae herein (e.g., formulae (I)-(II), formulae (I)-(V)), or a pharmaceutically acceptable salt, solvate, hydrate or prodrug thereof, in unit dosage form, together with instructions for administering the compound to a subject suffering from or susceptible to a cell proliferation disease or disorder, including cancer, solid tumor, angiogenesis, etc.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The invention also provides a pharmaceutical composition, comprising an effective amount a compound described herein and a pharmaceutically acceptable carrier. In an embodiment, compound is administered to the subject using a pharmaceutically-acceptable formulation, e.g., a pharmaceutically-acceptable formulation that provides sustained delivery of the compound to a subject for at least 12 hours, 24 hours, 36 hours, 48 hours, one week, two weeks, three weeks, or four weeks after the pharmaceutically-acceptable formulation is administered to the subject.

Actual dosage levels and time course of administration of the active ingredients in the pharmaceutical compositions of this invention may be varied so as to obtain an amount of the active ingredient which is effective to achieve the desired therapeutic response for a particular patient, composition, and mode of administration, without being toxic (or unacceptably toxic) to the patient.

In use, at least one compound according to the present invention is administered in a pharmaceutically effective amount to a subject in need thereof in a pharmaceutical carrier by intravenous, intramuscular, subcutaneous, or intracerebro ventricular injection or by oral administration or topical application. In accordance with the present invention, a compound of the invention may be administered alone or in conjunction with a second, different therapeutic. By "in conjunction with" is meant together, substantially simultaneously or sequentially. In one embodiment, a compound of the invention is administered acutely. The compound of the invention may therefore be administered for a short course of treatment, such as for about 1 day to about 1 week. In another embodiment, the compound of the invention may be administered over a longer period of time to ameliorate chronic disorders, such as, for example, for about one week to several months depending upon the condition to be treated.

By "pharmaceutically effective amount" as used herein is meant an amount of a compound of the invention, high enough to significantly positively modify the condition to be treated but low enough to avoid serious side effects (at a reasonable benefit/risk ratio), within the scope of sound medical judgment. A pharmaceutically effective amount of a compound of the invention will vary with the particular goal to be achieved, the age and physical condition of the patient being treated, the severity of the underlying disease, the duration of treatment, the nature of concurrent therapy and the specific organozinc compound employed. For example, a therapeutically effective amount of a compound of the invention administered to a child or a neonate will be reduced proportionately in accordance with sound medical judgment. The effective amount of a compound of the invention will thus be the minimum amount which will provide the desired effect.

A decided practical advantage of the present invention is that the compound may be administered in a convenient manner such as by intravenous, intramuscular, subcutaneous, oral or intra-cerebroventricular injection routes or by topical application, such as in creams or gels. Depending on the route of administration, the active ingredients which comprise a compound of the invention may be required to be coated in a material to protect the compound from the action of enzymes, acids and other natural conditions which may inactivate the compound. In order to administer a compound of the invention by other than parenteral administration, the compound can be coated by, or administered with, a material to prevent inactivation.

The compound may be administered parenterally or intraperitoneally. Dispersions can also be prepared, for example, in glycerol, liquid polyethylene glycols, and mixtures thereof, and in oils.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage. The carrier can be a solvent or dispersion medium containing, for example, water, DMSO, ethanol, polyol (for example, glycerol, propylene glycol, liquid polyethylene glycol, and the like), suitable mixtures thereof and vegetable oils. The proper fluidity can be maintained, for example, by the use of a coating such as lecithin, by the maintenance of the required particle size in the case of dispersion. In many cases it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the compound of the invention in the required amount in the appropriate solvent with various of the other ingredients enumerated above, as required, followed by filtered sterilization. Generally, dispersions are prepared by incorporating the various sterilized compounds into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yields a powder of the active ingredient plus any additional desired ingredient from previously sterile-filtered solution thereof.

For oral therapeutic administration, the compound may be incorporated with excipients and used in the form of ingestible tablets, buccal tablets, troches, capsules, elixirs, suspensions, syrups, wafers, and the like. Compositions or preparations according to the present invention are prepared so that an oral dosage unit form contains compound concentration sufficient to treat a disorder in a subject.

Some examples of substances which can serve as pharmaceutical carriers are sugars, such as lactose, glucose and sucrose; starches such as corn starch and potato starch; cellulose and its derivatives such as sodium carboxymethylcellulose, ethylcellulose and cellulose acetates; powdered tragancanth; malt; gelatin; talc; stearic acids; magnesium stearate; calcium sulfate; vegetable oils, such as peanut oils, cotton seed oil, sesame oil, olive oil, corn oil and oil of *theobroma*; polyols such as propylene glycol, glycerine, sorbitol, manitol, and polyethylene glycol; agar; alginic acids; pyrogen-free water; isotonic saline; and phosphate buffer solution; skim milk powder; as well as other non-toxic compatible substances used in pharmaceutical formulations such as Vitamin C, estrogen and *echinacea*, for example. Wetting agents and lubricants such as sodium lauryl sulfate, as well as coloring agents, flavoring agents, lubricants, excipients, tableting agents, stabilizers, anti-oxidants and preservatives, can also be present.

Topical administration of the pharmaceutical compositions of this invention is especially useful when the desired treatment involves areas or organs readily accessible by topical application. For topical application topically to the skin, the pharmaceutical composition should be formulated with a suitable ointment, lotion, or cream containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol, and water. The pharmaceutical compositions of this invention may also be topically applied to the lower intestinal tract by rectal suppository formulation or in a suitable enema formulation. Topically-transdermal patches and iontophoretic administration are also included in this invention.

For topical administration, the active compound(s), extracts, enriched extracts, or prodrug(s) can be formulated as solutions, gels, ointments, creams, suspensions, and the like.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The present invention will now be demonstrated using specific examples that are not to be construed as limiting.

Example 1

Synthesis

The solvents and reagents used in the present study were purchased from commercial suppliers and were used as received. Progress of the chemical reactions was monitored by thin-layer chromatography on silica gel 60-F254 aluminum plates and detected under UV light. Silica gel for flash silica gel column chromatography was purchased from Sigma-Aldrich Chemical Co. (Milwaukee, WI). Proton nuclear magnetic resonance spectra were obtained with Bruker Avance 300 (300 MHz) or 400 (400 MHz) NMR spectrometer (Billerica, MA). Agilent LC/MSD TOF system G3250AA was used for the mass spectra measurements.

The synthesis of the compounds can be accomplished by procedures known to one of skill in the art, and are also illustrated in the schemes and figures herein, or compounds (including starting materials, reagents, intermediates, etc.) are commercially available.

Compound Series 15 Synthetic Routes

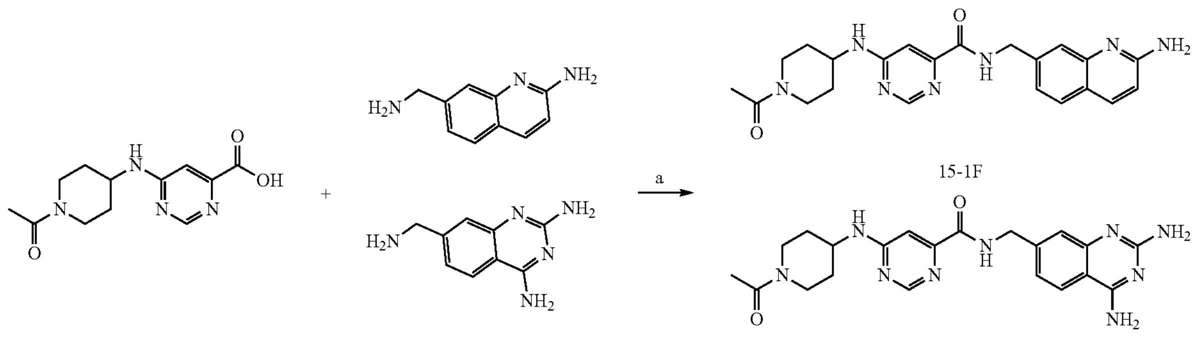

15-1F 15-2F

Reagents and conditions: (a) EDCI, HOBt, $Et_3N$, DMF.

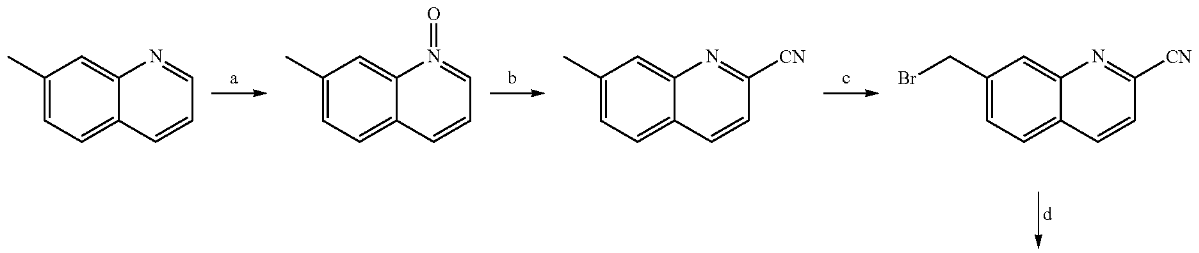

-continued
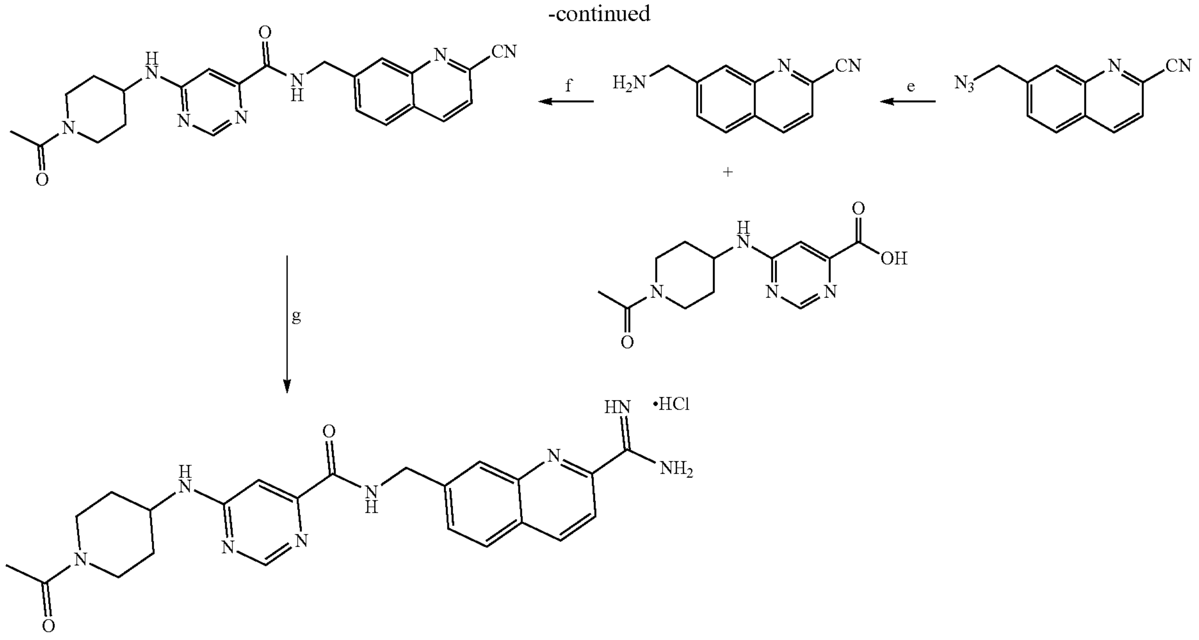
15-8F
Reagents and conditions: (a) 3-chloro-benzenecarboperoxoic acid, DCM; (b) N,N-Dimethylcarbamoyl chloride, TMSCN, DCM; (c) NBS, AIBN, $CH_3CN$, reflux, (d) $NaN_3$, DMF, room temperature; (e) $H_2$, Pd/C, EtOAc; (f) EDCI, DMAP, $Et_3N$, DMF; (g) HCl/EtOH, $(NH_4)_2CO_3$.
Compound Series 11 Synthetic Routes
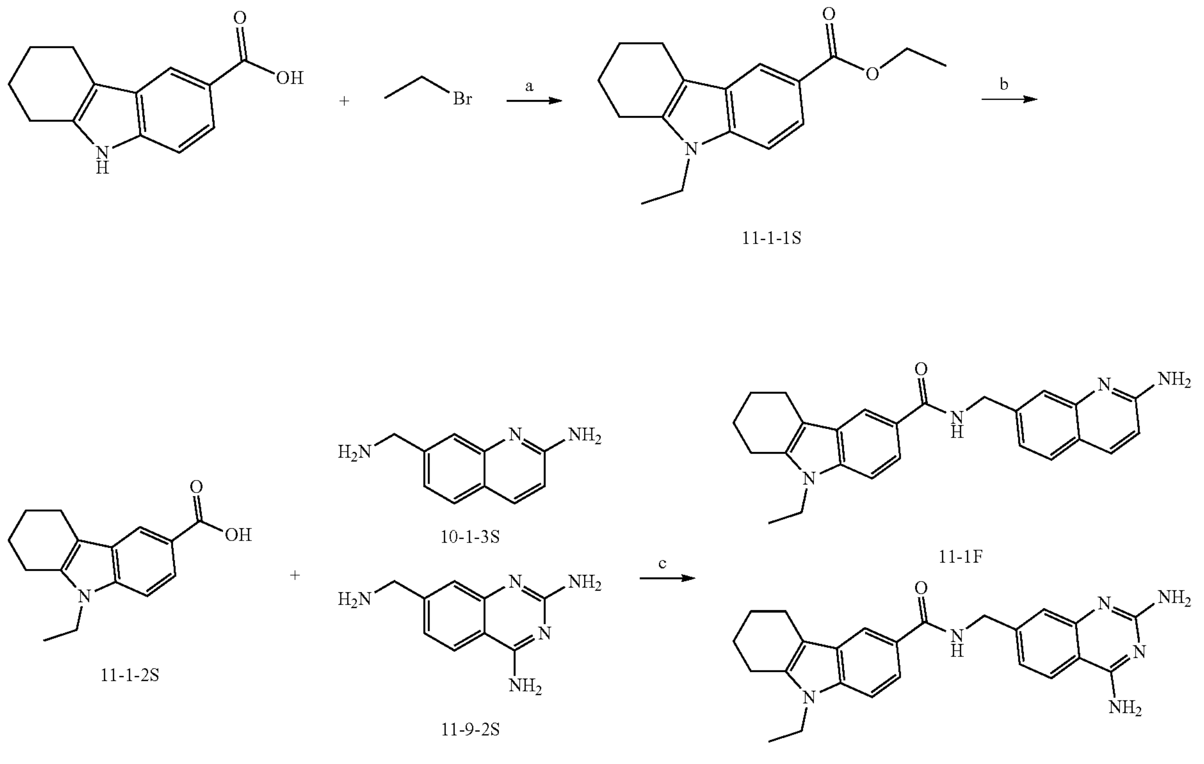
11-1-1S
11-1-2S
10-1-3S
11-9-2S
11-1F
11-9F
Reagents and conditions: (a) KOH/DMF; (b) NaOH, ethanol/$H_2O$; (c) EDCI, DMAP, $Et_3N$, DMF.

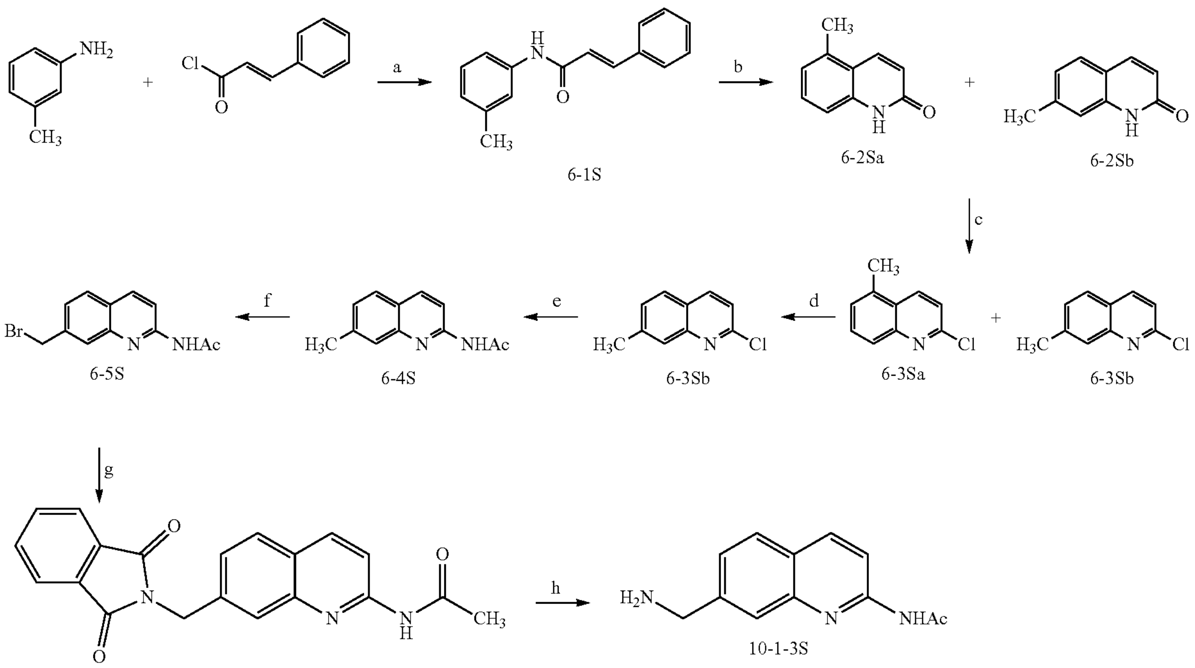

6-1S 6-2Sa 6-2Sb 6-3Sa 6-3Sb 6-4S 6-5S 10-1-3S

Reagents and conditions: (a) Pyridine; (b) $AlCl_3$, PhCl, 90 °C; (c) $POCl_3$, reflux; (d) fractional crystallization from i-PrOH after isolation; (e) $AcNH_2$, $K_2CO_3$, reflux (~230 °C); (f) NBS, $(PhCO_2)_2$, benzene, reflux; (f) DMF, potassium phtalimide; (g) hydrazine hydrate, methanol, reflux.

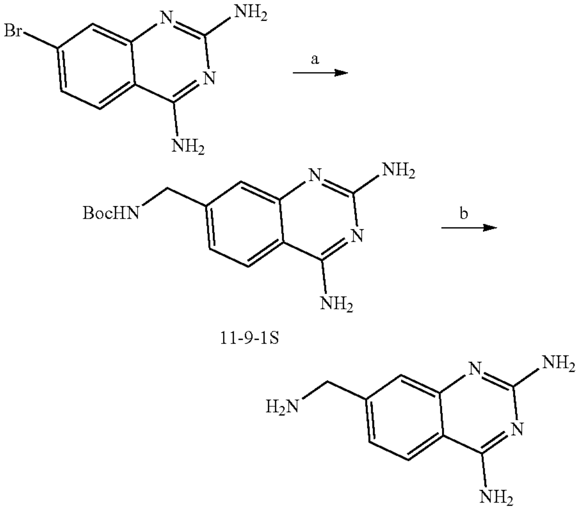

11-9-1S 11-9-2S

Reagents and conditions: (a) potassium tert-butyl N-[(trifluorolambda-4-boranyl)methyl]carbamate, $Pd(OAc)_2$, XPhos, $Cs_2CO_3$, dioxane; (b) HCl in methanol.

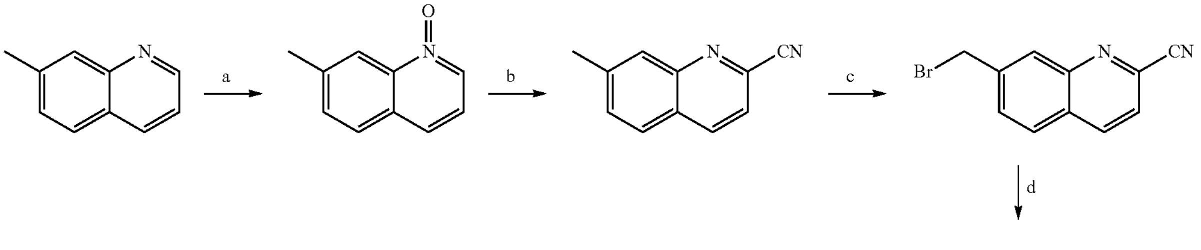

-continued

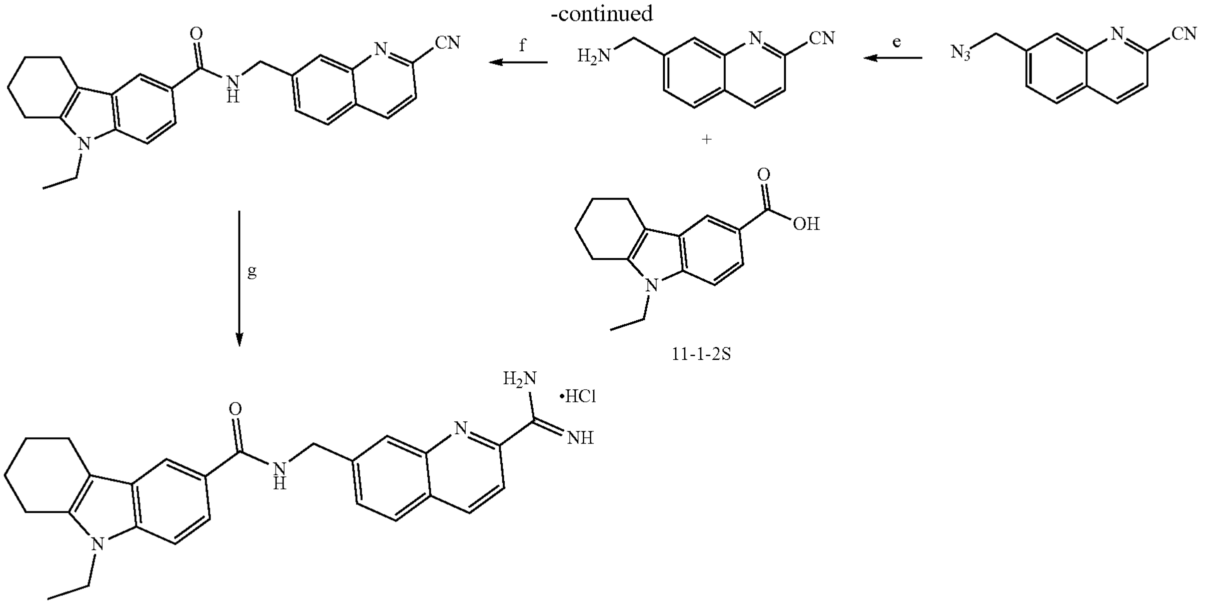

11-1-2S 11-10F

Reagents and conditions: (a) 3-chloro-benzenecarboperoxoic acid, DCM; (b) N,N-Dimethylcarbamoyl chloride, TMSCN, DCM; (c) NBS, AIBN, $CH_3CN$, reflux, (d) $NaN_3$, DMF, room temperature; (e) $H_2$, Pd/C, EtOAc; (f) EDCI, DMAP, $Et_3N$, DMF; (g) HCl/EtOH, $(NH_4)_2CO_3$.

Example 2

Materials and Methods

Protein expression and purification. The PRMT5:MEP50 protein complex was co-expressed in sf9 insect cells by Bac-to-Bac expression system and then purified by affinity chromatography and gel filtration.

In silico molecular docking. Binding modes of designed small molecules are predicted by Autodock4.

Surface Plasmon Resonance (SPR) binding analysis. Direct and competitive protein-ligand binding studies were performed on Biacore X100. Purified PRMT5: MEP50 was covalently attached to the CM5 sensor chip by amine coupling.

Enzymatic inhibition assay. The enzymatic inhibition activity of designed compounds was determined by AlphaLISA assay and the mechanism of inhibition study was performed by MTase-Glo assay.

Cancer cell lines. MCF-7 (breast cancer cell line), MDA-MB-231 (triple negative breast cancer cell line) and MV4-11 (MLL-rearranged acute myeloid leukemia cell line).

Cell proliferation assay. Anti-proliferative effects of designed molecules were tested in different cancer cell lines by MTT assay.

Western blot. Protein symmetric dimethylation level was assessed in MV4-11 cell line by pan-SDMA antibody and H4R3me2s antibody.

Cell apoptosis analysis. Apoptotic effect was evaluated by flow cytometry in MV4-11 cell line.

The results provided conflicting data about the binding mechanism of the designed molecules. SPR binding results suggest that the parental compounds bind to PRMT5 directly while MOI study reveals that the inhibition activity relies on cofactor binding, which is surprisingly consistent with the SPR results of 1-BUT-1F. Structural characterizations are necessary to confirm the actual binding mode of designed molecules.

Binding kinetics profiles are different between well-characterized cofactor analogs and our designed molecules. The fast-on fast-off binding mode suggests that they may not be strong binders. It is possible that the binding of designed molecules did not stabilize the critical loop at the active site which is flexible in the apo form of PRMT5.

Selectivity among other types of PRMTs as well as cell toxicity and off-target effects need to be studied for the designed molecules.

While the current two classes of inhibitors have their own limitation, it is worthwhile to design small molecule exhibiting novel inhibition mechanism. Our results show that the designed molecule 1-BUT-1F bind to MTA-bound PRMT5 with a higher binding affinity ($K_D$=2.65 μM) than EPZ015666 ($K_D$=20.4 μM, reported by RBC), which makes it feasible to design MTA-dependent substrate-competitive inhibitors at the substrate binding site. This is extremely useful for MTAP-deleted cancers where MTA is overexpressed.

Based on the docking mode in the human PRMT 5 crystal structure, fragment-based and structure-based design has led to a series of 1,2,3,4-tetrahydrocarbazole derivatives. Different from the previously reported compounds which are substrate site competitor or nucleoside analogues, our compounds based on 1,2,3,4-tetrahydrocarbazole target the cofactor site of PRMT 5. Compared to the previous reported compound CMP5, the binding affinity and efficacy of new compounds have been improved. Furthermore, the MTT assay shows that our compounds are effective in the MCF-7 cell line.

MTase-Glo Enzymatic Assay Protocol

Inhibitor compounds are serial diluted by 5-fold to the desired concentrations in DMSO. Inhibitors are added into reaction buffer (30 mM Tris-HC at pH 7.4, 500 mM NaCl, 2 mM MgCl2, 2 mM TCEP, 0.1% (wt/vol) BSA and 0.01% (vol/vol) Tween-20) with final DMSO concentration at 2% (vol/vol). The enzymatic inhibition assay is performed in a solid white low-volume 384-well plate (Greiner, #7784075)

with total reaction volume of 16 μl and in the presence of 100 nM PRMT5:MEP50 enzymes, 10 μM SAM (Sigma-Aldrich, A4377), 2 μM substrate histone H4 (1-21) (ANASPEC, #AS-62499) and test compounds at indicated concentrations. Reactions without enzyme are conducted as negative control and reactions without compound are performed as positive control in every experiment. Methyltransferase reaction was started by adding 4 μl of SAM/H4 substrate mixture to each well that contains 8 μl enzyme and 4 μl test compound which are pre-mixed and incubated for 10 min. The reaction is performed at room temperature for 60 min followed by the addition of 4 μl 5×MTase-Glo Reagent to produce SAH and concomitantly convert it to ADP. Mix the plate by shaking for 2 min, and incubate at room temperature for 30 min. Then, 20 μl room-temperature MTase-Glo Detection Solution is added and mixed well before incubating for another 30 min and recording luminescence. Luminescence is measured using the Synergy Neo2 HTS multimode microplate reader (BioTek). Each data point represents the average of three replicates; the error bars represent the standard deviation. Data are analyzed in GraphPad Prism 8. For inhibitor studies, $IC_{50}$ is determined by nonlinear regression (curve fit) using sigmoidal dose response (variable slope). RLU: Relative luminescence unit.

| MTase-Glo enzymatic inhibition | | |
|---|---|---|
| | Compounds | |
| | 15-1F | 15-2F |
| $IC_{50}$ | 218.5 nM | 151.8 nM |

| MTase-Glo enzymatic inhibition | | | |
|---|---|---|---|
| | Compounds | | |
| | 11-1F | 11-2F | 11-9F |
| $IC_{50}$ | 1.342 μM | 0.883 μM | 0.183 μM |

EMBODIMENTS

The following are embodiments of the invention:

1. A compound of Formula (III), or a pharmaceutically acceptable salt, solvate, hydrate or prodrug thereof: Formula III

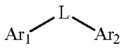

wherein, $Ar_1$ is a monocyclic or bicyclic aromatic ring having 0-4 heteroatoms independently selected from nitrogen, oxygen, and sulfur, wherein $Ar_1$ is substituted with 0, 1, 2, 3, 4, or 5 $R_Y$ groups, as valency permits; each $R^y$ is independently selected from the group consisting of halo, —CN, —$NO_2$, optionally substituted aliphatic, optionally substituted carbocyclyl, optionally substituted aryl, optionally substituted heterocyclyl, optionally substituted heteroaryl, —$OR^A$, —$N(R^B)_2$, —$SR^A$, —$C(=O)R^A$, —$C(O)OR^A$, —$C(O)SR^A$, —$C(O)N(R^B)_2$, —$C(O)N(R^B)N(R^B)_2$, —$OC(O)R^A$, —$OC(O)N(R^B)_2$, —$NR^BC(O)R^A$, —$NR^BC(O)N(R^B)_2$, —$NR^BC(O)N(R^B)N(R^B)_2$, —$NR^BC(O)OR^A$, —$SC(O)R^A$, —$C(=NR^B)R^A$, —$C(=NNR^B)R^A$, —$C(=NORA)R^A$, —$C(=NR^B)N(R^B)_2$, —$NR^BC(=NR^B)R^B$, —$C(=S)R^A$, —$C(=S)N(R^B)_2$, —$NR^BC(=S)R^A$, —$S(O)R^A$, —$OS(O)_2R^A$, —$SO_2R^A$, —$NR^BSO_2R^A$, or —$SO_2N(R^B)_2$;

each $R^A$ is independently selected from the group consisting of hydrogen, optionally substituted aliphatic, optionally substituted carbocyclyl, optionally substituted heterocyclyl, optionally substituted aryl, and optionally substituted heteroaryl;

each $R^B$ is independently selected from the group consisting of hydrogen, optionally substituted aliphatic, optionally substituted carbocyclyl, optionally substituted heterocyclyl, optionally substituted aryl, and optionally substituted heteroaryl, or two $R^B$ groups are taken together with their intervening atoms to form an optionally substituted heterocyclic ring, which may be optionally substituted with 0, 1, 2, 3, 4, or 5 $R^x$ groups;

each $R^A$ and $R^B$ can be optionally substituted by one or more independent $R^5$, $R^6$, $R^7$, and $R^8$;

each $R^5$, $R^6$, $R^7$, and $R^8$ is independently hydrogen, halo, or optionally substituted aliphatic;

each $R^x$ is independently selected from the group consisting of halo, —CN, optionally substituted aliphatic, —OR', and —N(R")$_2$;

each R' is independently hydrogen or optionally substituted aliphatic;

each R" is independently hydrogen or optionally substituted aliphatic, or two R" are taken together with their intervening atoms to form a heterocyclic ring; and n is 0, 1, 2, 3, 4, 5, 6, 7, 8, 9, or 10, as valency permits;

L is

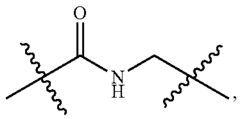,
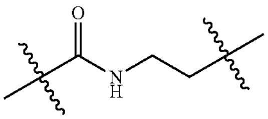,

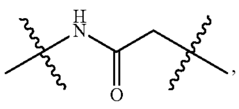, or
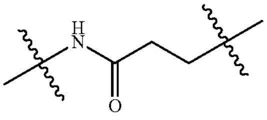;

and $Ar_2$ is any one of the following groups:

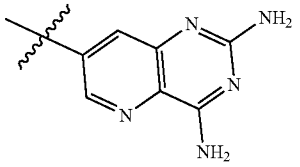

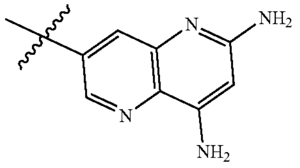

-continued
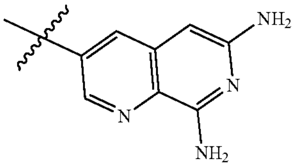
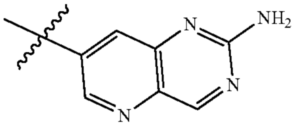
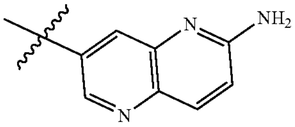
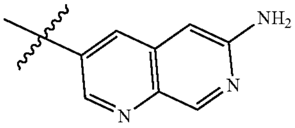
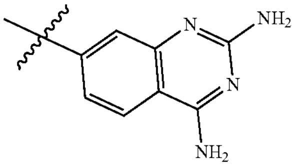
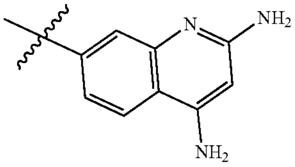
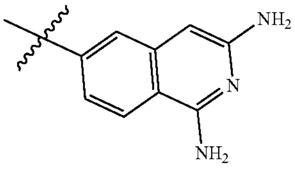
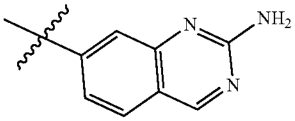
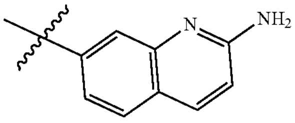
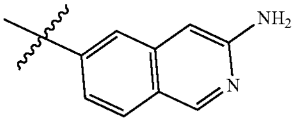
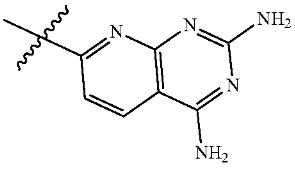
-continued
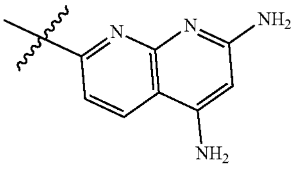
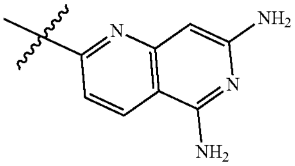
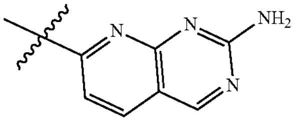
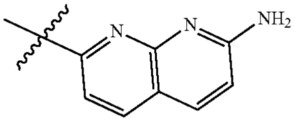
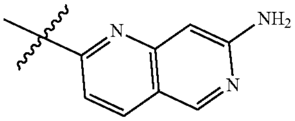
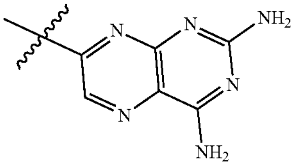
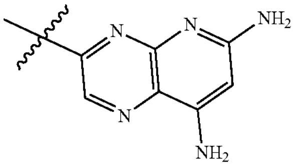
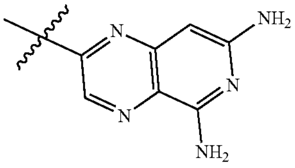
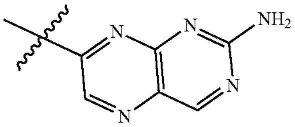
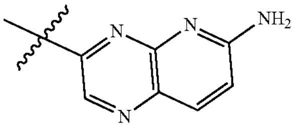
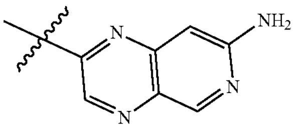

-continued
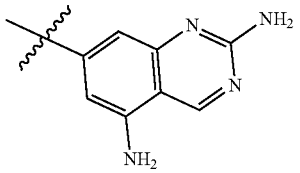
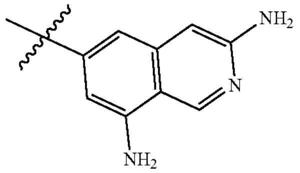
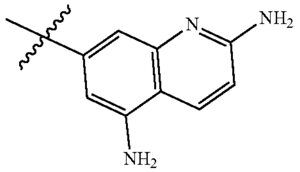
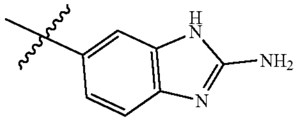
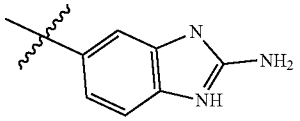
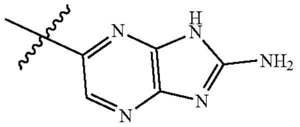
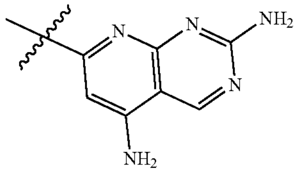
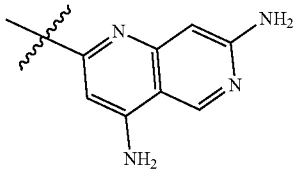
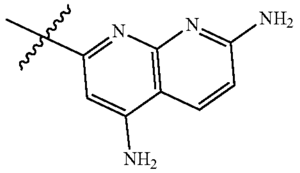
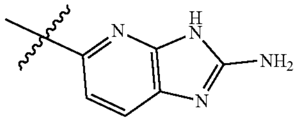
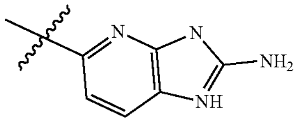
-continued
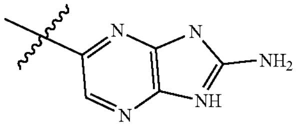
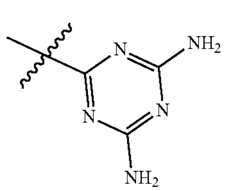
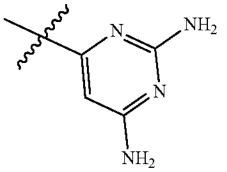
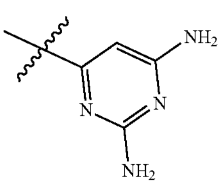
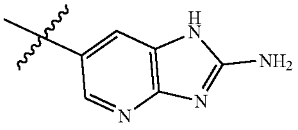
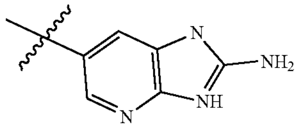
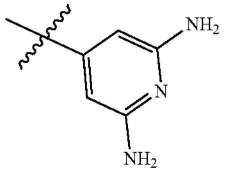
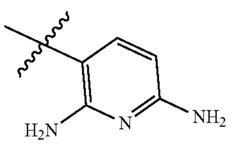
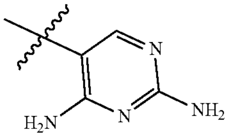
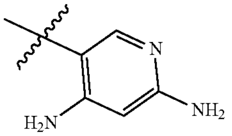
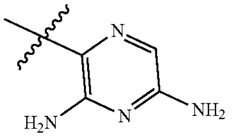
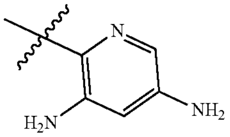
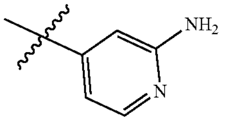
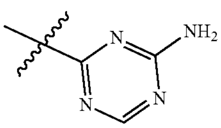
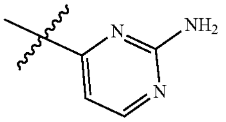
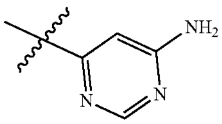
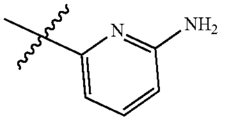
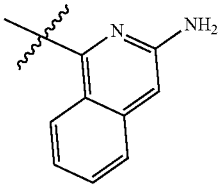
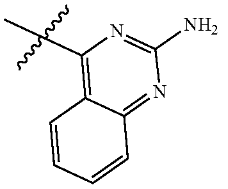

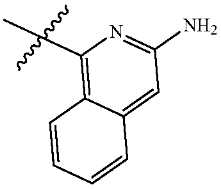
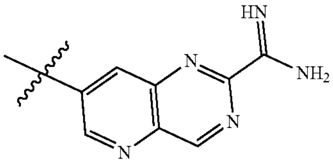
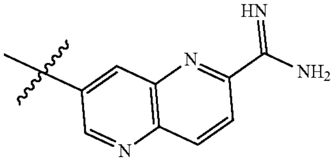
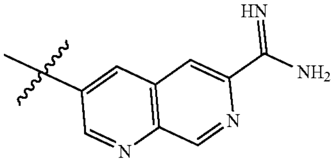
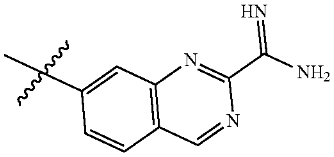
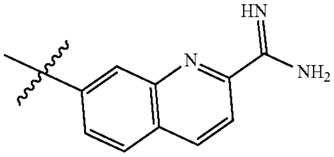
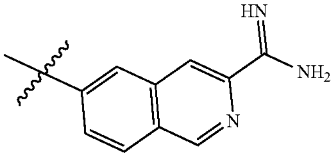
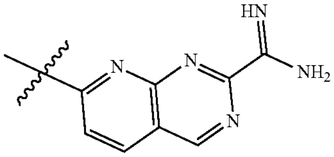
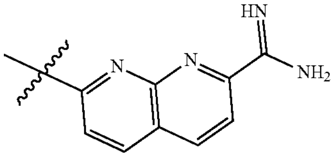
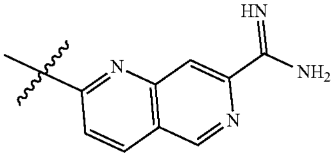
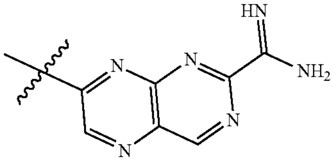
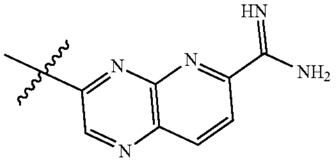
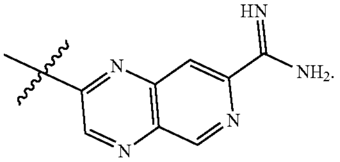
2. The compounds of Formula III in embodiment 1, or a pharmaceutically acceptable salt, solvate, hydrate or prodrug thereof, are those wherein:
$Ar_1$ is any one of the following groups,
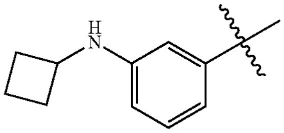
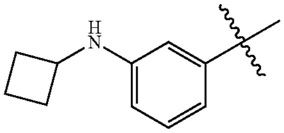
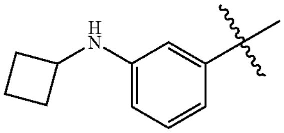
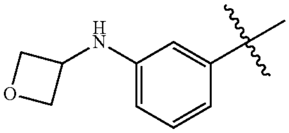
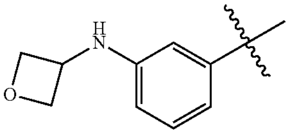
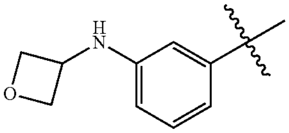
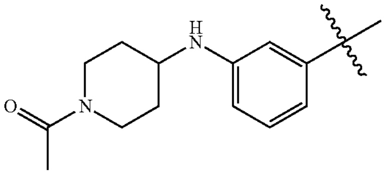
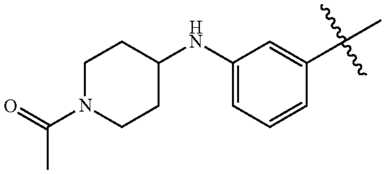
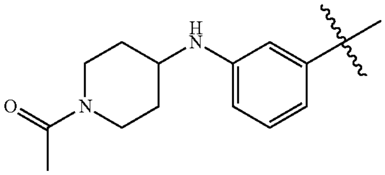

-continued
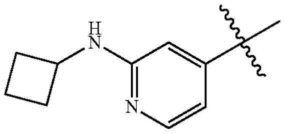 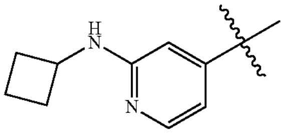
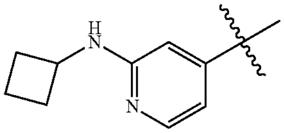
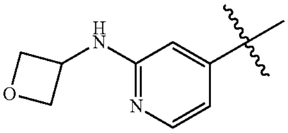
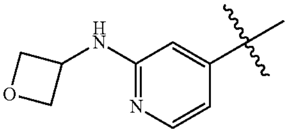
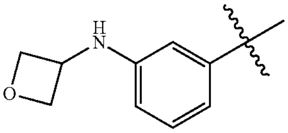
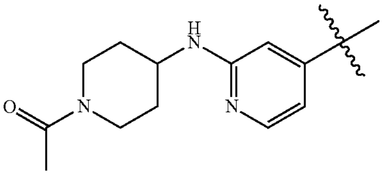
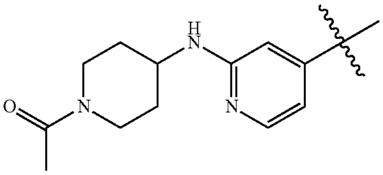
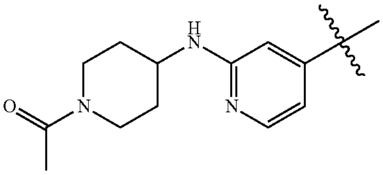
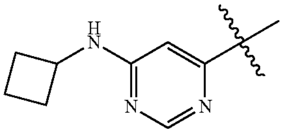 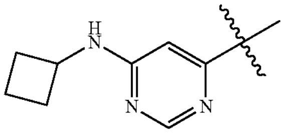
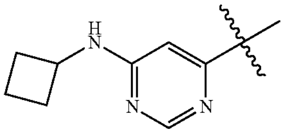
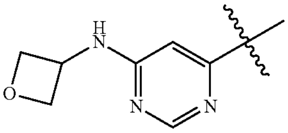
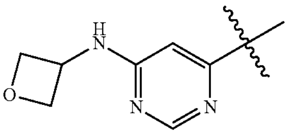
-continued
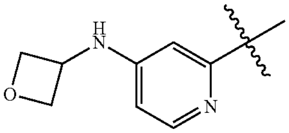
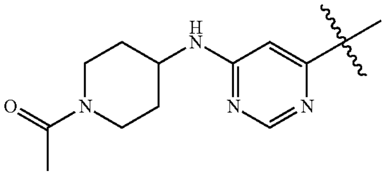
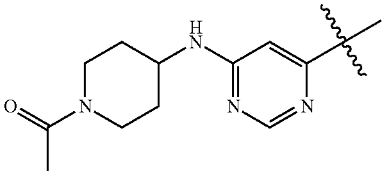
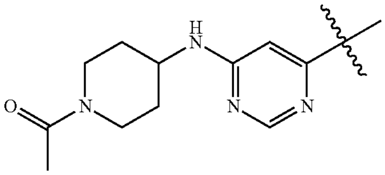
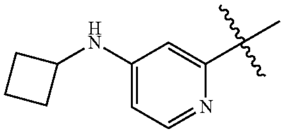 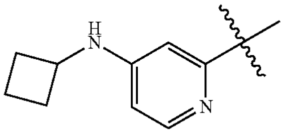
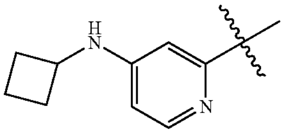
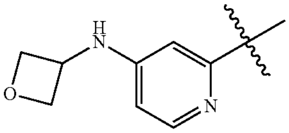
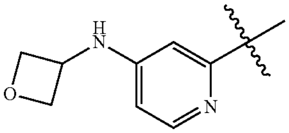
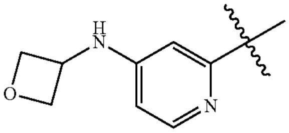
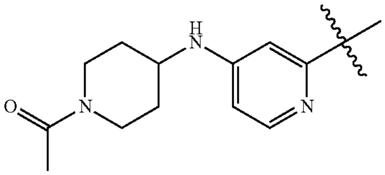
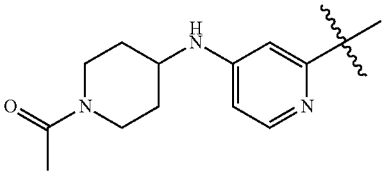

-continued

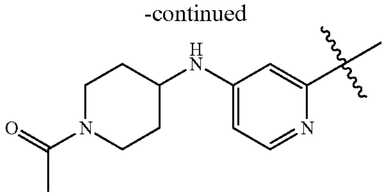

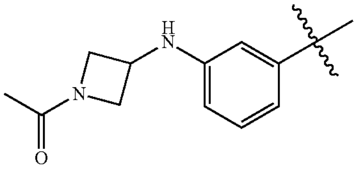

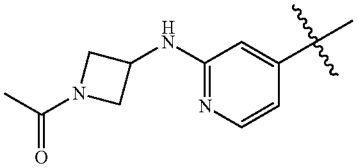

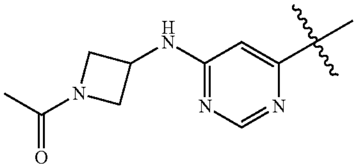

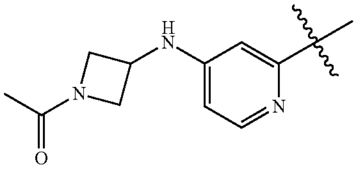

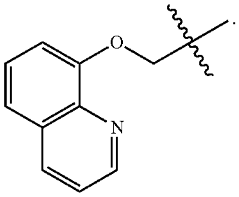

3. The compound of any of embodiments 1-2, wherein $R_1$ is

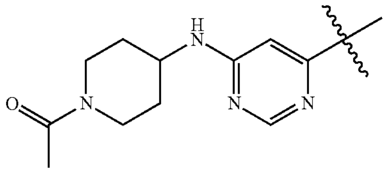

, or a pharmaceutically acceptable salt, solvate, hydrate or prodrug thereof.

4. The compound of any of embodiments 1-3, wherein L is

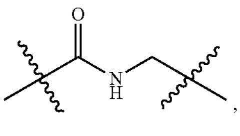 [SMILES: *CNC(*)=O]

, or a pharmaceutically acceptable salt, solvate, hydrate or prodrug thereof.

5. The compound of any of embodiments 1-4, wherein $Ar_2$ is

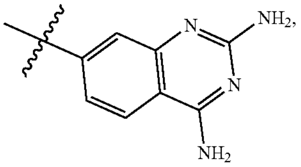

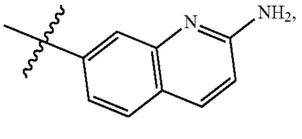

or

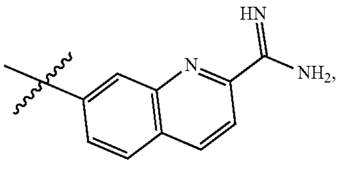

or a pharmaceutically acceptable salt, solvate, hydrate or prodrug thereof.

6. The compound ofany of embodiments 1-5, or a pharmaceutically acceptable salt, solvate, hydrate or prodrug thereof, that is one of the following:

15-1F

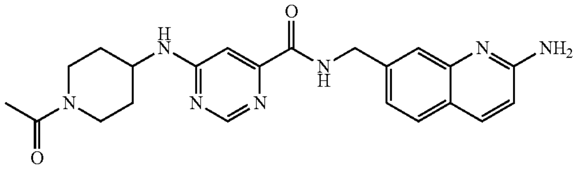

15-2F

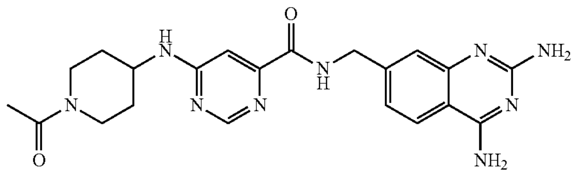

15-8F

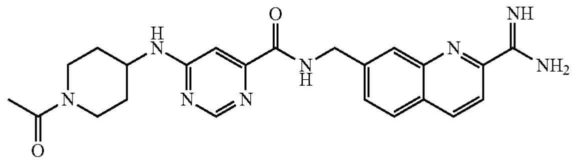

or a pharmaceutically acceptable salt, solvate, hydrate or prodrug thereof.

7. A compound, or a pharmaceutically acceptable salt, solvate, hydrate or prodrug thereof, represented by Formula (IV) or (V):
Formula IV
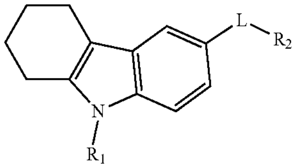
Formula V
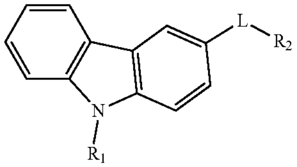
wherein
each $R_1$ is independently one of:
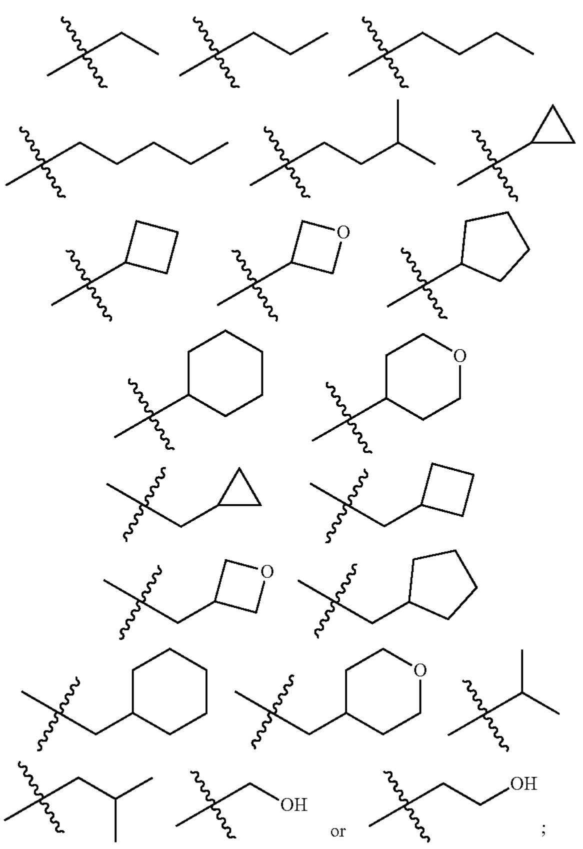
or ;
Each L is independently:
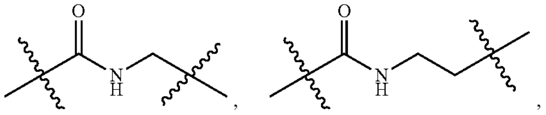
, ,
-continued
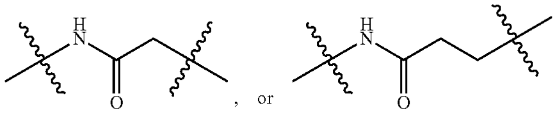
, or ;
Each $R_2$ is independently one of:
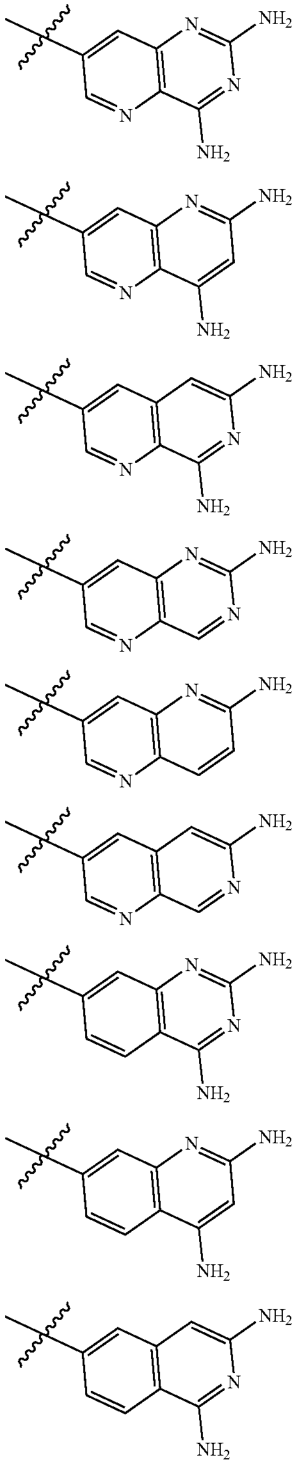

-continued
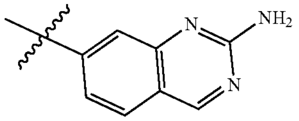
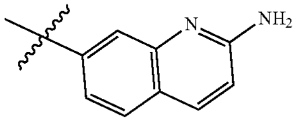
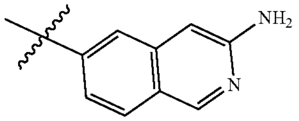
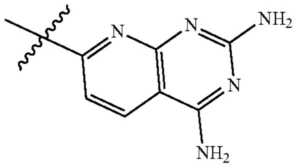
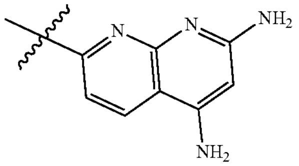
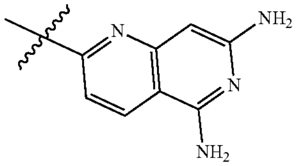
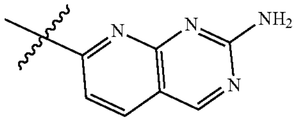
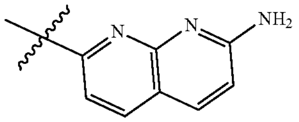
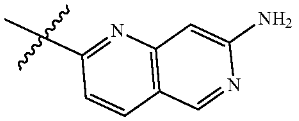
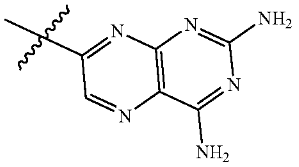
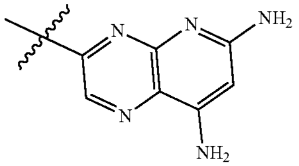
-continued
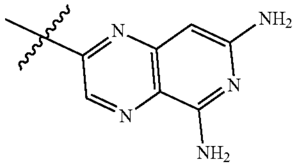
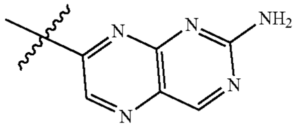
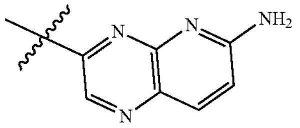
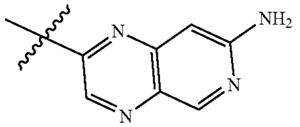
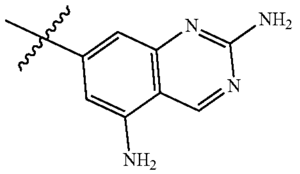
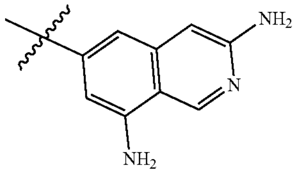
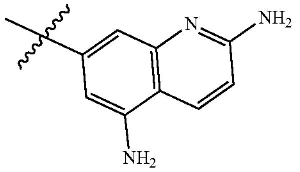
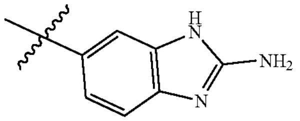
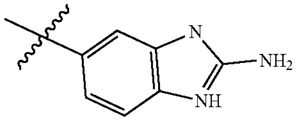
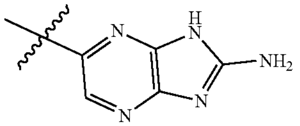
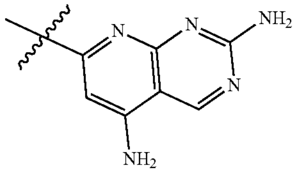

-continued
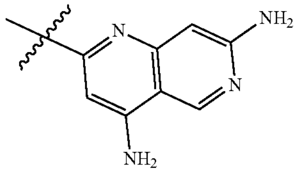
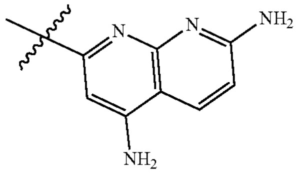
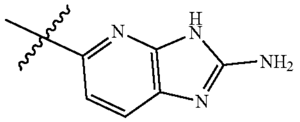
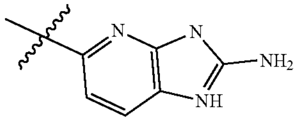
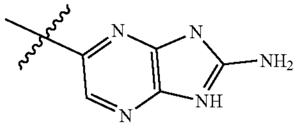
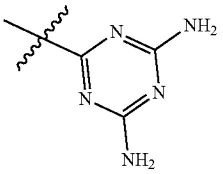
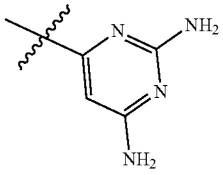
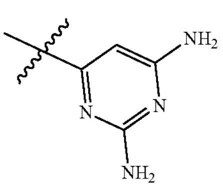
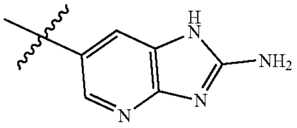
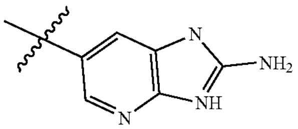
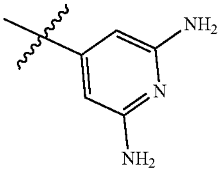
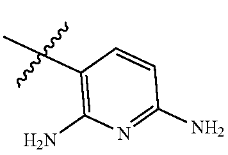
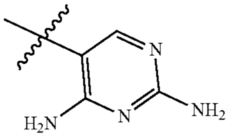
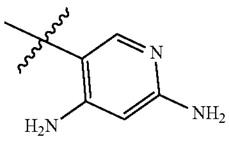
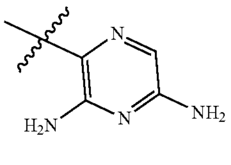
-continued
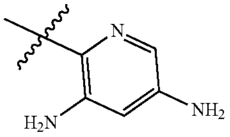
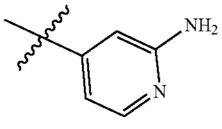
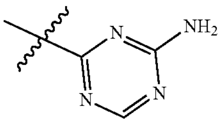
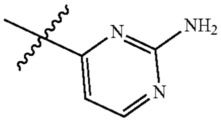
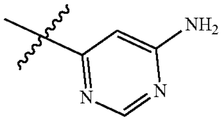
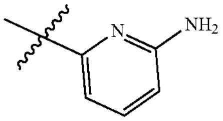
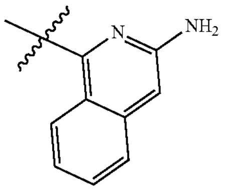
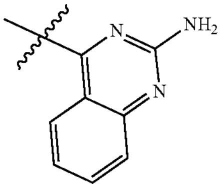
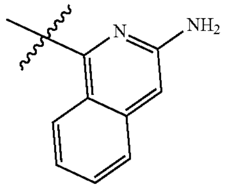
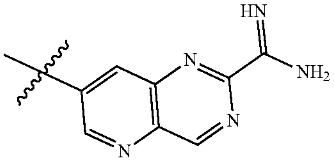
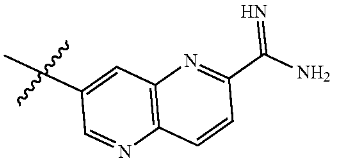
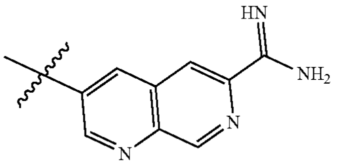
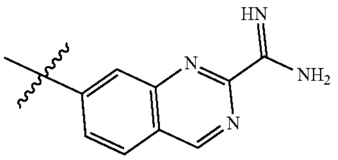
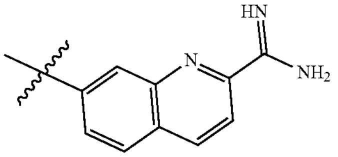
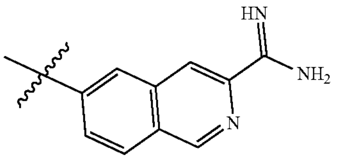

-continued

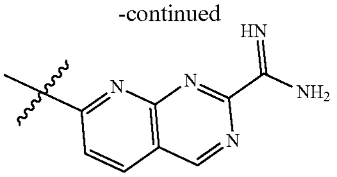

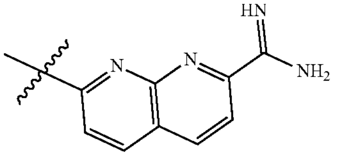

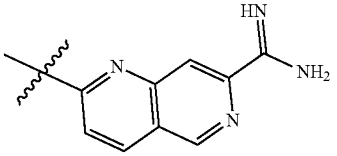

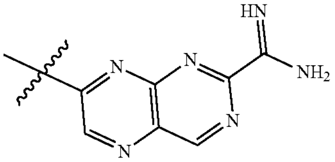

and

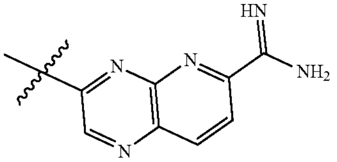

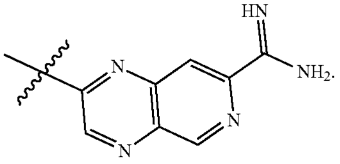

8. The compound, or a pharmaceutically acceptable salt, solvate, hydrate or prodrug thereof, of embodiment 7, wherein each $R_1$ is independently one of

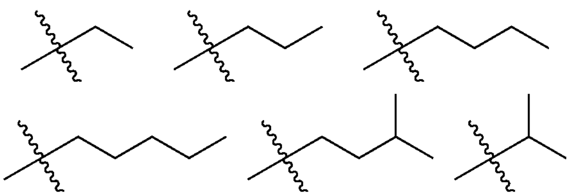

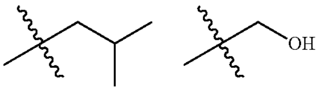

or

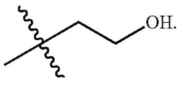

9. The compound or a pharmaceutically acceptable salt, solvate, hydrate or prodrug thereof, of any of embodiments 7-8, wherein L is

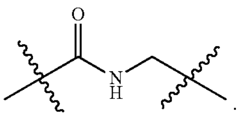 [SMILES: *CNC(*)=O]

10. The compound or a pharmaceutically acceptable salt, solvate, hydrate or prodrug thereof, of any of embodiments 7-9, wherein $R_2$ is

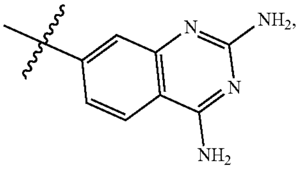

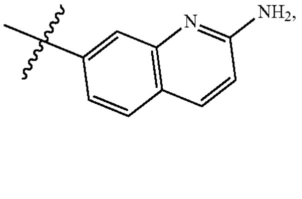

or

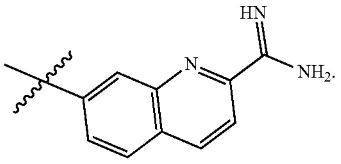

11. The compound, or a pharmaceutically acceptable salt, solvate, hydrate or prodrug thereof, of any of embodiments 7-10 that is any one:

11-1F

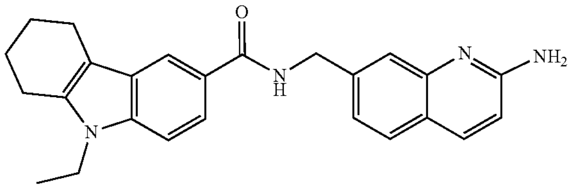

11-2F

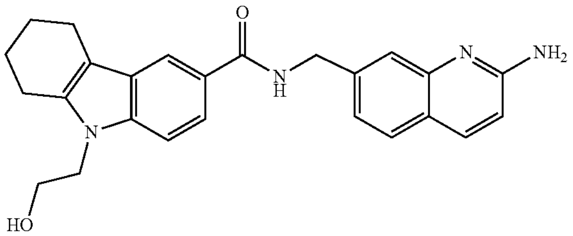

11-9F

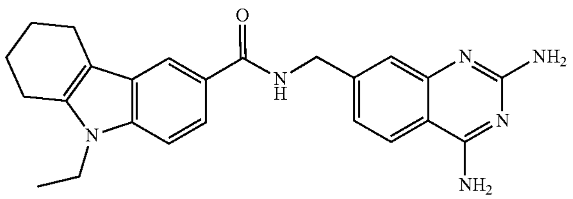

-continued 11-10F

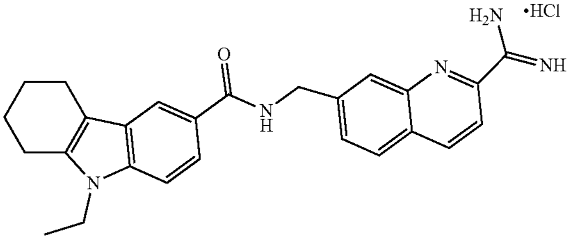

or a pharmaceutically acceptable salt, solvate, hydrate or prodrug thereof.

12. A compound of Formula (I) or (II), or a pharmaceutically acceptable salt, solvate, hydrate or prodrug thereof:

(I)

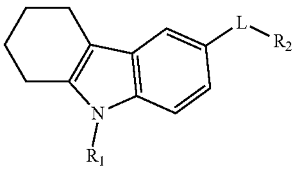

(II)

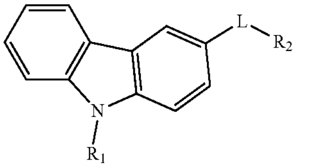

wherein, each $R_1$ is independently optionally substituted alkyl, optionally substituted cycloalkyl, optionally substituted heterocycloalkyl, optionally substituted cycloalkylalkyl, optionally substituted heterocycloalkylalkyl, or optionally substituted hydroxyalkyl;

each L is independently

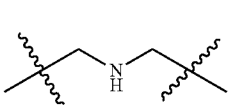 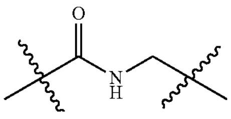 or 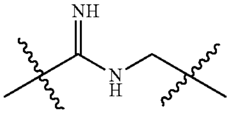 ;

and each $R_2$ is independently optionally substituted aryl, optionally substituted heteroaryl, optionally substituted —C(O)—NH-aryl, or optionally substituted —C(O)— heterocycloalkyl.

13. A compound of Formula (I) or (II) of embodiment 12, or a pharmaceutically acceptable salt, solvate, hydrate or prodrug thereof:

(I)

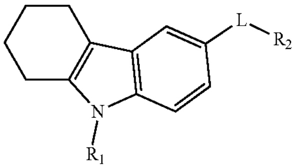

(II)

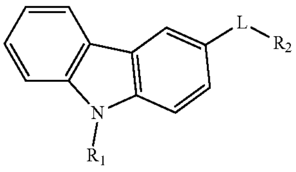

wherein each $R_1$ is independently

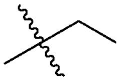 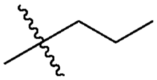 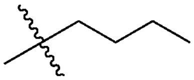

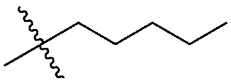 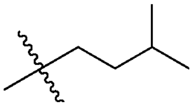 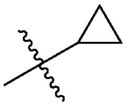

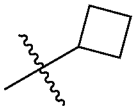 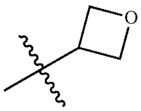 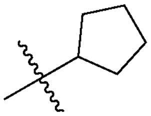

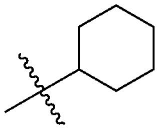 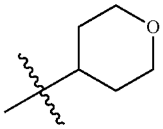 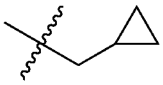

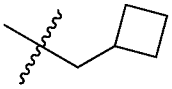 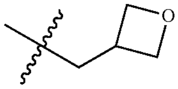 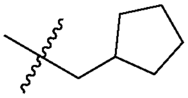

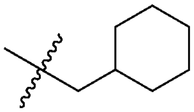 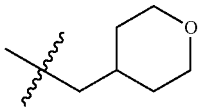 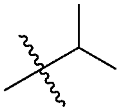

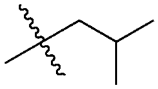 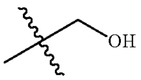 or 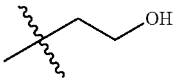

each L is independently

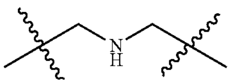 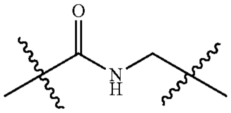 or 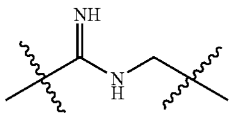

each $R_2$ is independently
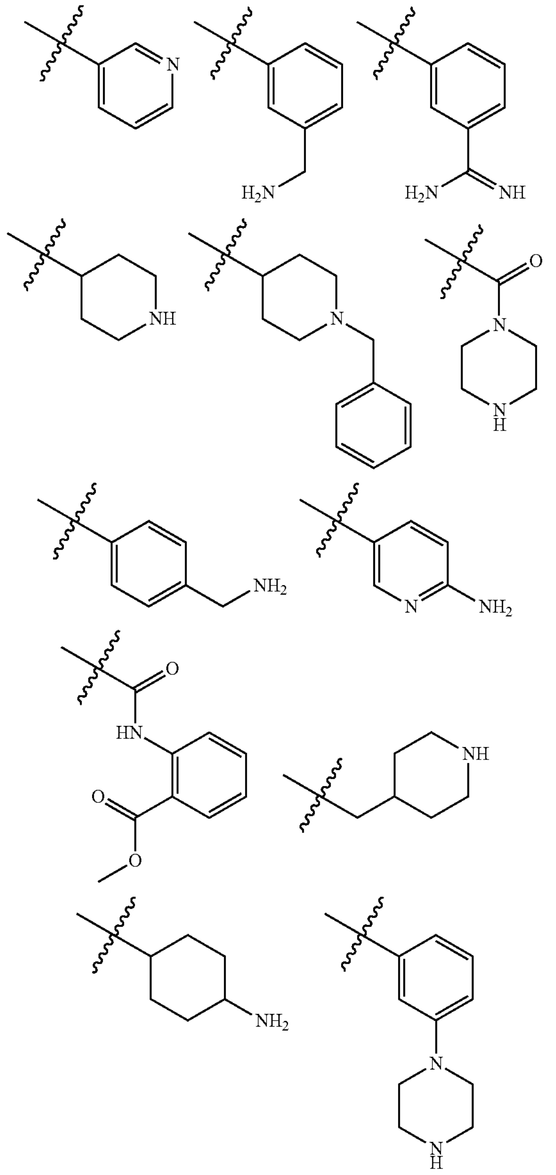
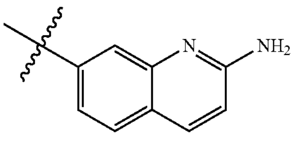
or
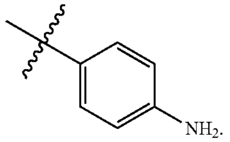
14. The compound of embodiment 12 or 13, or pharmaceutically acceptable salt thereof, that is any one of:
8-1F
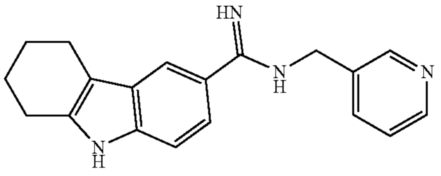
-continued
8-2F
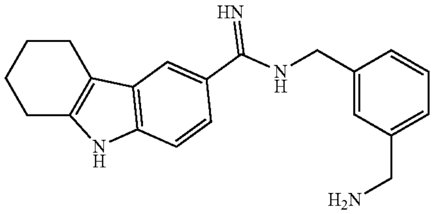
8-3F
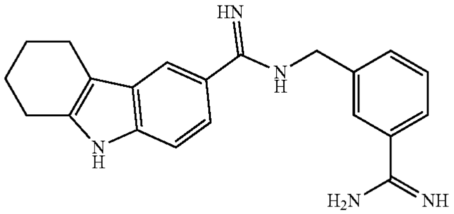
8-ET-1F
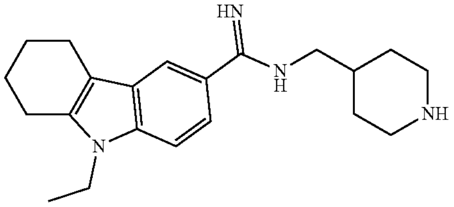
8-ET-2F
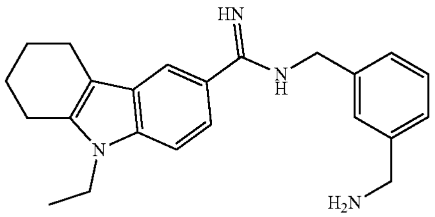
8-ET-4F
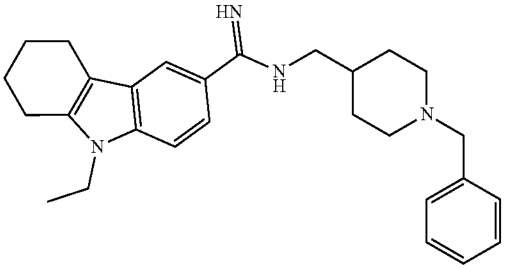
4-1F
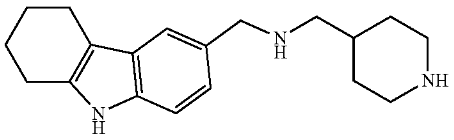
4-2F
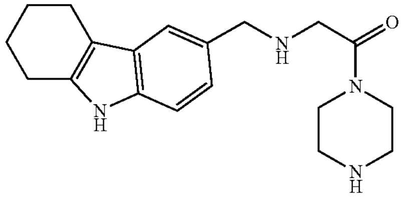

-continued
4-3F
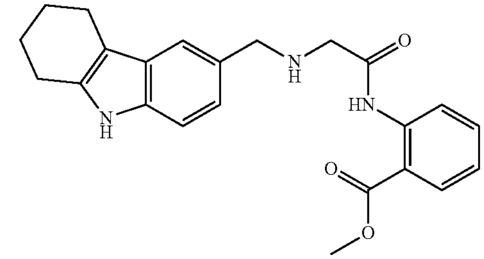
4-5F
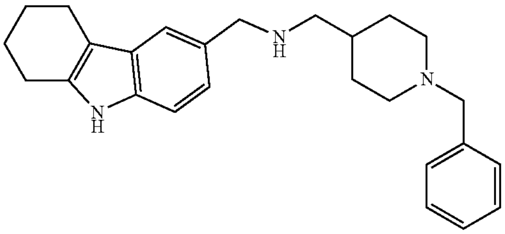
4-ET-1F
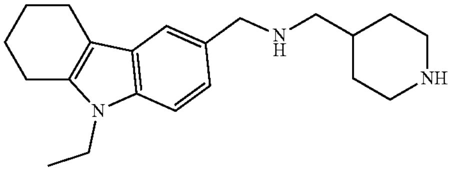
4-ET-2F
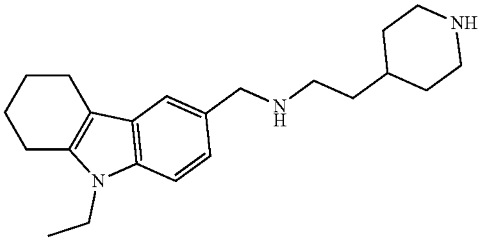
4-ET-3F
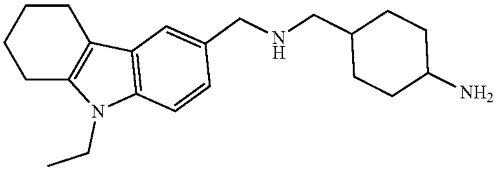
3-3F
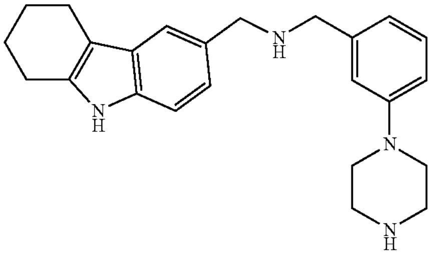
3-4F
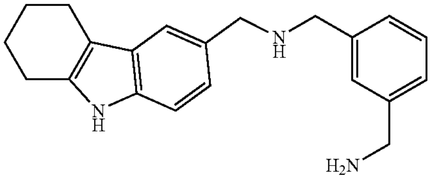
-continued
3-ET-4F
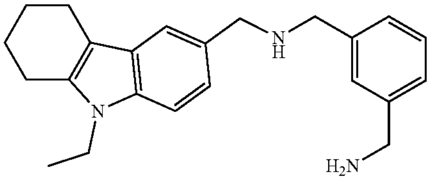
1-ET-1F
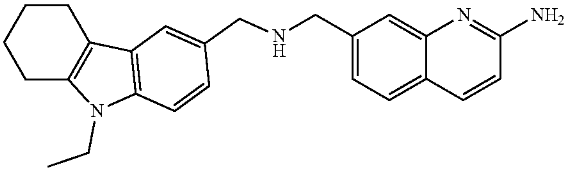
9-1F
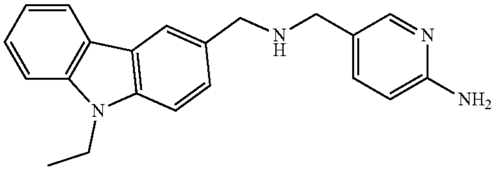
9-2F
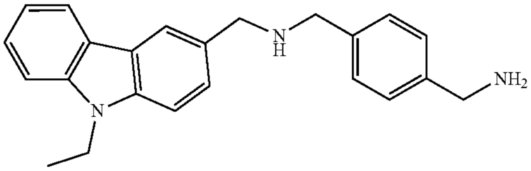
9-5F
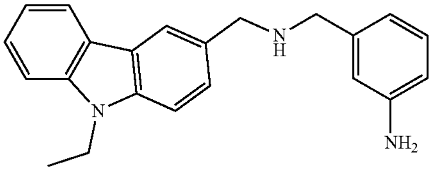
9-6F
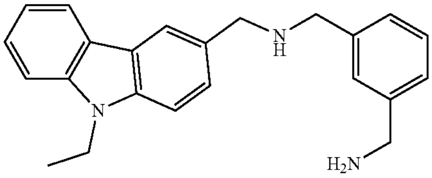
6-1F
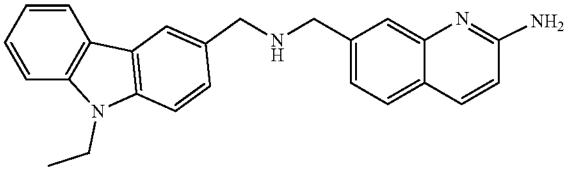
6-2F
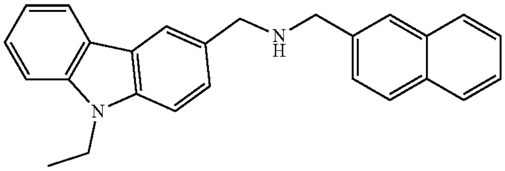

-continued 1-1F

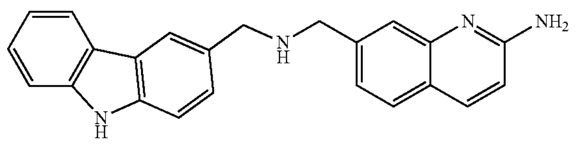

1-ET-1F

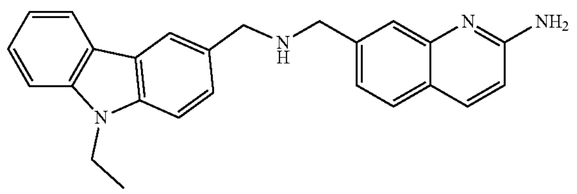

1-BUT-1F

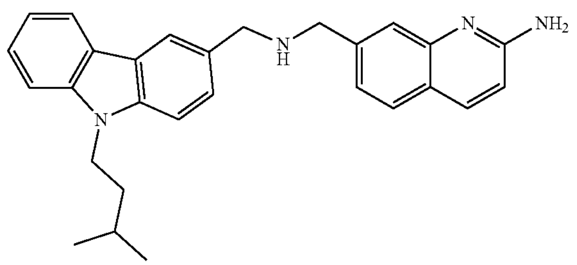

5-1F

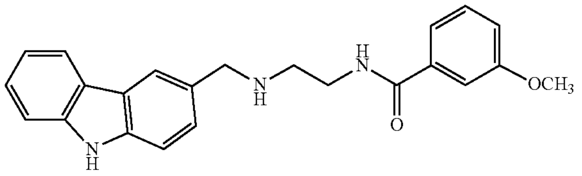

5-3F

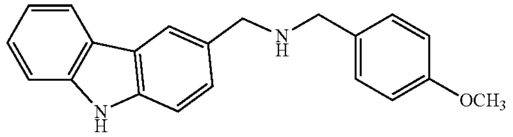

5-4F

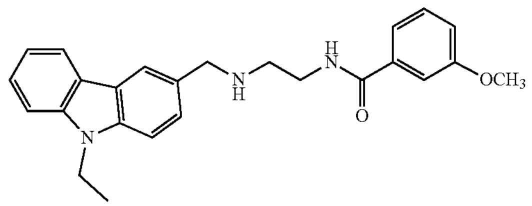

or 5-5F

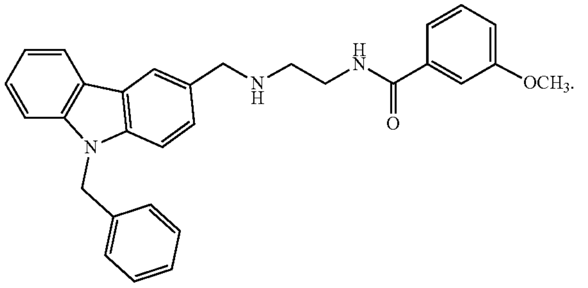

15. A pharmaceutical composition comprising a compound of any one of embodiments 1-14, or a pharmaceutical salt thereof, and a pharmaceutically acceptable carrier.

16. The pharmaceutical composition of embodiment 15, further comprising an additional therapeutic agent.

17. The pharmaceutical composition of embodiment 16, wherein the additional therapeutic agent is an anticancer agent.

18. A method of treating a subject suffering from or susceptible to a proliferative disease, the method comprising administering to the subject a compound of any one of embodiments 1-14, or a pharmaceutical salt thereof, or a pharmaceutical composition of any one of embodiments 15-17.

19. A method of treating a proliferative disease in a subject identified as in need thereof, the method comprising administering to the subject a compound of any one of embodiments 1-14, or a pharmaceutical salt thereof, or a pharmaceutical composition of any one of embodiments 15-17.

20. A method of treating a subject suffering from or susceptible to a proliferative disease, the method comprising administering to the subject a compound of any one of embodiments 1-14, or a pharmaceutical salt thereof, or a pharmaceutical composition of any one of embodiments 15-17, such that said subject is treated for said proliferative disease.

21. A method of treating a proliferative disease in a subject identified as in need thereof, the method comprising administering to the subject a compound of any one of embodiments 1-14, or a pharmaceutical salt thereof, or a pharmaceutical composition of any one of embodiments 15-17, such that said subject is treated for said proliferative disease.

22. The method of any one of embodiments 18-21, wherein the proliferative disease is cancer.

23. The method of any one of embodiments 18-22, wherein the cancer is multiple myeloma, lymphoma, chronic lymphocytic leukemia (CLL), acute myelogenous leukemia (AML), large granular lymphocyte leukemia (LGL), sarcoma, lung cancer, breast cancer, renal cancer, prostate cancer, pancreatic cancer, melanoma, colon carcinoma, gastric carcinoma, cervical cancer, ovarian cancer, liver cancer, or head and neck cancer.

REFERENCES (1) Blanc, R. S.; Richard, S. Arginine methylation: the coming of age. *Mol. Cell* 2017, 65, 8-24.

(2) Pal, S.; Vishwanath, S. N.; Erdjument-Bromage, H.; Tempst, P.; Sif, S. Human SWI/SNF-associated PRMT5 methylates histone H3 arginine 8 and negatively regulates expression of ST7 and NM23 tumor suppressor genes. *Mol. Cell. Biol.* 2004, 24, 9630-9645.

(3) Fabbrizio, E.; El Messaoudi, S.; Polanowska, J.; Paul, C.; Cook, J. R.; Lee, J. H.; Negre, V.; Rousset, M.; Pestka, S.; Le Cam, A.; Sardet, C. Negative regulation of transcription by the type II arginine methyltransferase PRMT5. *EMBO Rep.* 2002, 3, 641-645.

(4) Karkhanis, V.; Hu, Y. J.; Baiocchi, R. A.; Imbalzano, A. N.; Sif, S. Versatility of PRMT5-induced methylation in growth control and development. *Trends Biochem. Sci.* 2011, 36, 633-641.

(5) Xu, X.; Hoang, S.; Mayo, M. W.; Bekiranov, S. Application of machine learning methods to histone methylation ChIP-Seq data reveals H4R3me2 globally represses gene expression. *BMC Bioinformatics* 2010, 11, 396.

(6) Stopa, N.; Krebs, J. E.; Shechter, D. The PRMT5 arginine methyltransferase: many roles in development, cancer and beyond. *Cell. Mol. Life Sci.* 2015, 72, 2041-2059.

(7) Kaniskan, H. Ü.; Jin, J. Recent progress in developing selective inhibitors of protein methyltransferases. *Curr. Opin. Chem. Biol.* 2017, 39, 100-108.

(8) Hu, H.; Qian, K.; Ho, M. C.; Zheng, Y. G. Small molecule inhibitors of protein arginine methyltransferases. *Expert Opin. Invest. Drugs* 2016, 25, 335-358.

(9) Mao, R.; Shao, J.; Zhu, K.; Zhang, Y.; Ding, H.; Zhang, C.; Shi, Z.; Jiang, H.; Sun, D.; Duan, W.; Luo, C. Potent, selective, and cell active protein arginine methyltransferase 5 (PRMT5) inhibitor developed by structure-based virtual screening and hit optimization. *J. Med. Chem.* 2017, 60, 6289-6304.

(10) Chan-Penebre, E.; Kuplast, K. G.; Majer, C. R.; Boriack-Sjodin, P. A.; Wigle, T. J.; Johnston, L. D.; Rioux, N.; Munchhof, M. J.; Jin, L.; Jacques, S. L.; West, K. A.; Lingaraj, T.; Stickland, K.; Ribich, S. A.; Raimondi, A.; Scott, M. P.; Waters, N. J.; Pollock, R. M.; Smith, J. J.; Barbash, O.; Pappalardi, M.; Ho, T. F.; Nurse, K.; Oza, K. P.; Gallagher, K. T.; Kruger, R.; Moyer, M. P.; Copeland, R. A.; Chesworth, R.; Duncan, K. W. A selective inhibitor of PRMT5 with in vivo and in vitro potency in MCL models. *Nat. Chem. Biol.* 2015, 11, 432-437.

(11) Bonday, Z. Q.; Cortez, G. S.; Grogan, M. J.; Antonysamy, S.; Weichert, K.; Bocchinfuso, W. P.; Li, F.; Kennedy, S.; Li, B.; Mader, M. M.; Arrowsmith, C. H. LLY-283, a potent and selective inhibitor of arginine methyltransferase 5, PRMT5, with antitumor activity. *ACS Med. Chem. Lett.* 2018, 11, 612-617.

(12) Alinari, L.; Mahasenan, K. V.; Yan, F.; Karkhanis, V.; Chung, J.-H.; Smith, E. M.; Quinion, C.; Smith, P. L.; Kim, L.; Patton, J. T.; Lapalombella, R.; Yu, B.; Wu, Y.; Roy, S.; De Leo, A.; Pileri, S.; Agostinelli, C.; Bradner, J. E.; Chen-Kiang, S.; Elemento, O.; Motiwala, T.; Majumder, S.; Byrd, J. C.; Jacob, S.; Sif, S, Li, C.; Baiocchi, R. A. Selective inhibition of protein arginine methyltransferase 5 blocks initiation and maintenance of B-cell transformation. *Blood,* 2015, 125, 2530-2543.

(13) Wang, Y.; Hu, W.; Yuan, Y. Protein arginine methyltransferase 5 (PRMT5) as an anticancer target and its inhibitor discovery. *J. Med. Chem.* 2018, 61, 9429-9441.

(14) Beaudet, L.; Rodriguez-Suarez, R.; Venne, M. H.; Caron, M.; Bédard, J.; Brechler, V.; Parent, S.; Bielefeld-Sévigny, M. AlphaLISA immunoassays: the no-wash alternative to ELISAs for research and drug discovery. *Nat. Methods.* 2008, 5, A10-A11.

(15) Cinelli, M. A.; Li, H.; Chreifi, G.; Martisek, P.; Roman, L. J.; Poulos, T. L.; Silverman, R. B. Simplified 2-aminoquinoline-based scaffold for potent and selective neuronal nitric oxide synthase inhibition. *J. Med. Chem.* 2014, 57, 1513-1530.

(16) Pal, Sharmistha, et al. *Molecular and cellular biology* 24.21 (2004): 9630-9645.

(17) Antonysamy, Stephen, et al. *PNAS* 109.44 (2012): 17960-17965.

(18) Alinari, Lapo, et al. *Blood* 125.16 (2015): 2530-2543.

(19) Chan-Penebre, Elayne, et al. *Nature chemical biology* 11.6 (2015): 432-437.

(20) Mavrakis, Konstantinos J., et al. *Science* 351.6278 (2016): 1208-1213.

(21) Bonday, Zahid Q., et al. *ACS medicinal chemistry letters* 9.7 (2018): 612-617

INCORPORATION BY REFERENCE

The contents of all references (including literature references, issued patents, published patent applications, and co-pending patent applications) cited throughout this application are hereby expressly incorporated herein in their entireties by reference.

EQUIVALENTS

Those skilled in the art will recognize, or be able to ascertain using no more than routine experimentation, many equivalents of the specific embodiments of the invention described herein. Such equivalents are intended with be encompassed by the following claims.

What is claimed:

1. A compound of Formula (III), or a pharmaceutically acceptable salt, solvate, hydrate or prodrug thereof:

Formula III

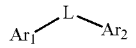

wherein, $Ar_1$ is

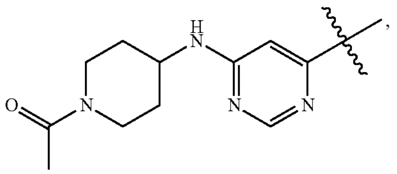 [SMILES: *c1cc(NC2CCN(C(C)=O)CC2)ncn1]

each $R^B$ is independently selected from the group consisting of hydrogen, optionally substituted aliphatic, optionally substituted heterocyclyl, or two $R^B$ groups are taken together with their intervening atoms to form an optionally substituted heterocyclic ring;

L is

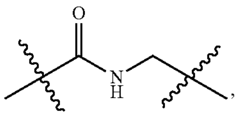 [SMILES: *CNC(*)=O]

and $Ar_2$ is any one of the following groups:

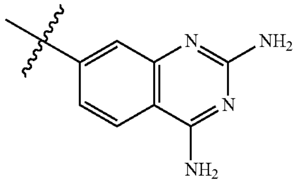

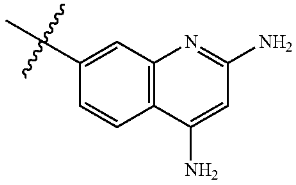

-continued

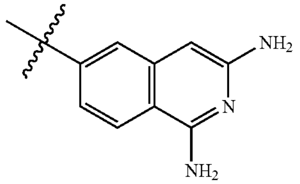

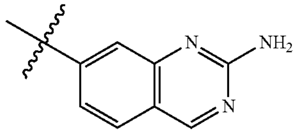

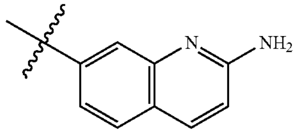

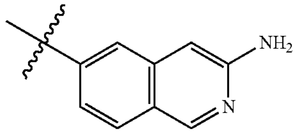

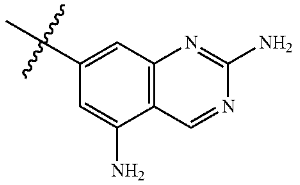

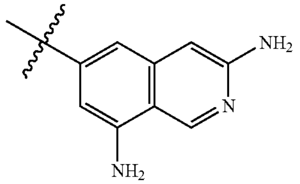

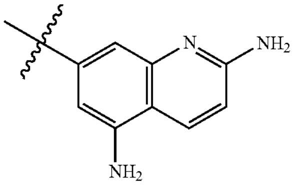

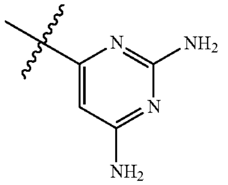

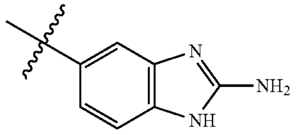

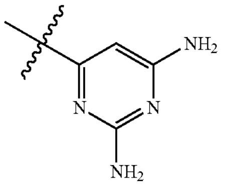

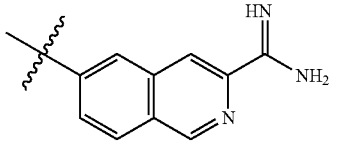

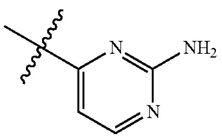

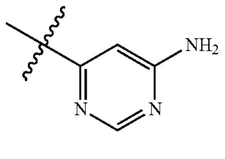

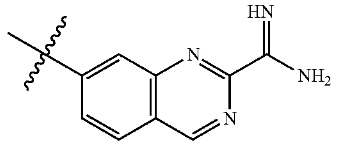

-continued

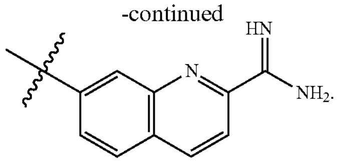

2. The compound of claim 1, or a pharmaceutically acceptable salt, solvate, hydrate or prodrug thereof, wherein $Ar_2$ is

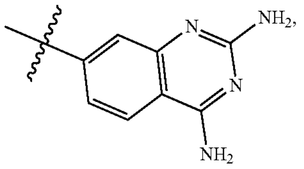

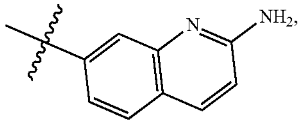

or

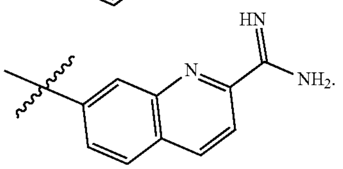

3. The compound of claim 1, or a pharmaceutically acceptable salt, solvate, hydrate or prodrug thereof, wherein the compound is of the formula:

15-1F

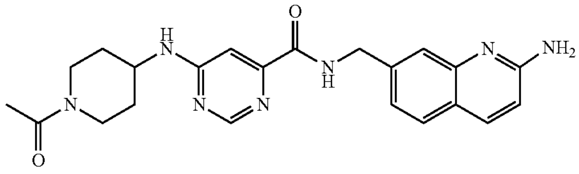

15-2F

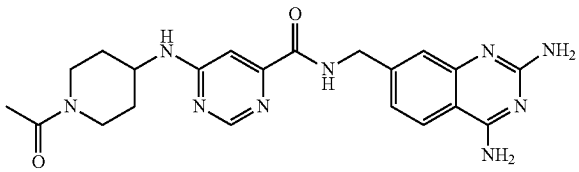

15-8F

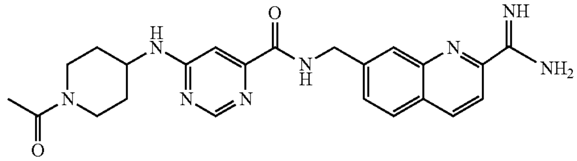

or a pharmaceutically acceptable salt, solvate, hydrate or prodrug thereof.

4. A compound, or a pharmaceutically acceptable salt, solvate, hydrate or prodrug thereof, represented by Formula (IV) or (V):

Formula IV
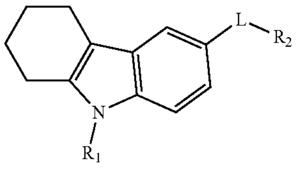
Formula V
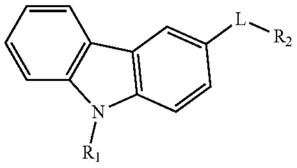
wherein
each $R_1$ is independently one of:
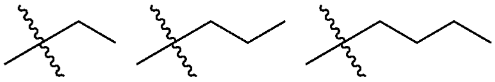
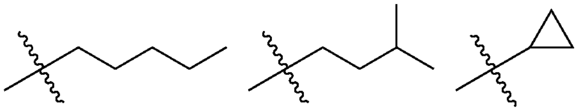
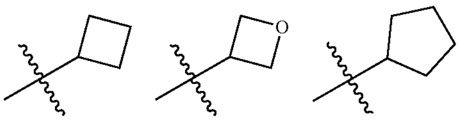
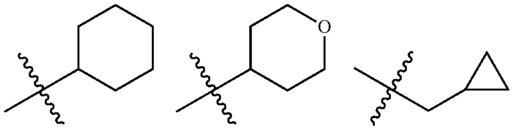
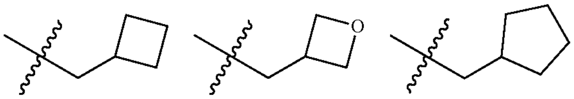
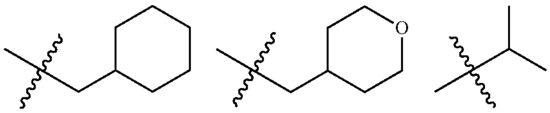
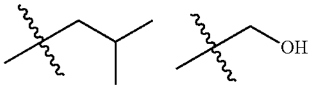
or
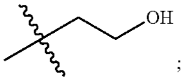
;
Each L is independently:
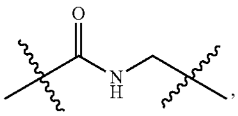
,
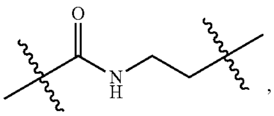
,
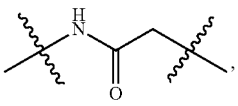
, or
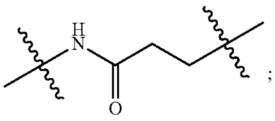
;
Each $R_2$ is independently one of:
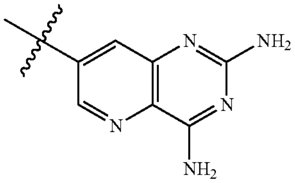
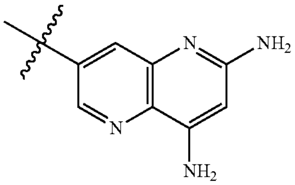
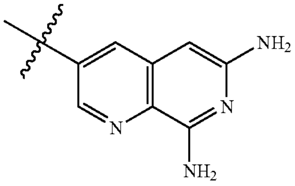
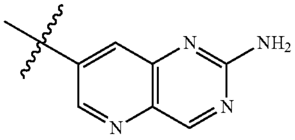
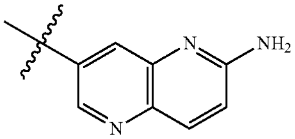
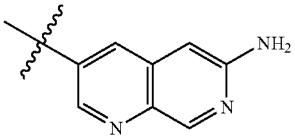
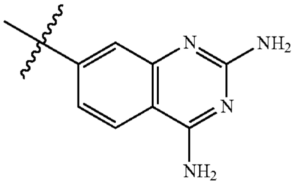
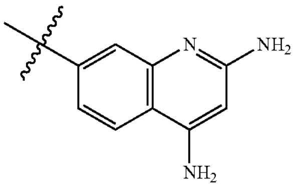
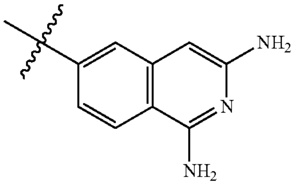
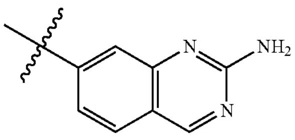

-continued
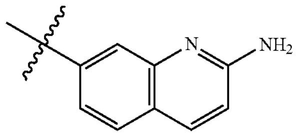
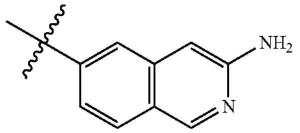
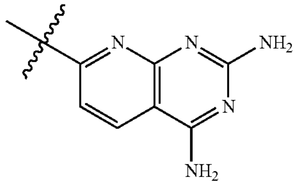
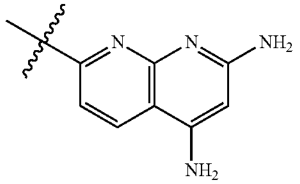
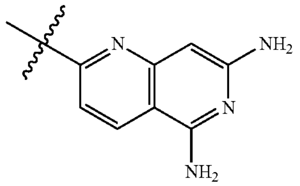
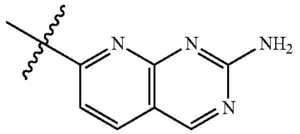
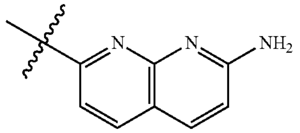
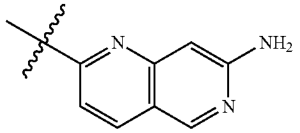
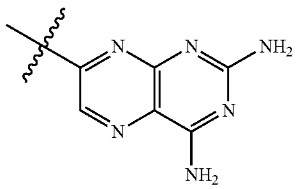
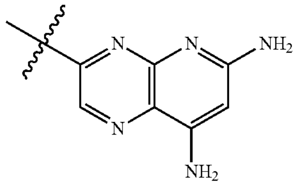
-continued
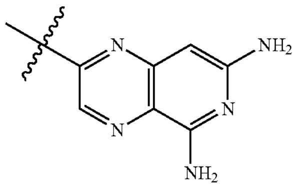
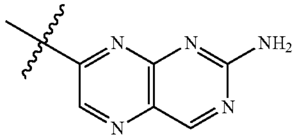
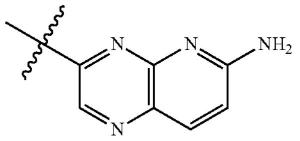
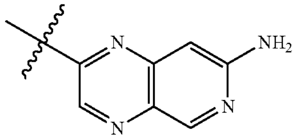
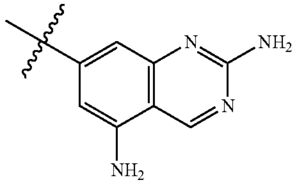
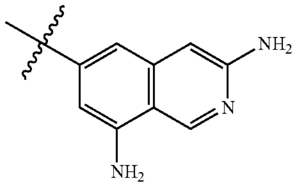
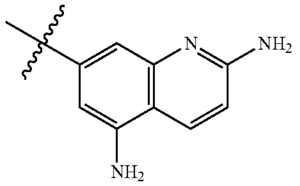
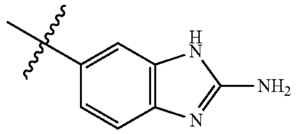
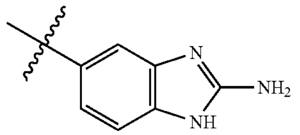
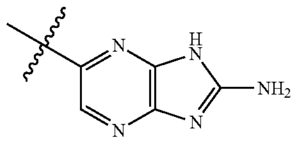

-continued
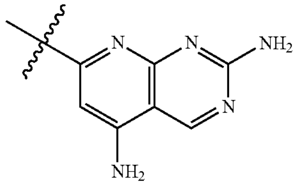
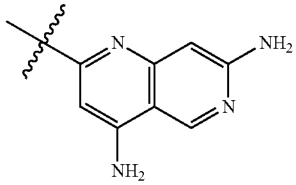
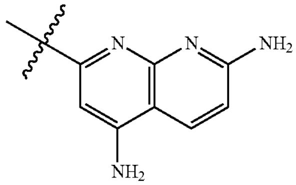
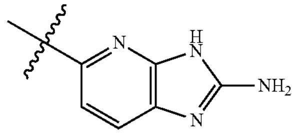
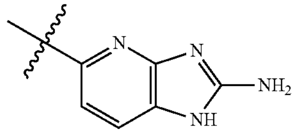
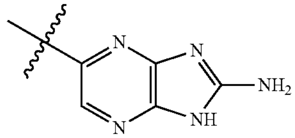
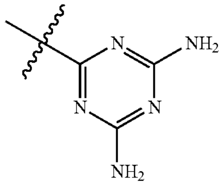 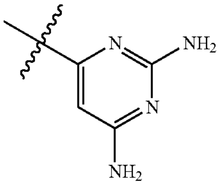
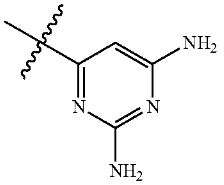 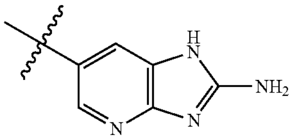
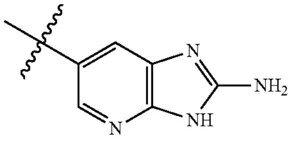 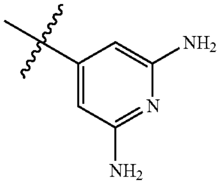
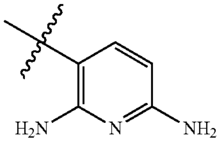 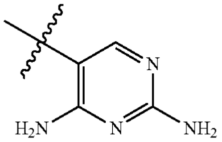
-continued
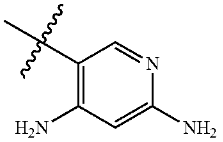 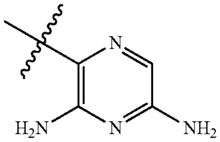
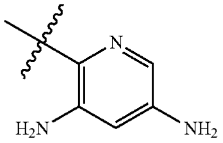 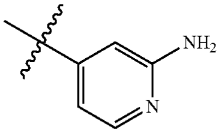
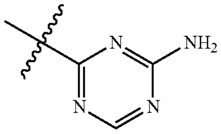 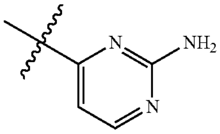
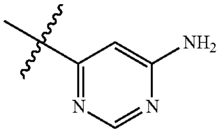 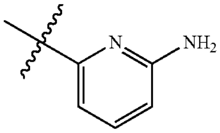
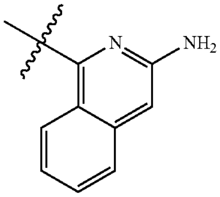 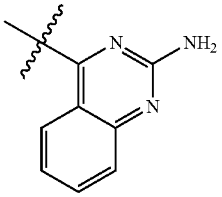
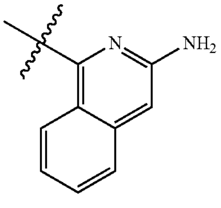 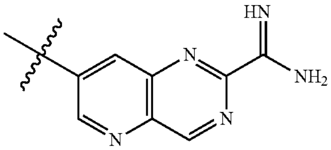
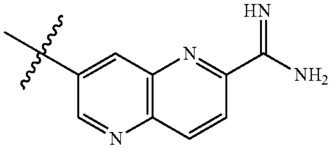
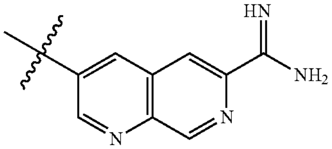
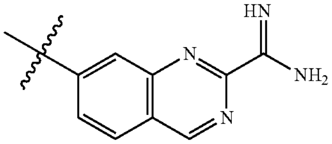
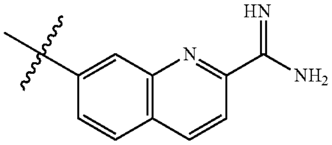
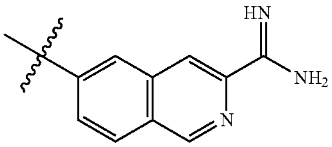

-continued

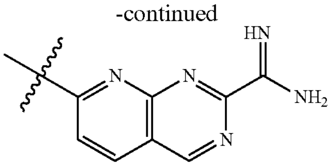

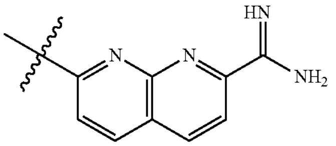

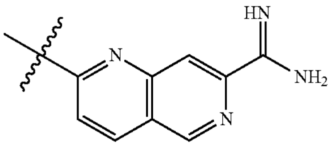

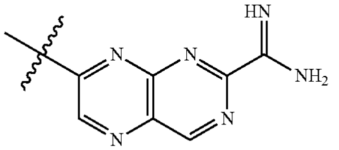

and

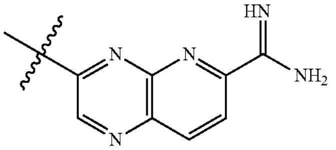

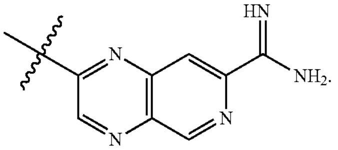

5. The compound, or a pharmaceutically acceptable salt, solvate, hydrate or prodrug thereof, of claim 4, wherein each $R_1$ is independently one of

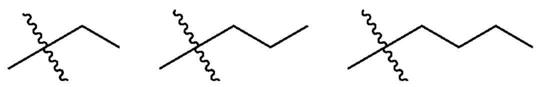

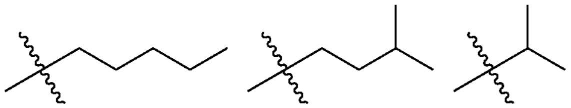

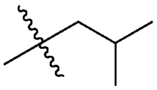

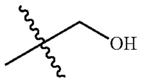

or

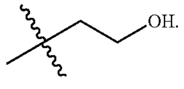

6. The compound or a pharmaceutically acceptable salt, solvate, hydrate or prodrug thereof, of claim 4, wherein L is

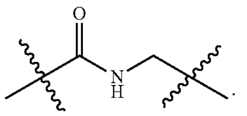 [SMILES: *CNC(*)=O]

7. The compound or a pharmaceutically acceptable salt, solvate, hydrate or prodrug thereof, of claim 4, wherein $R_2$ is

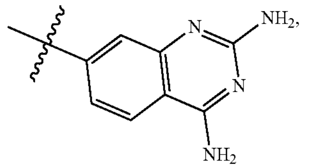

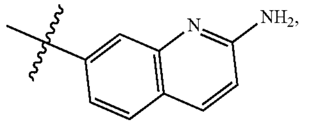

or

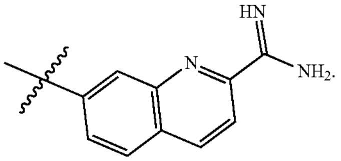

8. The compound, or a pharmaceutically acceptable salt, solvate, hydrate or prodrug thereof, of claim 4, wherein the compound is of the formula 11-1F

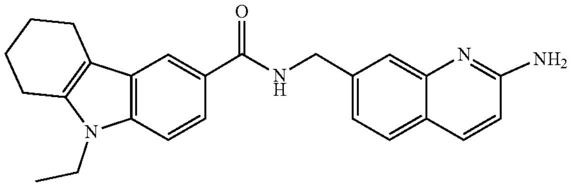

11-2F

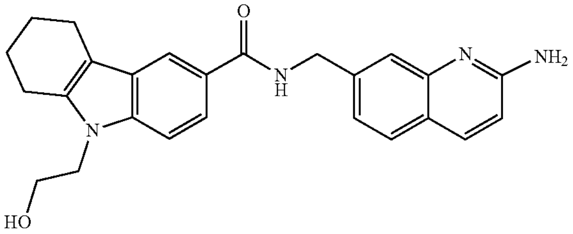

11-9F

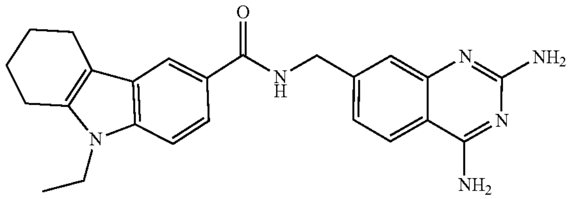

11-10F

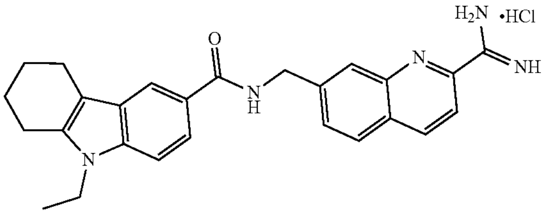

or a pharmaceutically acceptable salt, solvate, hydrate or prodrug thereof.

9. A compound of Formula (I) or (II), or a pharmaceutically acceptable salt, solvate, hydrate or prodrug thereof:

(I)

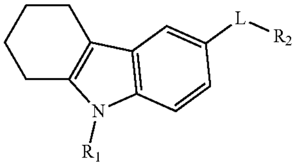

(II)

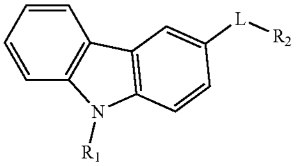

wherein, each $R_1$ is independently optionally substituted alkyl or optionally substituted hydroxyalkyl;

each L is independently

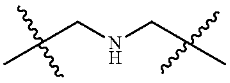 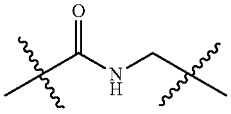 or 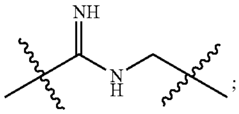;

each $R_2$ is independently optionally substituted aryl, optionally substituted —C(O)—NH-aryl, or optionally substituted —C(O)-heterocycloalkyl.

10. A compound of Formula (I) or (II), or a pharmaceutically acceptable salt, solvate, hydrate or prodrug thereof:

(I)

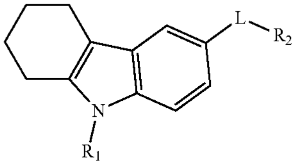

(II)

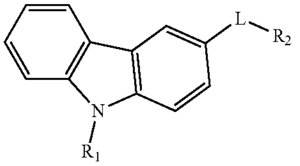

wherein each $R_1$ is independently

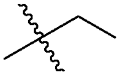 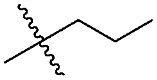 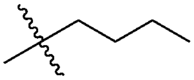

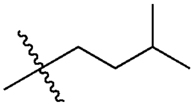 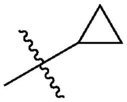 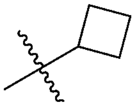

-continued

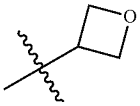 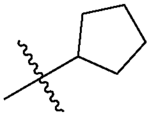 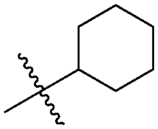

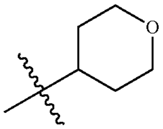 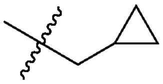 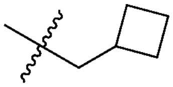

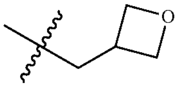 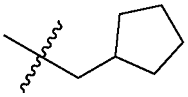 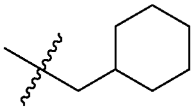

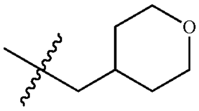 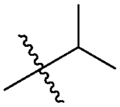 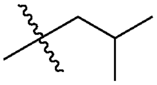

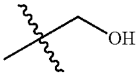 or 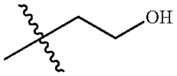

each L is independently

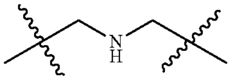 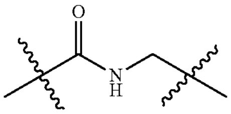 or 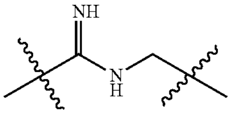

each $R_2$ is independently

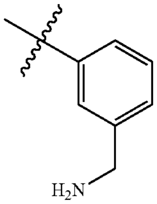 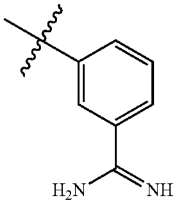 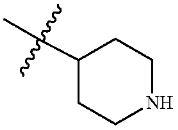

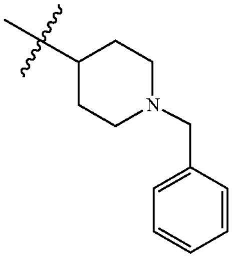 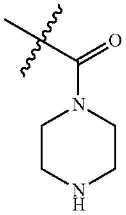

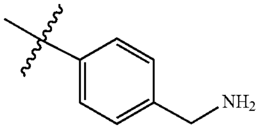 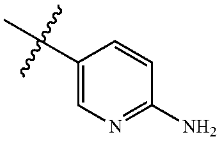

-continued
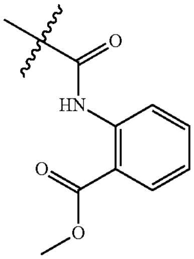
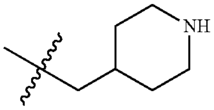
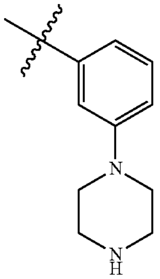
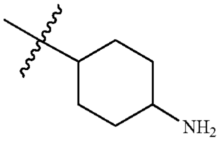
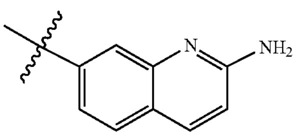
or
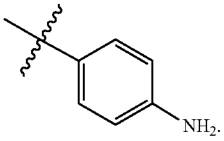
11. The compound of claim 10, or pharmaceutically acceptable salt thereof, that is any one of:
8-ET-1F
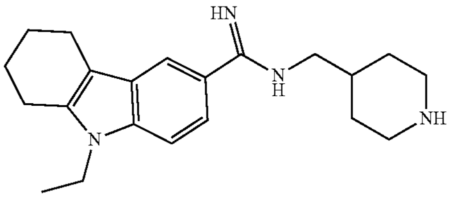
*-ET-2F
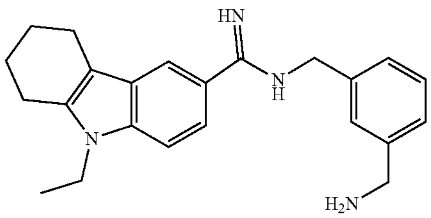
8-ET-4F
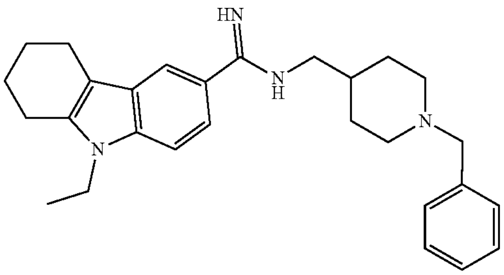
-continued
4-ET-3F
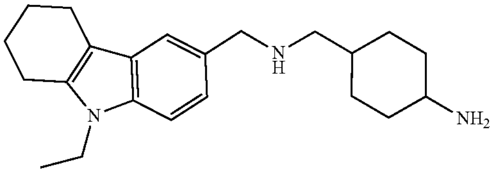
4-ET-1F
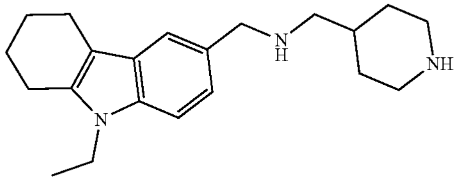
4-ET-2f
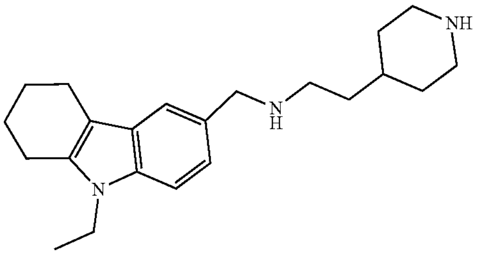
3-ET-4F
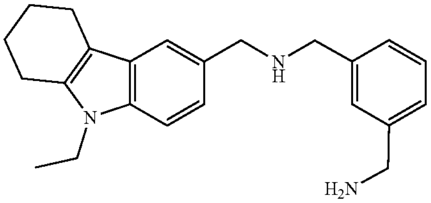
1-ET-1F
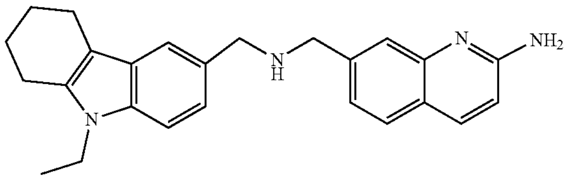
9-1F
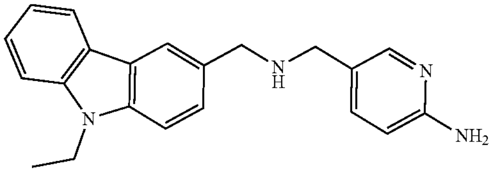
9-2F
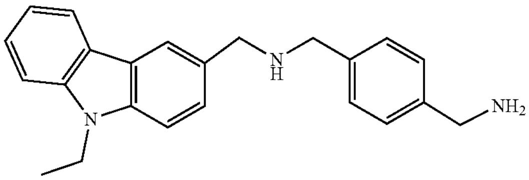

-continued 9-5F

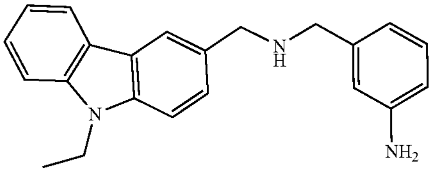

9-6F

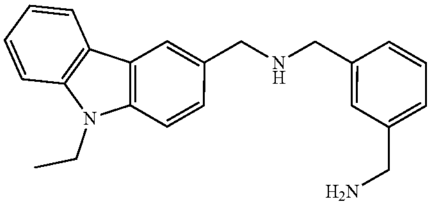

6-1F

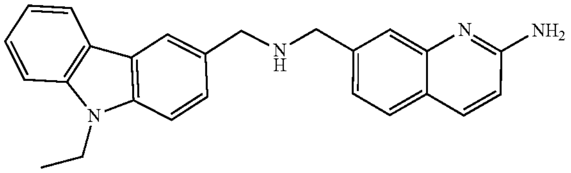

1-ET-1F

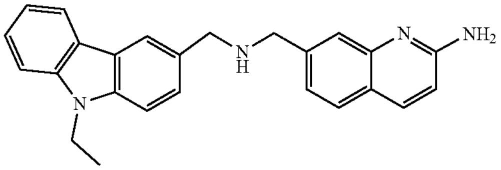

or

1-BUT-1F

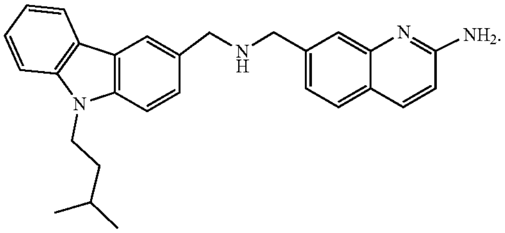

12. A pharmaceutical composition comprising a compound of claim 4, or a pharmaceutical salt thereof, and a pharmaceutically acceptable carrier.

13. A method of treating a subject suffering from or susceptible to a proliferative disease, the method comprising administering to the subject a compound of claim 4.

14. A method of treating a proliferative disease in a subject identified as in need thereof, the method comprising administering to the subject a compound of claim 4.

15. A method of treating a subject suffering from or susceptible to a proliferative disease, the method comprising administering to the subject a compound of claim 4, such that said subject is treated for said proliferative disease.

16. A method of treating a proliferative disease in a subject identified as in need thereof, the method comprising administering to the subject a compound of claim 4, such that said subject is treated for said proliferative disease.

17. The method of claim 14, wherein the proliferative disease is cancer.

18. A pharmaceutical composition comprising a compound of claim 1, or a pharmaceutical salt thereof, and a pharmaceutically acceptable carrier.

19. A method of treating a subject suffering from or susceptible to a proliferative disease, the method comprising administering to the subject a compound of claim 1.

20. A method of treating a proliferative disease in a subject identified as in need thereof, the method comprising administering to the subject a compound of claim 1.

21. A method of treating a subject suffering from or susceptible to a proliferative disease, the method comprising administering to the subject a compound of claim 1, such that said subject is treated for said proliferative disease.

22. A method of treating a proliferative disease in a subject identified as in need thereof, the method comprising administering to the subject a compound of claim 1, such that said subject is treated for said proliferative disease.

23. The compound of claim 1, or a pharmaceutically acceptable salt thereof.

24. The compound of claim 9, or a pharmaceutically acceptable salt thereof.

25. The compound of claim 9, or a pharmaceutically acceptable salt thereof.

26. The compound of claim 10, or a pharmaceutically acceptable salt thereof.

* * * * *